United States Patent
Andrews et al.

(10) Patent No.: US 10,525,070 B2
(45) Date of Patent: Jan. 7, 2020

(54) METHOD OF TREATING HEART FAILURE

(71) Applicants: Duke University, Durham, NC (US); Cornell University, Ithaca, NY (US)

(72) Inventors: Nancy C. Andrews, Durham, NC (US); Wenjing Xu, Durham, NC (US); Anthony A. Sauve, New Rochelle, NY (US)

(73) Assignees: DUKE UNIVERSITY, Durham, NC (US); CORNELL UNIVERSITY, Ithaca, NY (US)

( * ) Notice: Subject to any disclaimer, the term of this patent is extended or adjusted under 35 U.S.C. 154(b) by 139 days.

(21) Appl. No.: 15/550,150

(22) PCT Filed: Feb. 10, 2016

(86) PCT No.: PCT/US2016/017371
§ 371 (c)(1),
(2) Date: Aug. 10, 2017

(87) PCT Pub. No.: WO2016/130691
PCT Pub. Date: Aug. 18, 2016

(65) Prior Publication Data
US 2019/0038647 A1 Feb. 7, 2019

Related U.S. Application Data

(60) Provisional application No. 62/216,698, filed on Sep. 10, 2015, provisional application No. 62/215,502, filed on Sep. 8, 2015, provisional application No. 62/114,501, filed on Feb. 10, 2015.

(51) Int. Cl.
*A61K 31/706* (2006.01)
*A61P 9/00* (2006.01)

(52) U.S. Cl.
CPC .............. *A61K 31/706* (2013.01); *A61P 9/00* (2018.01)

(58) Field of Classification Search
None
See application file for complete search history.

(56) References Cited

U.S. PATENT DOCUMENTS

| | | | |
|---|---|---|---|
| 2002/0128205 A1* | 9/2002 | Stamler | A61K 31/365 514/2.4 |
| 2012/0135091 A1* | 5/2012 | Roth | A61K 31/05 424/696 |
| 2012/0172584 A1 | 7/2012 | Sauve et al. | |

FOREIGN PATENT DOCUMENTS

WO  WO 2006/105440 A2  10/2006

OTHER PUBLICATIONS

Galluzzi, Cell, Dec. 4, 2014; 159(6): 1263-1276. (Year: 2014).*

(Continued)

*Primary Examiner* — Layla D Berry
(74) *Attorney, Agent, or Firm* — Leydig, Voit & Mayer, Ltd.

(57) ABSTRACT

Disclosed herein is a method for treating heart failure in a subject in need thereof. The method includes administering a therapeutically effective amount of nicotinamide riboside to the subject. The heart failure may be associated with iron deficiency. The method may also include administering iron to the subject.

13 Claims, 33 Drawing Sheets
Specification includes a Sequence Listing.

(56) References Cited

OTHER PUBLICATIONS

Xu et al., Lethal Cardiomyopathy in Mice Lacking Transferrin Receptor in the Heart, Cell Reports, 13(3): 533-545 (2015).
European Patent Office, extended European Search Report in Application No. 16749811.2 (dated Feb. 8, 2018).
Brahma et al., Fibroblast growth factor 21 is induced upon cardiac stress and alters cardiac lipid homeostasis, *Journal of Lipid Research*, 55(11): 2229-2241 (2014).
Cerutti et al., "NAD+-Dependent Activation of Sirt1 Corrects the Phenotype in a Mouse Model of Mitochondrial Disease", *Cell Metabolism*, 19(6): 1042-1049 (2014).
Esposito, et al., "Cellular and functional defects in a mouse model of heart failure", *Am. J. Physiol. Heart Circ. Physiol.*, 279:H3101-3112 (2000).
Janssen, et al., Spectrophotometric Assay for Complex 1 of the Respiratory Chain in Tissue Samples and Cultured Fibroblasts, *Clinical Chemistry*, 53(4):729-734 (2007).
Jimenez et al,, "Autophagy and mitophagy in the myocardium: therapeutic potential and concerns", *British Journal of Pharmacology*, 171: 1907-1916 (2014).
Levy, et al., "Transferrin receptor is necessary for development of erythrocytes and the nervous system", *Nature Genetics* 21:396-399 (1999).
Mcdonagh et al., "Iron therapy for the treatment of iron deficiency in chronic heart failure: intravenous or oral?", *European Journal of Heart Failure*, 17:248-262 (2015).
Nagao et al., "Quantification of myocardial iron deficiency in nonischernic heart failure by cardiac T2* magnetic resonance imaging", *American Journal of Cardiology*, 113(6): 1024-1030 (2014).
Schmidt, et al. , "The Transferrin Receptor Modulates Hfe-Dependent Regulation of Hepcidin Expression", *Cell Metabolism*,7: 205-214 (2008).
Spinazzi et al., "Optimization of respiratory chain enzymatic assays in muscle for the diagnosis of mitochondrial disorders", *Mitochondrion* 11:893-904 (2011).
Sukoyan et al., "Mechanism of Cardioprotective Effect of Adenocine and Non-Glycoside Cardiotonic Drugs during Experimental Chronic Cardiac Insufficiency", *Bulletin of Experimental Biology and Medicine*, 150(5): 610-613 (2011).
Torrance et al. , "Iron: Tissue Iron Stores", *Methods in Hematology*, 1: 90-115 (1980).
Yang et al., "Syntheses of Nicotinamide Riboside and Derivatives: Effective Agents for Increasing Nicotinamide Adenine Dinucleotide Concentrations in Mammalian Cells", *J. Med. Chem.* 50:6458-6461 (2007).
WIPO, International Search Report in Application No. PCT/US16/17371 dated May 3, 2016, 4 pages.

\* cited by examiner

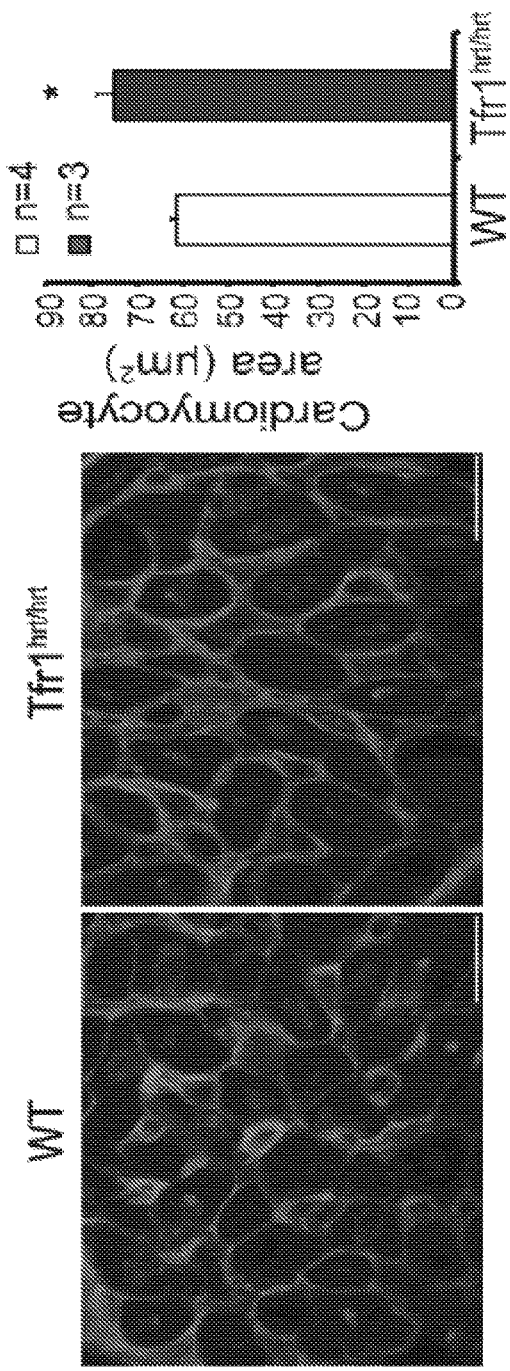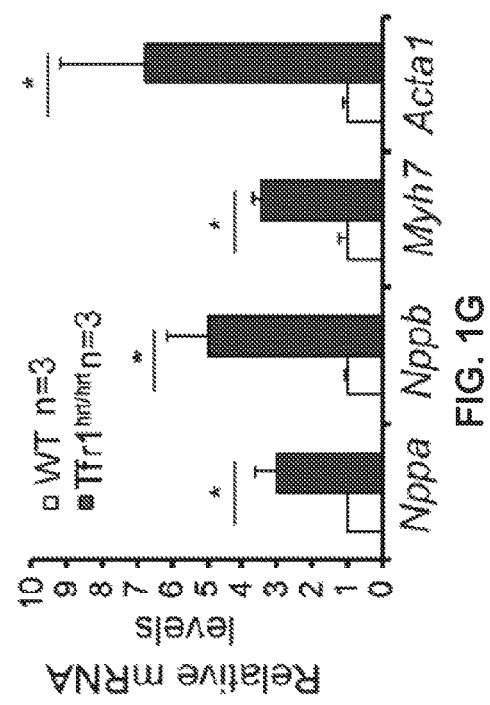
FIG. 1F
FIG. 1G

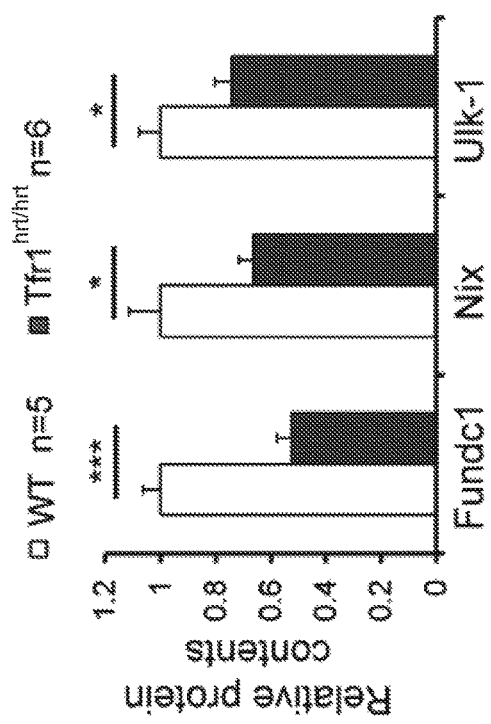
FIG. 5A
FIG. 5B

EDD: end diastolic diameter
ESD: end systolic diameter

SEQUENCE LISTING

```
<160> NUMBER OF SEQ ID NOS: 110

<210> SEQ ID NO 1
<211> LENGTH: 24
<212> TYPE: DNA
<213> ORGANISM: Artificial Sequence
<220> FEATURE:
<223> OTHER INFORMATION: Synthetic Primer

<400> SEQUENCE: 1
cagtaatccc agaggaatca ttag                                          24

<210> SEQ ID NO 2
<211> LENGTH: 22
<212> TYPE: DNA
<213> ORGANISM: Artificial Sequence
<220> FEATURE:
<223> OTHER INFORMATION: Synthetic Primer

<400> SEQUENCE: 2
ctaaaccggg tgtatgacaa tg                                            22

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
ccatattggc agaacgaaaa c                                             21
```

```
<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
gcttcaaaaa tcccttccag g                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
gaatggcttc cttccatcaa                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
atcttcaaag gctgcaggaa                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic Primer

<400> SEQUENCE: 7
cggatggttt ttggcagtta g                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic Primer

<400> SEQUENCE: 8
gcctttacga tatctcagtc c                                              21

<210> SEQ ID NO 9
<211> LENGTH: 18
<212> TYPE: DNA
<213> ORGANISM: Artificial Sequence
<220> FEATURE:
<223> OTHER INFORMATION: Synthetic Primer

<400> SEQUENCE: 9 gagggggagtg ttgcaata                                                 18

<210> SEQ ID NO 10
<211> LENGTH: 16
<212> TYPE: DNA
<213> ORGANISM: Artificial Sequence
<220> FEATURE:
<223> OTHER INFORMATION: Synthetic Primer
```

-continued

```
<400> SEQUENCE: 10
tctgacacta gccttc                                                      16

<210> SEQ ID NO 11
<211> LENGTH: 21
<212> TYPE: DNA
<213> ORGANISM: Artificial Sequence
<220> FEATURE:
<223> OTHER INFORMATION: Synthetic Primer

<400> SEQUENCE: 11
tcaagccaga tcagcattct c                                                21

<210> SEQ ID NO 12
<211> LENGTH: 21
<212> TYPE: DNA
<213> ORGANISM: Artificial Sequence
<220> FEATURE:
<223> OTHER INFORMATION: Synthetic Primer

<400> SEQUENCE: 12
agccagtttc atctccacat g                                                21

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer

<400> SEQUENCE: 13
tcgtcttggc cttttggct                                                   19

<210> SEQ ID NO 14
<211> LENGTH: 22
<212> TYPE: DNA
<213> ORGANISM: Artificial Sequence
<220> FEATURE:
<223> OTHER INFORMATION: Synthetic Primer

<400> SEQUENCE: 14
tccaggtggt ctagcaggtt ct                                               22

<210> SEQ ID NO 15
<211> LENGTH: 21
<212> TYPE: DNA
<213> ORGANISM: Artificial Sequence
<220> FEATURE:
<223> OTHER INFORMATION: Synthetic Primer

<400> SEQUENCE: 15
aagtcctagc cagtctccag a                                                21

<210> SEQ ID NO 16
<211> LENGTH: 21
<212> TYPE: DNA
<213> ORGANISM: Artificial Sequence
<220> FEATURE:
<223> OTHER INFORMATION: Synthetic Primer

<400> SEQUENCE: 16
gagctgtctc tgggccattt c                                                21

<210> SEQ ID NO 17
```

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
gtgccaaggg cctgaatgag                                                 20

<210> SEQ ID NO 18
<211> LENGTH: 19
<212> TYPE: DNA
<213> ORGANISM: Artificial Sequence
<220> FEATURE:
<223> OTHER INFORMATION: Synthetic Primer

<400> SEQUENCE: 18
gcaaaggctc caggtctga                                                  19

<210> SEQ ID NO 19
<211> LENGTH: 22
<212> TYPE: DNA
<213> ORGANISM: Artificial Sequence
<220> FEATURE:
<223> OTHER INFORMATION: Synthetic Primer

<400> SEQUENCE: 19
atgtgcgacg aagacgagac ca                                              22

<210> SEQ ID NO 20
<211> LENGTH: 21
<212> TYPE: DNA
<213> ORGANISM: Artificial Sequence
<220> FEATURE:
<223> OTHER INFORMATION: Synthetic Primer

<400> SEQUENCE: 20
agggtcagga tacctcgctt g                                               21

<210> SEQ ID NO 21
<211> LENGTH: 21
<212> TYPE: DNA
<213> ORGANISM: Artificial Sequence
<220> FEATURE:
<223> OTHER INFORMATION: Synthetic Primer

<400> SEQUENCE: 21
ctcctcccac atgatgctga c                                               21

<210> SEQ ID NO 22
<211> LENGTH: 19
<212> TYPE: DNA
<213> ORGANISM: Artificial Sequence
<220> FEATURE:
<223> OTHER INFORMATION: Synthetic Primer

<400> SEQUENCE: 22
aattgctcgc ggcatacct                                                  19

<210> SEQ ID NO 23
<211> LENGTH: 24
<212> TYPE: DNA
<213> ORGANISM: Artificial Sequence
<220> FEATURE:
<223> OTHER INFORMATION: Synthetic Primer

<400> SEQUENCE: 23
```

```
catcactcct attctgccta gcaa                                          24
```

<210> SEQ ID NO 24
<211> LENGTH: 23
<212> TYPE: DNA
<213> ORGANISM: Artificial Sequence
<220> FEATURE:
<223> OTHER INFORMATION: Synthetic Primer

<400> SEQUENCE: 24

```
tcctcgggcc atgattatag tac                                           23
```

<210> SEQ ID NO 25
<211> LENGTH: 19
<212> TYPE: DNA
<213> ORGANISM: Artificial Sequence
<220> FEATURE:
<223> OTHER INFORMATION: Synthetic Primer

<400> SEQUENCE: 25

```
gccaccttga cccgattct                                                19
```

<210> SEQ ID NO 26
<211> LENGTH: 19
<212> TYPE: DNA
<213> ORGANISM: Artificial Sequence
<220> FEATURE:
<223> OTHER INFORMATION: Synthetic Primer

<400> SEQUENCE: 26

```
ttgctagggc cgcgataat                                                19
```

<210> SEQ ID NO 27
<211> LENGTH: 24
<212> TYPE: DNA
<213> ORGANISM: Artificial Sequence
<220> FEATURE:
<223> OTHER INFORMATION: Synthetic Primer

<400> SEQUENCE: 27

```
cggaagtatt tttctttgca ggat                                          24
```

<210> SEQ ID NO 28
<211> LENGTH: 22
<212> TYPE: DNA
<213> ORGANISM: Artificial Sequence
<220> FEATURE:
<223> OTHER INFORMATION: Synthetic Primer

<400> SEQUENCE: 28

```
cagcagcctc ctagatcatg tg                                            22
```

<210> SEQ ID NO 29
<211> LENGTH: 29
<212> TYPE: DNA
<213> ORGANISM: Artificial Sequence
<220> FEATURE:
<223> OTHER INFORMATION: Synthetic Primer

<400> SEQUENCE: 29

```
agaagtccca tacacaaccg cagtcgcaa                                     29
```

<210> SEQ ID NO 30
<211> LENGTH: 29
<212> TYPE: DNA

```
<213> ORGANISM: Artificial Sequence
<220> FEATURE:
<223> OTHER INFORMATION: Synthetic Primer

<400> SEQUENCE: 30
cttggagctg ttttctggtg ctgcaagga                                        29

<210> SEQ ID NO 31
<211> LENGTH: 19
<212> TYPE: DNA
<213> ORGANISM: Artificial Sequence
<220> FEATURE:
<223> OTHER INFORMATION: Synthetic Primer

<400> SEQUENCE: 31
gctctggtag gggcagtga                                                   19

<210> SEQ ID NO 32
<211> LENGTH: 21
<212> TYPE: DNA
<213> ORGANISM: Artificial Sequence
<220> FEATURE:
<223> OTHER INFORMATION: Synthetic Primer

<400> SEQUENCE: 32
tcctgtaaaa gcccggagta t                                                21

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer

<400> SEQUENCE: 33
tacagccaac gctacttcct                                                  20

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer

<400> SEQUENCE: 34
gggacttcat gccatctaaa                                                  20

<210> SEQ ID NO 35
<211> LENGTH: 23
<212> TYPE: DNA
<213> ORGANISM: Artificial Sequence
<220> FEATURE:
<223> OTHER INFORMATION: Synthetic Primer

<400> SEQUENCE: 35
tgatgaatgc accottgtac ttg                                              23

<210> SEQ ID NO 36
<211> LENGTH: 17
<212> TYPE: DNA
<213> ORGANISM: Artificial Sequence
<220> FEATURE:
<223> OTHER INFORMATION: Synthetic Primer

<400> SEQUENCE: 36
tccccagtga aagtgga                                                     17
```

<210> SEQ ID NO 37
<211> LENGTH: 20
<212> TYPE: DNA
<213> ORGANISM: Artificial Sequence
<220> FEATURE:
<223> OTHER INFORMATION: Synthetic Primer

<400> SEQUENCE: 37
tggtcttcgc cacctacttg                                       20

<210> SEQ ID NO 38
<211> LENGTH: 20
<212> TYPE: DNA
<213> ORGANISM: Artificial Sequence
<220> FEATURE:
<223> OTHER INFORMATION: Synthetic Primer

<400> SEQUENCE: 38
aagccgagca aaatgatgag                                       20

<210> SEQ ID NO 39
<211> LENGTH: 20
<212> TYPE: DNA
<213> ORGANISM: Artificial Sequence
<220> FEATURE:
<223> OTHER INFORMATION: Synthetic Primer

<400> SEQUENCE: 39
caggggctac tcctttttcc                                       20

<210> SEQ ID NO 40
<211> LENGTH: 20
<212> TYPE: DNA
<213> ORGANISM: Artificial Sequence
<220> FEATURE:
<223> OTHER INFORMATION: Synthetic Primer

<400> SEQUENCE: 40
cccagacctg cacttctttt                                       20

<210> SEQ ID NO 41
<211> LENGTH: 22
<212> TYPE: DNA
<213> ORGANISM: Artificial Sequence
<220> FEATURE:
<223> OTHER INFORMATION: Synthetic Primer

<400> SEQUENCE: 41
aagaaaagaa gtgcaggtct gg                                    22

<210> SEQ ID NO 42
<211> LENGTH: 20
<212> TYPE: DNA
<213> ORGANISM: Artificial Sequence
<220> FEATURE:
<223> OTHER INFORMATION: Synthetic Primer

<400> SEQUENCE: 42
agagcaggaa gcagaaatgg                                       20

<210> SEQ ID NO 43
<211> LENGTH: 20
<212> TYPE: DNA
<213> ORGANISM: Artificial Sequence
<220> FEATURE:

-continued

<223> OTHER INFORMATION: Synthetic Primer

<400> SEQUENCE: 43
tgtgtcctca agagcagtcg                                               20

<210> SEQ ID NO 44
<211> LENGTH: 19
<212> TYPE: DNA
<213> ORGANISM: Artificial Sequence
<220> FEATURE:
<223> OTHER INFORMATION: Synthetic Primer

<400> SEQUENCE: 44
caactctggt tggacaggt                                                19

<210> SEQ ID NO 45
<211> LENGTH: 18
<212> TYPE: DNA
<213> ORGANISM: Artificial Sequence
<220> FEATURE:
<223> OTHER INFORMATION: Synthetic Primer

<400> SEQUENCE: 45
gcctgtctgt cgggatgt                                                 18

<210> SEQ ID NO 46
<211> LENGTH: 19
<212> TYPE: DNA
<213> ORGANISM: Artificial Sequence
<220> FEATURE:
<223> OTHER INFORMATION: Synthetic Primer

<400> SEQUENCE: 46
ggcttcgtgg attctcttg                                                19

<210> SEQ ID NO 47
<211> LENGTH: 18
<212> TYPE: DNA
<213> ORGANISM: Artificial Sequence
<220> FEATURE:
<223> OTHER INFORMATION: Synthetic Primer

<400> SEQUENCE: 47
ccgctgccag tactgtcg                                                 18

<210> SEQ ID NO 48
<211> LENGTH: 20
<212> TYPE: DNA
<213> ORGANISM: Artificial Sequence
<220> FEATURE:
<223> OTHER INFORMATION: Synthetic Primer

<400> SEQUENCE: 48
acctggtcct ccaaggtgag                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic Primer

<400> SEQUENCE: 49
cgctttctgc gtatcgtctg                                               20

```
<210> SEQ ID NO 50
<211> LENGTH: 19
<212> TYPE: DNA
<213> ORGANISM: Artificial Sequence
<220> FEATURE:
<223> OTHER INFORMATION: Synthetic Primer

<400> SEQUENCE: 50
gatgcacggg atcgtgtct                                                 19

<210> SEQ ID NO 51
<211> LENGTH: 21
<212> TYPE: DNA
<213> ORGANISM: Artificial Sequence
<220> FEATURE:
<223> OTHER INFORMATION: Synthetic Primer

<400> SEQUENCE: 51
cttgtgtggc aaacgatgat g                                              21

<210> SEQ ID NO 52
<211> LENGTH: 23
<212> TYPE: DNA
<213> ORGANISM: Artificial Sequence
<220> FEATURE:
<223> OTHER INFORMATION: Synthetic Primer

<400> SEQUENCE: 52
tggtgtcctt gtcatatgtt ctg                                            23

<210> SEQ ID NO 53
<211> LENGTH: 20
<212> TYPE: DNA
<213> ORGANISM: Artificial Sequence
<220> FEATURE:
<223> OTHER INFORMATION: Synthetic Primer

<400> SEQUENCE: 53
cgtcctggac aagaccaagt                                                20

<210> SEQ ID NO 54
<211> LENGTH: 20
<212> TYPE: DNA
<213> ORGANISM: Artificial Sequence
<220> FEATURE:
<223> OTHER INFORMATION: Synthetic Primer

<400> SEQUENCE: 54
attgctgtcc cgaatgtctc                                                20

<210> SEQ ID NO 55
<211> LENGTH: 20
<212> TYPE: DNA
<213> ORGANISM: Artificial Sequence
<220> FEATURE:
<223> OTHER INFORMATION: Synthetic Primer

<400> SEQUENCE: 55
tgtcctggat aagaccaagt                                                20

<210> SEQ ID NO 56
<211> LENGTH: 20
<212> TYPE: DNA
<213> ORGANISM: Artificial Sequence
<220> FEATURE:
<223> OTHER INFORMATION: Synthetic Primer
```

<400> SEQUENCE: 56
ttcatccttc tcctgttcat 20

<210> SEQ ID NO 57
<211> LENGTH: 24
<212> TYPE: DNA
<213> ORGANISM: Artificial Sequence
<220> FEATURE:
<223> OTHER INFORMATION: Synthetic Primer

<400> SEQUENCE: 57
ccttctatgc tgcttttggg aacc 24

<210> SEQ ID NO 58
<211> LENGTH: 22
<212> TYPE: DNA
<213> ORGANISM: Artificial Sequence
<220> FEATURE:
<223> OTHER INFORMATION: Synthetic Primer

<400> SEQUENCE: 58
gtgatcgacc acttcgcaga gc 22

<210> SEQ ID NO 59
<211> LENGTH: 20
<212> TYPE: DNA
<213> ORGANISM: Artificial Sequence
<220> FEATURE:
<223> OTHER INFORMATION: Synthetic Primer

<400> SEQUENCE: 59
taaagcggca gctggagtat 20

<210> SEQ ID NO 60
<211> LENGTH: 20
<212> TYPE: DNA
<213> ORGANISM: Artificial Sequence
<220> FEATURE:
<223> OTHER INFORMATION: Synthetic Primer

<400> SEQUENCE: 60
actgggaggc atagcactgt 20

<210> SEQ ID NO 61
<211> LENGTH: 21
<212> TYPE: DNA
<213> ORGANISM: Artificial Sequence
<220> FEATURE:
<223> OTHER INFORMATION: Synthetic Primer

<400> SEQUENCE: 61
gcttatgggc ttctccaaac t 21

<210> SEQ ID NO 62
<211> LENGTH: 21
<212> TYPE: DNA
<213> ORGANISM: Artificial Sequence
<220> FEATURE:
<223> OTHER INFORMATION: Synthetic Primer

<400> SEQUENCE: 62
ggtgacacct ctcccacata c 21

<210> SEQ ID NO 63
<211> LENGTH: 19

```
<212> TYPE: DNA
<213> ORGANISM: Artificial Sequence
<220> FEATURE:
<223> OTHER INFORMATION: Synthetic Primer

<400> SEQUENCE: 63
tcacgggttt ctcctacgc                                                19

<210> SEQ ID NO 64
<211> LENGTH: 19
<212> TYPE: DNA
<213> ORGANISM: Artificial Sequence
<220> FEATURE:
<223> OTHER INFORMATION: Synthetic Primer

<400> SEQUENCE: 64
gccaaagcgg ttcacacac                                                19

<210> SEQ ID NO 65
<211> LENGTH: 20
<212> TYPE: DNA
<213> ORGANISM: Artificial Sequence
<220> FEATURE:
<223> OTHER INFORMATION: Synthetic Primer

<400> SEQUENCE: 65
gctactcaac cagcactcct                                               20

<210> SEQ ID NO 66
<211> LENGTH: 18
<212> TYPE: DNA
<213> ORGANISM: Artificial Sequence
<220> FEATURE:
<223> OTHER INFORMATION: Synthetic Primer

<400> SEQUENCE: 66
cctggtgatt tcgcattt                                                 18

<210> SEQ ID NO 67
<211> LENGTH: 22
<212> TYPE: DNA
<213> ORGANISM: Artificial Sequence
<220> FEATURE:
<223> OTHER INFORMATION: Synthetic Primer

<400> SEQUENCE: 67
atggtggagg ttgagaatgt ag                                            22

<210> SEQ ID NO 68
<211> LENGTH: 22
<212> TYPE: DNA
<213> ORGANISM: Artificial Sequence
<220> FEATURE:
<223> OTHER INFORMATION: Synthetic Primer

<400> SEQUENCE: 68
tggtctcttc cagaacatct tg                                            22

<210> SEQ ID NO 69
<211> LENGTH: 20
<212> TYPE: DNA
<213> ORGANISM: Artificial Sequence
<220> FEATURE:
<223> OTHER INFORMATION: Synthetic Primer

<400> SEQUENCE: 69
```
ggcgtctgac aacttccact                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic Primer

<400> SEQUENCE: 70
aacacccaag gaccatgcta                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic Primer

<400> SEQUENCE: 71
aggctcccca gaacaagatt                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic Primer

<400> SEQUENCE: 72 tctcgcccctt gagtttgtct                                             20

<210> SEQ ID NO 73
<211> LENGTH: 26
<212> TYPE: DNA
<213> ORGANISM: Artificial Sequence
<220> FEATURE:
<223> OTHER INFORMATION: Synthetic Primer

<400> SEQUENCE: 73
cctggtggac atcttccagg agtacc                                       26

<210> SEQ ID NO 74
<211> LENGTH: 26
<212> TYPE: DNA
<213> ORGANISM: Artificial Sequence
<220> FEATURE:
<223> OTHER INFORMATION: Synthetic Primer

<400> SEQUENCE: 74
gaagctcatc tctcctatgt gctggc                                       26

<210> SEQ ID NO 75
<211> LENGTH: 19
<212> TYPE: DNA
<213> ORGANISM: Artificial Sequence
<220> FEATURE:
<223> OTHER INFORMATION: Synthetic Primer

<400> SEQUENCE: 75
cattttgctg tctgccatg                                               19

<210> SEQ ID NO 76
<211> LENGTH: 20
<212> TYPE: DNA
<213> ORGANISM: Artificial Sequence

```
<220> FEATURE:
<223> OTHER INFORMATION: Synthetic Primer

<400> SEQUENCE: 76
ccatgccaat gacactcttg                                                   20

<210> SEQ ID NO 77
<211> LENGTH: 21
<212> TYPE: DNA
<213> ORGANISM: Artificial Sequence
<220> FEATURE:
<223> OTHER INFORMATION: Synthetic Primer

<400> SEQUENCE: 77
tgatcgcctg cttattcacg g                                                 21

<210> SEQ ID NO 78
<211> LENGTH: 21
<212> TYPE: DNA
<213> ORGANISM: Artificial Sequence
<220> FEATURE:
<223> OTHER INFORMATION: Synthetic Primer

<400> SEQUENCE: 78
aaccgcctag aaatctccag a                                                 21

<210> SEQ ID NO 79
<211> LENGTH: 21
<212> TYPE: DNA
<213> ORGANISM: Artificial Sequence
<220> FEATURE:
<223> OTHER INFORMATION: Synthetic Primer

<400> SEQUENCE: 79
gccaaagtga aagagtttgg a                                                 21

<210> SEQ ID NO 80
<211> LENGTH: 20
<212> TYPE: DNA
<213> ORGANISM: Artificial Sequence
<220> FEATURE:
<223> OTHER INFORMATION: Synthetic Primer

<400> SEQUENCE: 80
atggaaagtc caatggctga                                                   20

<210> SEQ ID NO 81
<211> LENGTH: 22
<212> TYPE: DNA
<213> ORGANISM: Artificial Sequence
<220> FEATURE:
<223> OTHER INFORMATION: Synthetic Primer

<400> SEQUENCE: 81
ctgctggtga ttggtggctt tg                                                22

<210> SEQ ID NO 82
<211> LENGTH: 21
<212> TYPE: DNA
<213> ORGANISM: Artificial Sequence
<220> FEATURE:
<223> OTHER INFORMATION: Synthetic Primer

<400> SEQUENCE: 82
ttgctgatgg tggctgggat g                                                 21
```

<210> SEQ ID NO 83
<211> LENGTH: 20
<212> TYPE: DNA
<213> ORGANISM: Artificial Sequence
<220> FEATURE:
<223> OTHER INFORMATION: Synthetic Primer

<400> SEQUENCE: 83
gtgggaagaa ggagaacctg                                          20

<210> SEQ ID NO 84
<211> LENGTH: 20
<212> TYPE: DNA
<213> ORGANISM: Artificial Sequence
<220> FEATURE:
<223> OTHER INFORMATION: Synthetic Primer

<400> SEQUENCE: 84
ctggagtgtt gatggagcag                                          20

<210> SEQ ID NO 85
<211> LENGTH: 21
<212> TYPE: DNA
<213> ORGANISM: Artificial Sequence
<220> FEATURE:
<223> OTHER INFORMATION: Synthetic Primer

<400> SEQUENCE: 85
ccaggaagtt cttcgttggg g                                        21

<210> SEQ ID NO 86
<211> LENGTH: 21
<212> TYPE: DNA
<213> ORGANISM: Artificial Sequence
<220> FEATURE:
<223> OTHER INFORMATION: Synthetic Primer

<400> SEQUENCE: 86
caaagtcgat gtaagcggtg g                                        21

<210> SEQ ID NO 87
<211> LENGTH: 20
<212> TYPE: DNA
<213> ORGANISM: Artificial Sequence
<220> FEATURE:
<223> OTHER INFORMATION: Synthetic Primer

<400> SEQUENCE: 87
catggccttc cgtgttccta                                          20

<210> SEQ ID NO 88
<211> LENGTH: 17
<212> TYPE: DNA
<213> ORGANISM: Artificial Sequence
<220> FEATURE:
<223> OTHER INFORMATION: Synthetic Primer

<400> SEQUENCE: 88
gcggcacgtc agatcca                                             17

<210> SEQ ID NO 89
<211> LENGTH: 22
<212> TYPE: DNA
<213> ORGANISM: Artificial Sequence
<220> FEATURE:
<223> OTHER INFORMATION: Synthetic Primer

```
<400> SEQUENCE: 89
ctccgctttc atgtagagga ag                                              22

<210> SEQ ID NO 90
<211> LENGTH: 23
<212> TYPE: DNA
<213> ORGANISM: Artificial Sequence
<220> FEATURE:
<223> OTHER INFORMATION: Synthetic Primer

<400> SEQUENCE: 90
gacatctcct agtttggaca gtg                                             23

<210> SEQ ID NO 91
<211> LENGTH: 21
<212> TYPE: DNA
<213> ORGANISM: Artificial Sequence
<220> FEATURE:
<223> OTHER INFORMATION: Synthetic Primer

<400> SEQUENCE: 91
ctgtgcagaa gagagcaatc c                                               21

<210> SEQ ID NO 92
<211> LENGTH: 20
<212> TYPE: DNA
<213> ORGANISM: Artificial Sequence
<220> FEATURE:
<223> OTHER INFORMATION: Synthetic Primer

<400> SEQUENCE: 92
ctgtcagacc gccatagtgt                                                 20

<210> SEQ ID NO 93
<211> LENGTH: 19
<212> TYPE: DNA
<213> ORGANISM: Artificial Sequence
<220> FEATURE:
<223> OTHER INFORMATION: Synthetic Primer

<400> SEQUENCE: 93
tgcgtccact ggcatctac                                                  19

<210> SEQ ID NO 94
<211> LENGTH: 22
<212> TYPE: DNA
<213> ORGANISM: Artificial Sequence
<220> FEATURE:
<223> OTHER INFORMATION: Synthetic Primer

<400> SEQUENCE: 94
cagagcaggc gcaatagttt ta                                              22

<210> SEQ ID NO 95
<211> LENGTH: 20
<212> TYPE: DNA
<213> ORGANISM: Artificial Sequence
<220> FEATURE:
<223> OTHER INFORMATION: Synthetic Primer

<400> SEQUENCE: 95
tgtctggaga aacagccaag                                                 20

<210> SEQ ID NO 96
```

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 96
tcctcgaata gctgcaagtg                                          20

<210> SEQ ID NO 97
<211> LENGTH: 23
<212> TYPE: DNA
<213> ORGANISM: Artificial Sequence
<220> FEATURE:
<223> OTHER INFORMATION: Synthetic Primer

<400> SEQUENCE: 97
gaagaatgtg ggggagagtg tgg                                      23

<210> SEQ ID NO 98
<211> LENGTH: 22
<212> TYPE: DNA
<213> ORGANISM: Artificial Sequence
<220> FEATURE:
<223> OTHER INFORMATION: Synthetic Primer

<400> SEQUENCE: 98
tgcctgtgct ggaactttct gg                                       22

<210> SEQ ID NO 99
<211> LENGTH: 23
<212> TYPE: DNA
<213> ORGANISM: Artificial Sequence
<220> FEATURE:
<223> OTHER INFORMATION: Synthetic Primer

<400> SEQUENCE: 99
aggcatatgg gcatagggaa gag                                      23

<210> SEQ ID NO 100
<211> LENGTH: 23
<212> TYPE: DNA
<213> ORGANISM: Artificial Sequence
<220> FEATURE:
<223> OTHER INFORMATION: Synthetic Primer

<400> SEQUENCE: 100
ttgaccttca ggtacaggct gtg                                      23

<210> SEQ ID NO 101
<211> LENGTH: 20
<212> TYPE: DNA
<213> ORGANISM: Artificial Sequence
<220> FEATURE:
<223> OTHER INFORMATION: Synthetic Primer

<400> SEQUENCE: 101
cctagtgctg catgaggaga                                          20

<210> SEQ ID NO 102
<211> LENGTH: 23
<212> TYPE: DNA
<213> ORGANISM: Artificial Sequence
<220> FEATURE:
<223> OTHER INFORMATION: Synthetic Primer

<400> SEQUENCE: 102
```
tcttcctcat cttcttgctc ttc					23

<210> SEQ ID NO 103
<211> LENGTH: 22
<212> TYPE: DNA
<213> ORGANISM: Artificial Sequence
<220> FEATURE:
<223> OTHER INFORMATION: Synthetic Primer

<400> SEQUENCE: 103
caagtgacct ctctgtttaa gg					22

<210> SEQ ID NO 104
<211> LENGTH: 19
<212> TYPE: DNA
<213> ORGANISM: Artificial Sequence
<220> FEATURE:
<223> OTHER INFORMATION: Synthetic Primer

<400> SEQUENCE: 104
gcctgctcca tcttgattt					19

<210> SEQ ID NO 105
<211> LENGTH: 22
<212> TYPE: DNA
<213> ORGANISM: Artificial Sequence
<220> FEATURE:
<223> OTHER INFORMATION: Synthetic Primer

<400> SEQUENCE: 105
gagcttcctg aacagcgaag tg					22

<210> SEQ ID NO 106
<211> LENGTH: 22
<212> TYPE: DNA
<213> ORGANISM: Artificial Sequence
<220> FEATURE:
<223> OTHER INFORMATION: Synthetic Primer

<400> SEQUENCE: 106
tggccacctc cagatagtca tc					22

<210> SEQ ID NO 107
<211> LENGTH: 19
<212> TYPE: DNA
<213> ORGANISM: Artificial Sequence
<220> FEATURE:
<223> OTHER INFORMATION: Synthetic Primer

<400> SEQUENCE: 107
gactcagctg ccatgactg					19

<210> SEQ ID NO 108
<211> LENGTH: 21
<212> TYPE: DNA
<213> ORGANISM: Artificial Sequence
<220> FEATURE:
<223> OTHER INFORMATION: Synthetic Primer

<400> SEQUENCE: 108
gcgacagagc cagaataaca g					21

<210> SEQ ID NO 109
<211> LENGTH: 20
<212> TYPE: DNA

```
<213> ORGANISM: Artificial Sequence
<220> FEATURE:
<223> OTHER INFORMATION: Synthetic Primer

<400> SEQUENCE: 109
tccaaatcct gggtgtcaaa                                           20

<210> SEQ ID NO 110
<211> LENGTH: 20
<212> TYPE: DNA
<213> ORGANISM: Artificial Sequence
<220> FEATURE:
<223> OTHER INFORMATION: Synthetic Primer

<400> SEQUENCE: 110
cagcagcagt tctctgaagc                                           20
```

METHOD OF TREATING HEART FAILURE

CROSS REFERENCE TO RELATED APPLICATIONS

This patent application is a U.S. National Phase of International Patent Application No. PCT/US2016/017371, filed Feb. 10, 2016, which claims priority to U.S. Provisional Application No. 62/216,698, filed Sep. 10, 2015, U.S. Provisional Application No. 62/215,502, filed Sep. 8, 2015, and U.S. Provisional Application No. 62/114,501, filed Feb. 10, 2015, all of which are incorporated herein by reference in their entirety.

STATEMENT OF GOVERNMENT INTEREST

This invention was made with government support under contract number R01 DK089705 awarded by the National Institutes of Health. The government has certain rights in the invention.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 21,165 Byte ASCII (Text) file named "730296ReplacementSequenceListing" created on Nov. 17, 2017.

TECHNICAL FIELD

The present invention relates to methods for treating heart failure.

BACKGROUND

Iron is required for oxygen transport, oxidative phosphorylation, DNA synthesis, and other cellular processes. Iron co-factors, for example, iron-sulfur (Fe—S) clusters and heme, are synthesized by mitochondria and needed for mitochondrial function. Mitochondria supply energy for cells, including the energy needed by cardiomyocytes for repeated heart muscle contraction. Accordingly, the maintenance of mitochondria, including the removal of dysfunctional mitochondria through mitophagy and synthesis of iron co-factors, is needed for cardiomyocyte function.

Improper cardiomyocyte function may lead to heart failure. Heart failure may be further complicated by the presence of iron deficiency. Up to 50% of patients with heart failure have iron deficiency, which is associated with poor outcomes despite current therapies.

Accordingly, a need exists for the identification and development of new therapies for heart failure.

SUMMARY

The present invention relates to a method for treating heart failure in a subject in need thereof. The method may comprise administering a therapeutically effective amount of nicotinamide riboside to the subject.

The present invention also relates to a method for treating heart failure in a subject in need thereof. The method may comprise administering a therapeutically effective amount of nicotinamide riboside and a therapeutically effective amount of iron to the subject.

The present invention further relates to a method for treating heart failure associated with iron deficiency in a subject in need thereof. The method may comprise administering a therapeutically effective amount of nicotinamide riboside to the subject.

The present invention also relates to a method for treating heart failure associated with iron deficiency in a subject in need thereof. The method may comprise administering a therapeutically effective amount of nicotinamide riboside and a therapeutically effective amount of iron to the subject.

The present invention further relates to a method of identifying a subject suffering from heart failure as a candidate for treatment with nicotinamide riboside. The method may comprise (a) measuring in a sample obtained from the subject a level selected from the group consisting of: (i) a level of a ratio of NAD/NADH; (ii) a level of iron; (iii) a level of FGF21 protein; (iv) a level of Angiopoietin-like 4 (AngPtL4) protein; and (v) any combination thereof. The method may also comprise (b) comparing the measured level to a control level; and (c) identifying the subject as a candidate for treatment with nicotinamide riboside if (i) the measured level of the ratio of NAD/NADH is lower than the control level of the ratio of NAD/NADH; (ii) the measured level of iron is lower than the control level of iron; (iii) the measured level of FGF21 protein is higher than the control level of FGF21 protein; (iv) the measured level of AngPtL4 protein is higher than the control level of AngPtL4 protein; or (v) any combination thereof.

BRIEF DESCRIPTION OF THE DRAWINGS

(E) Relative mRNA levels of PGC1-a (Ppargc1a) and PGC1-B (Ppargc1b). (F) Relative mRNA levels of PPARa (Ppara), Rxr gamma (Rxrg), and fatty acid transport protein (Fatp1). Data were presented as means±SEM. Sample size (n) was indicated

DETAILED DESCRIPTION

Figure 1A:
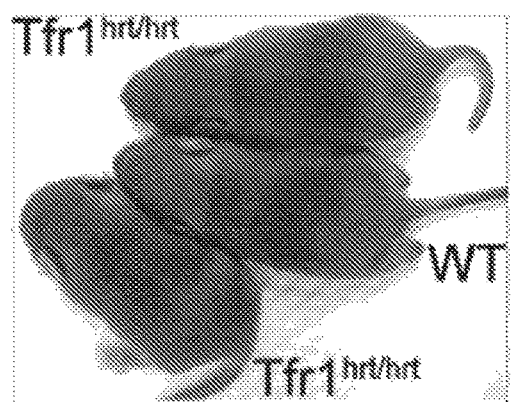
FIG. 1 shows that loss of Tfr1 in cardiomyocytes caused cardiomyopathy. (A) Tfr1$^{hrt/hrt}$ mice appeared similar to wild-type (WT) at P10. (B) H&E staining of heart sections at P10 demonstrated cardiomegaly in Tfr$^{hrt/hrt}$ mice. Scale bars=1 mm. (C) Tfr1$^{hrt/hrt}$ mice had increased heart to body weight ratios at P10. (D) Echocardiograms from representative Tfr1$^{hrt/hrt}$ and WT littermates at P10. Upper panel, short axis; lower panel, long axis. Tfr1$^{hrt/hrt}$ mice had markedly impaired cardiac function. (E) Left ventricular diameter and fractional shortening were abnormal in Tfr1$^{hrt/hrt}$ mice. LVDd=left ventricular diameter in diastole; LVDs=left ventricular diameter in systole. (F) Representative images of WGA staining for cardiomyocyte morphometrics and quantitation showing larger cardiomyocyte area in Tfr1$^{hrt/hrt}$ mice. Scale bars=15 μm. (G) mRNA levels of cardiac hypertrophy biomarkers as described in the Examples. Data were presented as means±standard error of the mean (SEM). Sample size (n) was indicated. *p<0.05; p<0.01; *p<0.001 by one-way ANOVA. See FIG. 8.

The present invention relates to a method for treating heart failure in a subject in need thereof. The heart failure may be associated with iron deficiency. The method includes administering nicotinamide riboside to the subject. Nicotinamide riboside is acted upon in the subject to induce the production of NAD, which in turn, increases the lifespan of the subject. The lifespan of the subject may be increased as compared to a lifespan of a subject suffering from heart failure and not administered nicotinamide riboside.

Nicotinamide riboside may also enhance or increase the mitochondrial unfolded-protein response, and thus, the method may enhance or increase the mitochondrial unfolded-protein response in the subject as compared to a mitochondrial unfolded-protein response in a subject suffering from heart failure and not administered nicotinamide riboside. Alternatively, nicotinamide riboside may inhibit or decrease the mitochondrial unfolded-protein response, and thus, the method may inhibit or decrease the mitochondrial unfolded-protein response in the subject as compared to a mitochondrial unfolded-protein response in a subject suffering from heart failure and not administered nicotinamide riboside.

The method may also include administering iron to the subject and thus, provides a combination therapy of nicotinamide riboside and iron for the subject suffering from heart failure.

The present invention also relates to a method of identifying a subject suffering from heart failure as a candidate for treatment with nicotinamide riboside.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Heart failure" as used herein refers to a chronic, progressive condition in which the heart muscle is unable to pump enough blood to meet the subject's needs for blood and oxygen. Heart failure is a clinical disorder characterized by congestion and decreased functional capacity. In some embodiments, the heart failure may be characterized by or associated with iron deficiency. Heart failure may include the left side, right side, or both sides of the heart. Accordingly, in some embodiments, heart failure may be left-sided heart failure (systolic failure or diastolic failure), right-sided heart failure, congestive heart failure, or any combination thereof. The heart failure may be classified by the New York Heart Association (NYHA) Functional Classification system. The NYHA Functional Classification system may include a functional capacity, which is a description of how the subject feels during physical activity, and an objective assessment. Functional capacity is ranked from class I to class IV, with increasing limitations of physical activity. Objective assessment is ranked from class A to class D, with increasing severity.

"Iron deficiency," "Sideropenia," and "Hypoferremia" as used herein may be used interchangeably to describe a condition in which a subject has a less than normal supply of iron. A normal Total Iron Binding Capacity (TIBC) test should range from 240 mcg/dL to 450 mcg/dL, resulting in a normal transferrin saturation range of 20 percent to 50 percent.

Iron deficiency may be accompanied with anemia, but need not be accompanied by anemia. Iron deficiency may exacerbate heart failure even when anemia is not present in the subject. In some embodiments, a subject suffering from heart failure may be considered iron deficient if ferritin is less than 100 µg/L, iron is less than 6 µmol/L, transferrin is less than 25 µmol/L, or transferrin saturation is less than 20%.

In some embodiments, the presence or absence of iron deficiency in the subject may be determined by examining red blood cells from the subject for characteristics of iron deficiency. In other embodiments, the presence or absence of iron deficiency in the subject may be determined by measuring the ratio of serum iron:total iron-binding capacity, this ratio is a dynamic measurement of how much iron is available to the tissues of the subject. In still other embodiments, the presence or absence of iron deficiency in the subject may be determined by measuring the level of serum ferritin in a sample obtained from the subject.

"Sample," "test sample," "specimen," "sample from a subject," and "patient sample" as used herein may be used interchangeably and may be a sample of blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, bronchoalveolar lavage (BAL) fluid, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Treat", "treating" or "treatment" are each used interchangeably herein to describe reversing, alleviating, or inhibiting the progress of a condition or disease, or one or more symptoms of such condition or disease, to which such term applies. Depending on the subject, the term also refers to preventing a condition or disease, and includes preventing the onset of a condition or disease, or preventing the symptoms associated with a condition or disease. A treatment may be either performed in an acute or chronic way. The term also refers to reducing the severity of a condition or disease, or symptoms associated with such condition or disease prior to affliction with the condition or disease. Such prevention or reduction of the severity of a condition or disease prior to affliction refers to administration of nicotinamide riboside with or without iron, or a pharmaceutical composition of the present invention to a subject that is not at the time of administration afflicted with the condition or disease. "Preventing" also refers to preventing the recurrence of a condition or disease or of one or more symptoms associated with such condition or disease. "Treatment" and "therapeutically," refer to the act of treating, as "treating" is defined above.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Method of Treatment

Provided herein is a method of treating heart failure in a subject in need thereof. The heart failure may be associated with iron deficiency. The method may include administering nicotinamide riboside (NR) to the subject. The method may further comprise administering iron to the subject.

The subject may have iron deficiency. The subject may have iron deficiency in the heart. The subject may have iron deficiency with anemia. The subject may have iron deficiency without anemia.

The subject may have dysfunctional mitochondria. The subject may have dysfunctional mitochondria in the heart. The dysfunctional mitochondria may be caused by iron deficiency in the subject. In turn, the dysfunctional mitochondria may cause a reduced NAD/NADH ratio in the subject.

The subject may have reduced mitophagy. The subject may have dysfunctional mitophagy. The subject may have dysfunctional mitophagy in the heart. The dysfunctional mitophagy may be caused by iron deficiency in the subject, but may also exacerbate the iron deficiency in the subject because iron may not be recovered from dysfunctional mitochondria.

The subject may have a decreased NAD/NADH ratio as compared to a NAD/NADH ratio of a subject not suffering from heart failure. In some embodiments, the subject may have a decreased NAD/NADH ratio in the heart as compared to a NAD/NADH ratio in the heart of the subject not suffering from heart failure.

In some embodiments, the subject may have a decreased NAD/NADH ratio as compared to a NAD/NADH ratio of a subject not suffering from heart failure associated with iron deficiency. In other embodiments, the subject may have a decreased NAD/NADH ratio in the heart as compared to a NAD/NADH ratio in the heart of the subject not suffering from heart failure associated with iron deficiency.

The method may enhance or increase the mitochondrial unfolded-protein response in the subject. The method may enhance or increase the mitochondrial unfolded-protein response in the heart of the subject. The method may enhance or increase the mitochondrial unfolded-protein response in the subject as compared to a mitochondrial unfolded-protein response in a subject suffering from heart failure and not administered nicotinamide riboside. The enhanced or increased mitochondrial unfolded-protein response may correlate with an increase in expression of one or more $UPR^{MT}$ mRNAs. The method may inhibit or decrease the mitochondrial unfolded-protein response in the heart of the subject. The method may inhibit or decrease the mitochondrial unfolded-protein response in the subject as compared to a mitochondrial unfolded-protein response in a subject suffering from heart failure and not administered nicotinamide riboside. The inhibited or decreased mitochondrial unfolded-protein response may correlate with decrease or inhibition of expression of one or more $UPR^{MT}$ mRNAs.

The method may prolong the life span of the subject as compared to a lifespan of a subject suffering from heart failure and not treated with the method described herein. The method may prolong the life span of the subject by up to about 50% as compared to the lifespan of the subject suffering from heart failure and not treated with the method described herein. The method may prolong the life span of the subject by up to about 5% to about 50%, about 10% to about 50%, about 15% to about 50%, about 20% to about 50%, about 25% to about 50%, about 30% to about 50%, about 35% to about 50%, about 40% to about 500, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 15% to about 40%, or about 20% to about 35% as compared to the lifespan of the subject suffering from heart failure and not treated with the method described herein. The method may prolong the lifespan of the subject by up to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 490/%, or 50% as compared to the lifespan of the subject suffering from heart failure and not treated with the method described herein.

The method may extend the lifespan of the subject as compared to the lifespan of the subject suffering from heart failure and not treated with the method described herein. The method may extend the lifespan of the subject by at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, 49 months, 50 months, 51 months, 52 months, 53 months, 54 months, 55 months, 56 months, 57 months, 58 months, 59 months, 60 months, 1 year, 2 years, 3 years, 4 years, or 5 years as compared to the lifespan of the subject suffering from heart failure and not treated with the method described herein.

a. Nicotinamide Riboside

As described above, the method of treating heart failure may include administering nicotinamide riboside to the subject. Nicotinamide riboside is a form of vitamin B3 and may be phosphorylated by Nmrk proteins to induce NAD production. Induction of NAD production may, in turn, increase the NAD/NADH ratio in the subject administered nicotinamide riboside. Administration of nicotinamide riboside may also increase the lifespan of the subject and the mitochondrial unfolded-protein response in the subject as described above. Alternatively, administration of nicotinamide riboside may decrease the mitochondrial unfolded-protein response in the subject as described above.

In some embodiments, the method may administer a therapeutically effective amount of nicotinamide riboside to the subject. The method may administer about 500 mg/day to about 2000 mg/day, about 550 mg/day to about 1900 mg/day, about 600 mg/day to about 1800 mg/day, about 650 mg/day to about 1700 mg/day, about 700 mg/day to about 1600 mg/day, about 750 mg/day to about 1500 mg/day, about 800 mg/day to about 1400 mg/day, about 850 mg/day to about 1300 mg/day, about 900 mg/day to about 1200 mg/day, about 950 mg/day to about 1100 mg/day, about 500 mg/day to about 1900 mg/day, about 500 mg/day to about 1800 mg/day, about 500 mg/day to about 1700 mg/day, about 500 mg/day to about 1600 mg/day, about 500 mg/day to about 1500 mg/day, about 500 mg/day to about 1400 mg/day, about 500 mg/day to about 1300 mg/day, about 500 mg/day to about 1200 mg/day, about 500 mg/day to about 1100 mg/day, about 500 mg/day to about 1000 mg/day, about 500 mg/day to about 950 mg/day, about 500 mg/day to about 900 mg/day, about 500 mg/day to about 850 mg/day, about 500 mg/day to about 800 mg/day, about 500 mg/day to about 750 mg/day, about 500 mg/day to about 700 mg/day, about 500 mg/day to about 650 mg/day, about 500 mg/day to about 600 mg/day, about 550 mg/day to about 2000 mg/day, about 600 mg/day to about 2000 mg/day, about 650 mg/day to about 2000 mg/day, about 700 mg/day to about 2000 mg/day, about 750 mg/day to about 2000 mg/day, about 800 mg/day to about 2000 mg/day, about 850 mg/day to about 2000 mg/day, about 900 mg/day to about 2000 mg/day, about 950 mg/day to about 2000 mg/day, about 1000 mg/day to about 2000 mg/day, about 1100 mg/day to about 2000 mg/day, about 1200 mg/day to about 2000 mg/day, about 1300 mg/day to about 2000 mg/day, about 1400 mg/day to about 2000 mg/day, about 1500 mg/day to about 2000 mg/day, about 1600 mg/day to about 2000 mg/day, about 1700 mg/day to about 2000 mg/day, about 1800 mg/day to about 2000, or about 1900 mg/day to about 2000 mg/day nicotinamide riboside to the subject.

In other embodiments, the method may administer about 500 mg/day, 550 mg/day, 600 mg/day, 650 mg/day, 700 mg/day, 750 mg/day, 800 mg/day, 850 mg/day, 900 mg/day, 950 mg/day, 1000 mg/day, 1100 mg/day, 1200 mg/day, 1300 mg/day, 1400 mg/day, 1500 mg/day, 1600 mg/day, 1700 mg/day, 1800 mg/day, 1900 mg/day, or 2000 mg/day nicotinamide riboside to the subject.

b. Iron

As described above, the treatment method may further administer iron to the subject. The iron may be administered to the subject in a therapeutically effective amount. The iron may be administered to the subject in an amount such that circulating transferrin (Tf) is further saturated with iron. Transferrin is a protein found in the blood and binds and transports iron throughout the bodies of mammals.

The iron administered to the subject may in the form of ferrous sulfate, ferrous fumarate, ferrous gluconate, ferric carboxymaltose, ferric saccharate, ferric gluconate, iron dextran, iron sucrose, or any combination thereof.

The iron may be administered orally to the subject, for example, in tablet form. In some embodiments, the method may administer to the subject an oral daily dose from about 150 mg/day to about 200 mg/day of elemental iron. In other embodiments, the method may administer an oral daily dose from about 100 mg/day to about 300 mg/day or about 125 mg/day to about 250 mg/day of elemental iron. In some embodiments, the method may administer to the subject an oral daily dose of about 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, 250 mg/day, 255 mg/day, 260 mg/day, 265 mg/day, 270 mg/day, 275, mg/day, 280 mg/day, 285 mg/day, 290 mg/day, 295 mg/day, or 300 mg/day of elemental iron.

The iron may be administered intravenously to the subject. In some embodiments, the method may administer to the subject up to about 1000 mg of elemental iron per week. In other embodiments, the method may administer to the subject up to about 600 mg, 650 mg, 700 mg, 750 mg, 800 mg, 850 mg, 900 mg, or 950 mg of elemental iron per week.

c. Combinatorial Therapy

As described above, the treatment method administers nicotinamide riboside to the subject and may further include administering iron to the subject. The nicotinamide riboside and iron may be administered simultaneously. In other embodiments, the nicotinamide riboside and iron may be administered sequentially, in which nicotinamide riboside administration may precede iron administration or iron administration may precede nicotinamide riboside administration.

d. Pharmaceutical Composition

The nicotinamide riboside and/or iron may be incorporated into a pharmaceutical composition suitable for administration to a subject (such as a patient, which may be a human or non-human).

The pharmaceutical composition may include a "therapeutically effective amount" or a "prophylactically effective amount" of nicotinamide riboside and/or iron. A "therapeutically effective amount" refers to an amount effective, at dosages and for periods of time necessary, to achieve the desired therapeutic result. A therapeutically effective amount of nicotinamide riboside and/or iron may be determined by a person skilled in the art and may vary according to factors such as the disease state, age, sex, and weight of the individual, and the ability of the composition to elicit a desired response in the individual. A therapeutically effective amount is also one in which any toxic or detrimental effects of nicotinamide riboside and/or iron are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

The pharmaceutical composition may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

3. Diagnostic Method

Also provided herein is a method for identifying a subject suffering from heart failure as a candidate for treatment with nicotinamide riboside. In some embodiments, the method may also identify a subject suffering from heart failure associated with iron deficiency as a candidate for treatment with nicotinamide riboside. In still other embodiments, the method may further identify a subject suffering from heart failure associated with iron deficiency as a candidate for treatment with nicotinamide riboside, in which anemia is present with the iron deficiency.

The method may include obtaining a sample from the subject and measuring in the sample a level of a ratio of NAD/NADH, a level of iron, a level of a secreted or serum protein marker, or any combination thereof.

The secreted or serum protein marker may be secreted from a heart cell such as a cardiomyocyte. The secreted or serum protein marker may be secreted from a cell having the mitochondrial unfolded-protein response. The secreted or serum protein marker may be FGF21 protein, or Angiopoietin-like 4 (AngPtL4) protein, or the combination thereof. Accordingly, the method may measure a level of FGF21, AngPtL4, or the combination thereof.

Measuring the level of iron may include measuring serum ferritin, transferrin, transferrin saturation, serum iron, total iron-binding capacity, or any combination thereof.

The method may also include comparing the measured level to a control level. In some embodiments, the control level may be a predetermined or reference value, which is employed as a benchmark against which to assess the measured result. The predetermined or reference value may be a level in a sample from a subject not suffering from heart failure.

The method may further include identifying the subject as a candidate for treatment with nicotinamide riboside if measured level of the ratio of NAD/NADH is lower than the control level of the ratio of NAD/NADH, the measured level of iron is lower than the control level of iron, the measured level of FGF21 protein is higher than the control level of FGF21 protein, the measured level of AngPtL4 protein is higher than the control level of AngPtL4 protein, or any combination thereof. The nicotinamide riboside may be administered, alone or in combination with iron as described above, to the subject identified as a candidate for treatment with nicotinamide riboside.

4. Diagnostic Kit

Also provided herein a kit which may be used with the diagnostic method described above. The kit may include a positive control and/or a negative control. The kit may include material(s), which may be desirable from a user standpoint, such as a buffer(s), a diluent(s), a standard(s), and/or other material useful in sample processing, washing, or conducting any other step of the diagnostic method described herein.

The kit according to the present disclosure may also include instructions for carrying out the diagnostic method. Instructions included in the kit of the present disclosure may be affixed to packaging material or may be included as a package insert. While instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site which provides instructions.

The present invention has multiple aspects, illustrated by the following non-limiting examples.

5. Examples

Example 1

Materials and Methods for Examples 2-7

Animal Experiments.

129/SvEv mice bearing a floxed Tfrc allele were crossed with transgenic C57BL/6 mice expressing Cre recombinase under the control of the a-MyHC promoter. Backcrossing was with 129/SvEv mice for more than 10 generations and after the initial phenotypic characterization, all studies used mice with a homogeneous 129/SvEv background. Animals were genotyped by polymerase chain reaction (PCR) using genomic DNA from toe clips. Primers for Tfrc alleles, Cre, Hjv alleles, and Rosa26 are described in Table 1.

TABLE 1

Primers for genotyping.

| Gene name | Forward primer sequence | SEQ ID NO: | Reverse primer sequence | SEQ ID NO: |
|---|---|---|---|---|
| Tfrc | 5'-CAGTAATCCCAGAGGAATCATTAG-3' | 1 | 5'-CTAAACCGGGTGTATGACAATG-3' | 2 |
| Cre | 5'-CCATATTGGCAGAACGAAAAC-3' | 3 | 5'-GCTTCAAAAATCCCTTCCAGG-3' | 4 |
| Hjv WT | 5'-GAATGGCTTCCTTCCATCAA-3' | 5 | 5'-ATCTTCAAAGGCTGCAGGAA-3' | 6 |
| Hjv$^{-/-}$ | 5'-CGGATGGTTTTTGGCAGTTAG-3' | 7 | 5'-GCCTTTACGATATCTCAGTCC-3' | 8 |
| Rosa26 | 5'-GAGGGGAGTGTTGCAATA-3' | 9 | 5'-TCTGACACTAGCCTTTC-3' | 10 |

For iron rescue experiments, mice were injected intraperitoneal (IP) with 5 mg of iron dextran (Uniferon® 100 (25 µl)) at P3, or at both P3 and P7. For nicotinamide riboside (NR) rescue experiments, mice were injected IP with NR dissolved in PBS at 750 mg/kg daily from P5. Volume was based on the body weight, with less than 100 µl at postnatal day 10. Control animals were injected with PBS only as described in Yang et al. (2007) J. Med. Chem. 50:6458-6461, the entire contents of which are incorporated herein by reference.

Histopathological Analysis.

4 µm paraffin sections were stained with hematoxylin and eosin and examined by light microscopy. Cardiomyocyte dimensions were measured by digital morphometry of paraffin-embedded myocardial cross-sections stained with Alexa Fluor® 594 WGA (Life Technologies, Invitrogen) using ImageJ image processing. Apoptotic cells were identified and quantified using the In Situ Cell Death Detection Kit (Roche) on paraffin sections according to the manufacturer's instructions. Quantitation was done by ImageJ using three consecutive sections for each mouse.

Echocardiography.

Echocardiography was performed without anesthesia on 7 or 8 age-, sex- and body weight-matched mice per genotype by an investigator blinded to genotypes. Left ventricular dimension and fractional shortening were calculated based on data generated by echocardiography as described in Esposito et al. (2000) Am. J. Physiol. Heart Circ. Physiol. 279:H3101-3112, the entire contents of which are incorporated herein by reference.

Electron Microscopy.

Hearts were removed and rinsed quickly in cold Krebs-Henseleit buffer, and then immersed in 5% glutaraldehyde buffer. Samples were prepared for transmission electron microscopy and imaged by Duke University Medical Center Research Electron Microscopy Services.

Tissue Iron Analysis.

Heart non-heme iron was measured as described in Levy et al. (1999) Nat. Genetics 21:396-399 and Torrance and Bothwell (1980) Methods in Hematology, J. D. Cook, ed. (New York, Churchill Livingstone Press) pp. 104-109, the entire contents of both of which are incorporated herein by reference.

Enzymatic Analysis of Respiratory Chain Complexes I-IV.

Tissues were homogenized in 250 mM sucrose, 40 mM potassium chloride, 1 mM EGTA, 1 mg/ml fatty acid free BSA, 20 mM Tris-HCl (pH 7.2) and homogenates were centrifuged at 600×g for 10 min at 4° C. Steady state activities of enzyme complexes in the supernatant were determined as described in Janssen et al. (2007) Clin. Chem. 53:729-734 and Spinazzi et al. (2011) Mitochondrion 11:893-904, the entire contents of both of which are incorporated herein by reference.

Preparation of Mitochondrial Lysates and Acetyl-Lysine Analysis.

Mouse hearts were homogenized (40-50 strokes) in 15 volumes of ice-cold homogenization buffer [320 mM sucrose, 50 mM KH2PO4 (pH 7.4), 10 mM Tris-HCl (pH 7.4), 1 mM EDTA] in the presence of protease inhibitors, phosphatase inhibitors (Roche), and deacetylase inhibitors (2.5 µM Trichostatin A, 5 mM nicotinamide, 5 mM sodium butyrate) using glass homogenizers. Crude mitochondria were isolated by differential centrifugation. Homogenates were centrifuged at 1600 rpm for 10 min at 4° C. The supernatant was centrifuged again at 1600 rpm for 10 min at 4° C. The supernatant was subsequently centrifuged at 10,000×g for 10 min at 4° C. The pellet was collected, rinsed with 1 ml homogenization buffer and centrifuged at 10,000×g again for 10 min at 4° C. The pellet was resuspended in 100 µl 20 mM HEPES (pH 7.4), 150 mM NaC, and 1% Triton-X-100 with protease, phosphatase and deacetylase inhibitors. Western blot analysis was performed with 70 μg protein per lane. Antibodies recognizing acetyl-lysine were purchased from Cell Signaling Technology.

Statistical Analysis.

One-way ANOVA was performed for comparisons between two means, including when the comparison was between the means of WT and Tfr1$^{hrt/hrt}$. Survival analysis was performed using Logrank in Graphpad software. P<0.05 was considered statistically significant.

An independent statistical analysis for survival analysis was also performed as described below.

Survival time was modeled as follows:

$$Tij = \mu + Bj + sij$$

Where Tij was the survival time (in days) for the i-th mouse in the j-th group. The model explained this in terms of a baseline mean m, an effect bj for the j-th group (relative to baseline) and inter-mouse variation eij. The model was fit using ordinary least squares (1-way ANOVA).

For the Tfr1R654A rescue experiment, the baseline was Tfr1$^{hrt/hrt}$ There was a significant improvement in mean survival in the Tfr1$^{hrt/hrt}$; Tfr1R654A group (2.7 days, p-value<0.001, Table 2). In WT, the improvement was over 49 days (all observations were censored in this group).

TABLE 2

Analysis of survival for experiment 2.

| | Effect | Std. Error | T Value | P-value |
|---|---|---|---|---|
| Tfr1$^{hrt/hrt}$ | 11.000 | 0.141 | 77.782 | |
| Tfr1$^{hrt/hrt}$; Tfr1$^{R654A}$ | 2.700 | 0.173 | 15.588 | <0.001 |
| WT | 49.000 | 0.200 | 245.000 | <0.001 |
| WT; Tfr1$^{R654A}$ | 49.000 | 0.200 | 245.000 | <0.001 |

For the NR rescue experiment, the baseline was Tfr1$^{hrt/hrt}$ with PBS. There was no significant improvement in mean survival when using just Tfr1$^{hrt/hrt}$ (0.625 days, p-value=0.26, Table 3). There was, however, a significant improvement in the Tfr1$^{hrt/hrt}$ with NR group (2.29 days, p-value<0.001). For statistical calculations, lifespan was over 19.6 days for wild-type mice.

TABLE 3

Analysis of survival for experiment 1.

| | Effect | Std. Error | t value | P-value |
|---|---|---|---|---|
| Baseline | 10.375 | 0.402 | 25.787 | |
| Tfr1$^{hrt/hrt}$ | 0.625 | 0.540 | 1.158 | 0.258 |
| Tfr1$^{hrt/hrt}$ with NR | 2.292 | 0.484 | 4.739 | <0.001 |
| WT with NR | 19.625 | 0.493 | 39.827 | <0.001 |
| WT with PBS | 19.625 | 0.569 | 34.491 | <0.001 |

Western Blot Analysis.

Mouse hearts were homogenized in 15 volumes of ice-cold RIPA buffer in the presence of protease inhibitors and phosphatase inhibitors (Roche) using glass homogenizers. Protein lysates were collected as the supernatant after centrifugation at 14,000 rpm for 15 min at 4° C. Protein concentrations were determined using the DC protein assay (Bio-Rad). Antibodies were used recognizing Dpyd, Cathepsin D, Tom20 (Santa Cruz Biotechnology), LC3, Gabarap, p62, Beclin-1, Ulk1, Atg3, Atg4B, Atg7, Atg5, Atg12, Atg16L1, Bnip3, Nix, H-Ferritin (Cell Signaling Technology), Atg10 (ThermoFisher Scientific), Fundc1 (Aviva Systems Biology), Rcan1 (Abgent), Rpl19 (Sigma-Aldrich), Tfr1 (Invitrogen), Ppat and Atg9A (Novus Biologicals). Total OXPHOS Rodent WB Antibody Cocktail was purchased from Abcam.

RNA Extraction, Microarray Gene Expression Analysis, and PCR.

Total heart RNA was isolated from flash-frozen tissue using the RNeasy Fibrous Tissue Mini Kit (Qiagen) and reverse transcribed as described in Schmidt et al. (2008) Cell Metab. 7:205-214, the entire contents of which are incorporated herein by reference. For the microarray analysis, the Affymetrix GeneChip® Mouse Genome 430 2.0 Array was used. A minimum of 200 ng RNA was used for each sample. RNA samples were processed by the Duke Microarray Shared Resource Services. Transcript abundance was quantified by 2-step real-time PCR, using amplification conditions as described in Schmidt et al. (2008) Cell Metab. 7:205-214, the entire contents of which are incorporated herein by reference. Primers are summarized in Table 2 and Rpl19 was used as an internal control.

TABLE 4

Primers for real-time.

| Gene name | Forward primer sequence | SEQ ID NO: | Reverse primer sequence | SEQ ID NO |
|---|---|---|---|---|
| Tfrc | 5'-TCAAGCCAGATCAGCATTCTC-3' | 11 | 5'-AGCCAGTTTCATCTCCACATG-3' | 12 |
| Nppa | 5'-TCGTCTTGGCCTTTTGGCT-3' | 13 | 5'-TCCAGGTGGTCTAGCAGGTTCT-3' | 14 |
| Nppb | 5'-AAGTCCTAGCCAGTCTCCAGA-3' | 15 | 5'-GAGCTGTCTCTGGGCCATTTTC-3' | 16 |
| Myh7 | 5'-GTGCCAAGGGCCTGAATGAG-3 | 17 | 5'-GCAAAGGCTCCAGGTCTGA-3' | 18 |
| Acta1 | 5'-ATGTGCGACGAAGACGAGACCA-3' | 19 | 5'-AGGGTCAGGATACCTCGCTTG-3' | 20 |

TABLE 4-continued

Primers for real-time.

| Gene name | Forward primer sequence | SEQ ID NO: | Reverse primer sequence | SEQ ID NO |
|---|---|---|---|---|
| Polrmt | 5'-CTCCTCCCACATGATGCTGAC-3' | 21 | 5'-AATTGCTCGCGGCATACCT-3' | 22 |
| Nd4 | 5'-CATCACTCCTATTCTGCCTAGCAA-3' | 23 | 5'-TCCTCGGGCCATGATTATAGTAC-3' | 24 |
| Cytb | 5'-GCCACCTTGACCCGATTCT-3' | 25 | 5'-TTGCTAGGGCCGCGATAAT-3' | 26 |
| Cox3 | 5'-CGGAAGTATTTTTCTTTGCAGGAT-3' | 27 | 5'-CAGCAGCCTCCTAGATCATGTG-3' | 28 |
| Ppargc1a | 5'-AGAAGTCCCATACACAACCGCAGTCGCAA-3' | 29 | 5'-CTTGGAGCTGTTTTCTGGTGCTGCAAGGA-3' | 30 |
| Ppargc1b | 5'-GCTCTGGTAGGGGCAGTG-A-3' | 31 | 5'-TCCTGTAAAAGCCCGGAGTAT-3' | 32 |
| Itgb1bp3 | 5'-TACAGCCAACGCTACTTCCT-3' | 33 | 5'-GGGACTTCATGCCATCTAAA-3' | 34 |
| Slc3a2 | 5'-TGATGAATGCACCCTTGTACTTG-3' | 35 | 5'-TCCCCAGTGAAAGTGGA-3' | 36 |
| Slc7a5 | 5'-TGGTCTTCGCCACCTACTTG-3' | 37 | 5'-AAGCCGAGCAAAATGrATGAG-3' | 38 |
| Art1 | 5'-CAGGGGCTACTCCTTTTTCC-3' | 39 | 5'-CCCAGACCTGCACTTCTTTT-3' | 40 |
| Art4 | 5'-AAGAAAAGAAGTGCAGGTCTGG-3' | 41 | 5'-AGAGCAGGAAGCAGAAATGG-3' | 42 |
| Art5 | 5'-TGTGTCCTCAAGAGCAGTCG-3' | 43 | 5'-CAACTCTGGTTGGACAGGT-3' | 44 |
| Ppara | 5'-GCCTGTCTGTCGGGATGT-3' | 45 | 5'-GGCTTCGTGGATTCTCTTG-3' | 46 |
| Rxrg | 5'-CCGCTGCCAGTACTGTCG-3' | 47 | 5'-ACCTGGTCCTCCAAGGTGAG-3' | 48 |
| Fatp1 | 5'-CGCTTTCTGCGTATCGTCTG-3' | 49 | 5'-GATGCACGGGATCGTGTCT-3' | 50 |
| Rcan1.4 | 5'-CTTGTGTGGCAAACGATGATG-3' | 51 | 5'-TGGTGTCCTTGTCATATGTTCTG-3' | 52 |
| Map1lc3b | 5'-CGTCCTGGACAAGACCAAGT-3' | 53 | 5'-ATTGCTGTCCCGAATGTCTC-3' | 54 |
| 5 | 5'-TGTCCTGGATAAGACCAAGT-3' | 55 | 5'-TTCATCCTTCTCCTGTTCAT-3' | 56 |

TABLE 4-continued

Primers for real-time.

| Gene name | Forward primer sequence | SEQ ID NO: | Reverse primer sequence | SEQ ID NO |
|---|---|---|---|---|
| Lpn1 | 5'-CCTTCTATGCTGCTTTTGGGAACC-3' | 57 | 5'-GTGATCGACCACTTCGCAGAGC-3' | 58 |
| Epas1 | 5'-TAAAGCGGCAGCTGGAGTAT-3' | 59 | 5'-ACTGGGAGGCATAGCACTGT-3' | 60 |
| Slc2a1 | 5'-GCTTATGGGCTTCTCCAAACT-3' | 61 | 5'-GGTGACACCTCTCCCACATAC-3' | 62 |
| Slc16a3 | 5'-TCACGGGTTTCTCCTACGC-3' | 63 | 5'-GCCAAAGCGGTTCACACAC-3' | 64 |
| Pdk1 | 5'-GCTACTCAACCAGCACTCCT-3' | 65 | 5'-CCTGGTGATTTCGCATTT-3' | 66 |
| Lonp1 | 5'-ATGGTGGAGGTTGAGAATGTAG-3' | 67 | 5'-TGGTCTCTTCCAGAACATCTTG-3' | 68 |
| Bnip3 | 5'-GGCGTCTGACAACTTCCACT-3' | 69 | 5'-AACACCCAAGGACCATGCTA-3' | 70 |
| Ldha | 5'-AGGCTCCCCAGAACAAGATT-3' | 71 | 5'-TCTCGCCCTTGAGTTTGTCT-3' | 72 |
| Vegfa | 5'-CCTGGTGGACATCTTCCAGGAGTACC-3' | 73 | 5'-GAAGCTCATCTCTCCTATGTGCTGGC-3' | 74 |
| Ndrg1 | 5'-CATTTTGCTGTCTGCCATG-3' | 75 | 5'-CCATGCCAATGACACTCTTG-3' | 76 |
| Hk2 | 5'-TGATCGCCTGCTTATTCACGG-3' | 77 | 5'-AACCGCCTAGAAATCTCCAGA-3' | 78 |
| Gpi1 | 5'-GCCAAAGTGAAAGAGTTTGGA-3' | 79 | 5'-ATGGAAAGTCCAATGGCTGA-3' | 80 |
| Pfk1 | 5'-CTGCTGGTGATTGGTGGCTTTG-3' | 81 | 5'-TTGCTGATGGTGGCTGGGATG-3' | 82 |
| Aldoa | 5'-GTGGGAAGAAGGAGAACCTG-3' | 83 | 5'-CTGGAGTGTTGATGGAGCAG-3' | 84 |
| Tpi | 5'-CCAGGAAGTTCTTCGTTGGGG-3' | 85 | 5'-CAAAGTCGATGTAAGCGGTGG-3' | 86 |
| Gapdh | 5'-CATGGCCTTCCGTGTTCCTA-3' | 87 | 5'-GCGGCACGTCAGATCCA-3' | 88 |
| Pgk1 | 5'-CTCCGCTTTCATGTAGAGGAAG-3' | 89 | 5'-GACATCTCCTAGTTTGGACAGTG-3' | 90 |
| Pgam1 | 5'-CTGTGCAGAAGAGAGCAATCC-3' | 91 | 5'-CTGTCAGACCGCCATAGTGT-3' | 92 |
| Eno1 | 5'-TGCGTCCACTGGCATCTAC-3' | 93 | 5'-CAGAGCAGGCGCAATAGTTTTA-3' | 94 |

TABLE 4-continued

Primers for real-time.

| Gene name | Forward primer sequence | SEQ ID NO: | Reverse primer sequence | SEQ ID NO |
|---|---|---|---|---|
| Pkm2 | 5'-TGTCTGGAGAAACAGCCAAG-3' | 95 | 5'-TCCTCGAATAGCTGCAAGTG-3' | 96 |
| Sqstm1 | 5'-GAAGAATGTGGGGGAGAGTGTGG-3' | 97 | 5'-TGCCTGTGCTGGAACTTTCTGG-3' | 98 |
| Rpl19 | 5'-AGGCATATGGGCATAGGGAAGAG-3' | 99 | 5'-TTGACCTTCAGGTACAGGCTGTG-3' | 100 |
| c-Myc | 5'-CCTAGTGCTGCATGAGGAGA-3' | 101 | 5'-TCTTCCTCATCTTCTTGCTCTTC-3' | 102 |
| Optn | 5'-CAAGTGACCTCTCTGTTTAAGG-3' | 103 | 5'-GCCTGCTCCATCTTGATTT-3' | 104 |
| Atf4 | 5'-GAGCTTCCTGAACAGCGAAGTG-3' | 105 | 5'-TGGCCACCTCCAGATAGTCATC-3' | 106 |
| Ddit3 | 5'-GACTCAGCTGCCATGACTG-3' | 107 | 5'-GCGACAGAGCCAGAATAACAG-3' | 108 |
| Fgf21 | 5'-TCCAAATCCTGGGTGTCAAA-3' | 109 | 5'-CAGCAGCAGTTCTCTGAAGC-3' | 110 |

Spectrophotometric Analysis of Single Respiratory Chain Complexes I-IV.

All reactions were performed using a computer-tunable spectrophotometer (Spectramax Plus Microplate Reader, Molecular Devices, Sunnyvale, Calif.) at 20-s intervals for 5 minutes at room temperature. The reaction conditions for assaying activity of each complex were described in Janssen et al. (2007) Clin. Chem. 53:729-734 and Spinazzi et al. (2011) Mitochondrion 11:893-904, the entire contents of both of which are incorporated herein by reference. The total volume of each reaction was 200 µl. Each sample had three replicates for total activity and inhibitor-insensitive activity. For complexes I and II, 2,6-dichloroindophenol (DCIP) reduction by electrons accepted from decylubiquinol was measured. The reduction of DCIP was followed by spectrophotometry at 600 nm. 20 µg heart homogenates were used in each reaction for both complex I and complex II activity assays. Complex III activity was measured by following the reduction of cytochrome c at 550 nm. Complex IV activity was measured by following the oxidation of reduced cytochrome c at 550 nm. 3.6 µg and 1 µg of heart homogenate were used in each reaction for complex III and complex IV activity assays, respectively. The addition of standard respiratory chain inhibitors for each complex was used to ascertain the specificity of the enzymatic assays. The same amount of protein was used for each sample.

Example 2

Tfr1 Deficiency Causes Cardiomyopathy

Figure 1B:
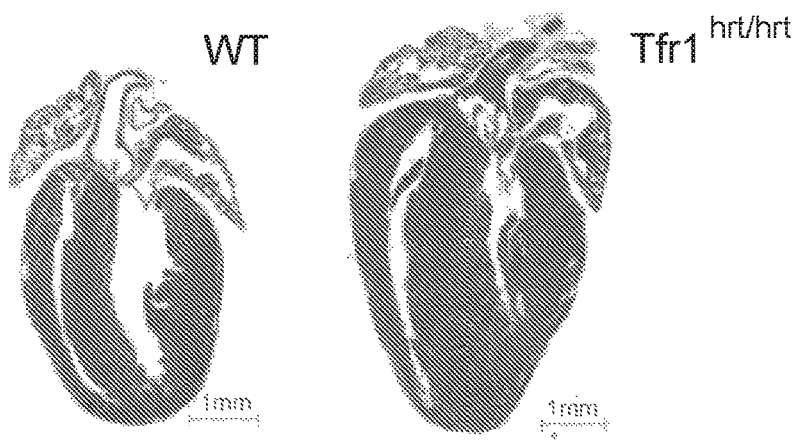
Figure 1C:
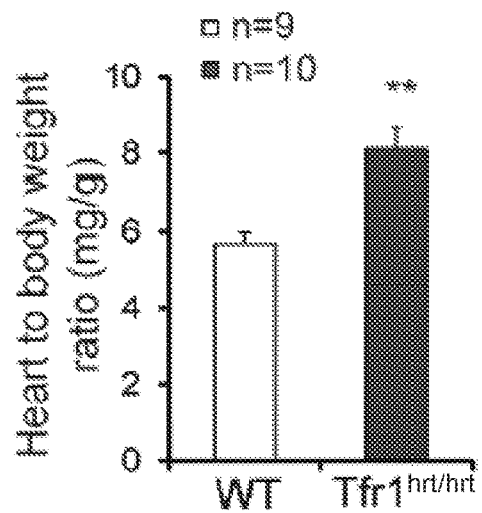
Figure 8:
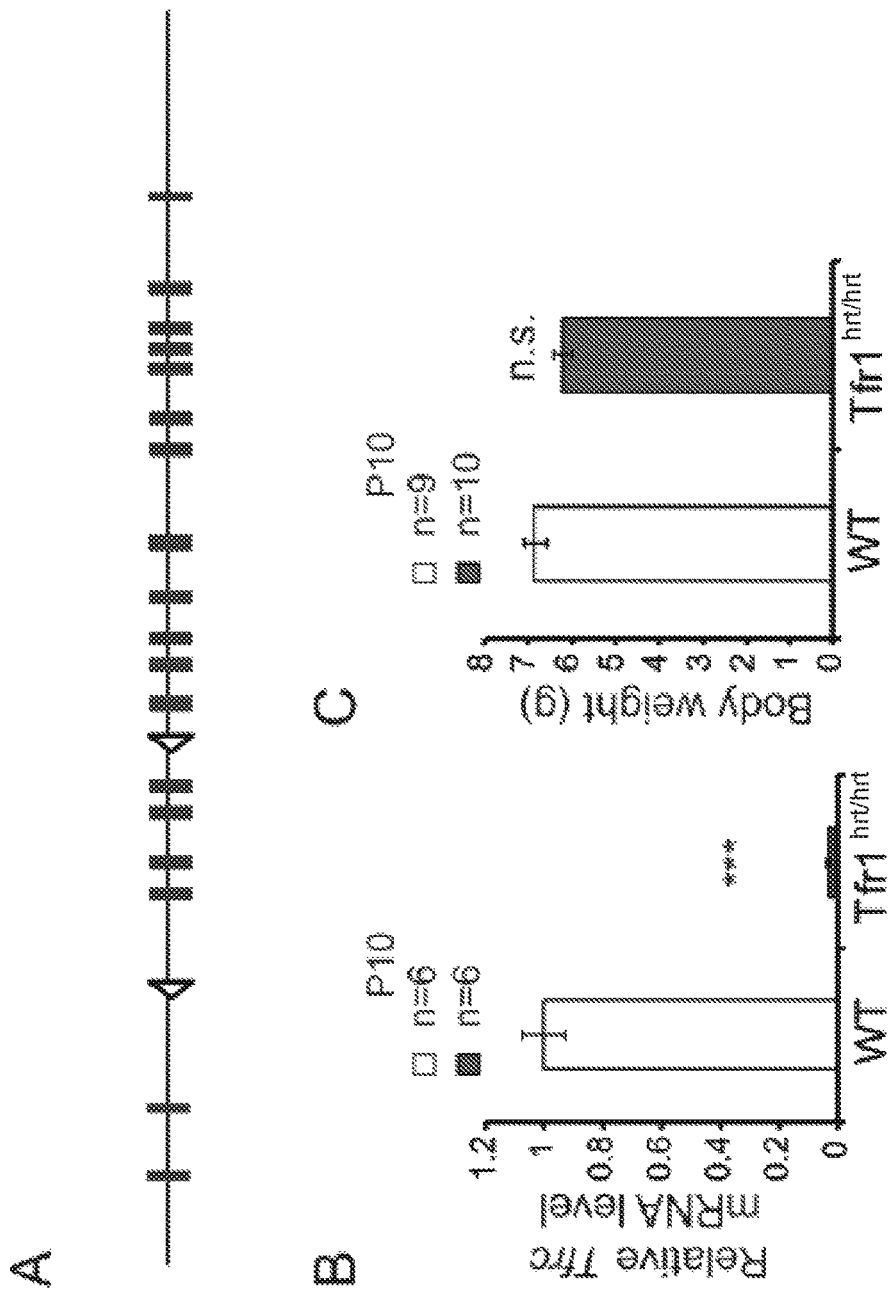
FIG. 8 shows the floxed Tfrc allele configuration and preliminary characterization of Tfr1$^{hrt/hrt}$ mice (related to FIG. 1). (A) Schematic diagram of floxed Tfrc allele allowing for deletion of exons 3-6. (B) Levels of Tfrc mRNA in hearts from littermate wild-type (WT) and Tfr1$^{hrt/hrt}$ mice at P10. (C) Body weights of littermate WT and Tfr1$^{hrt/hrt}$ mice at P10. Data were presented as means±SEM. P-values were determined by ANOVA. The sample size (n) was indicated. ***p<0.001; n.s., not significant.
Figure 11:
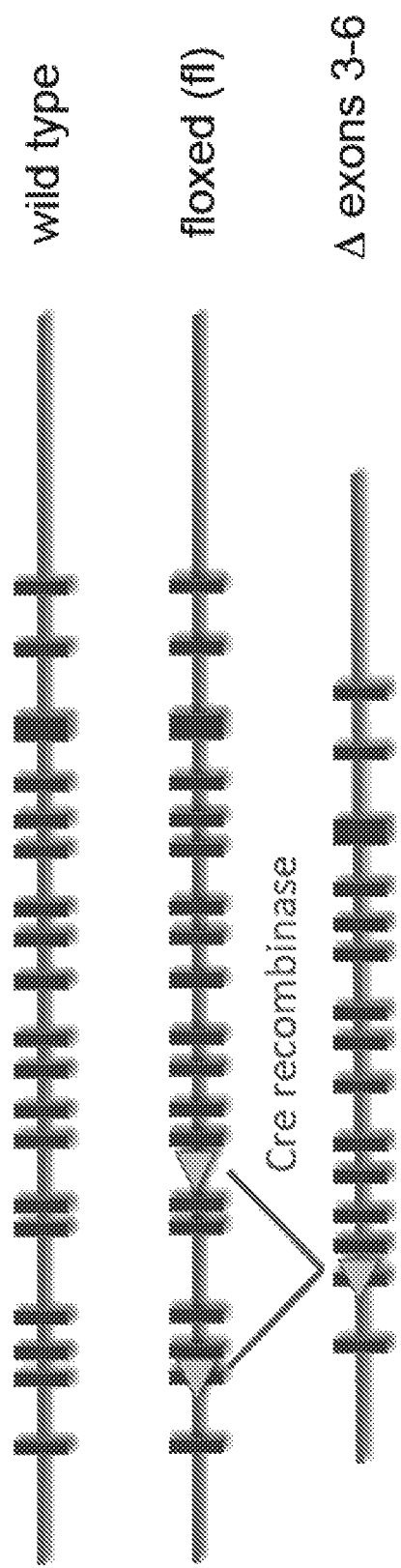
FIG. 11 shows a schematic illustrating the generation of Tfr1$^{hrt/hrt}$.
Figure 12:
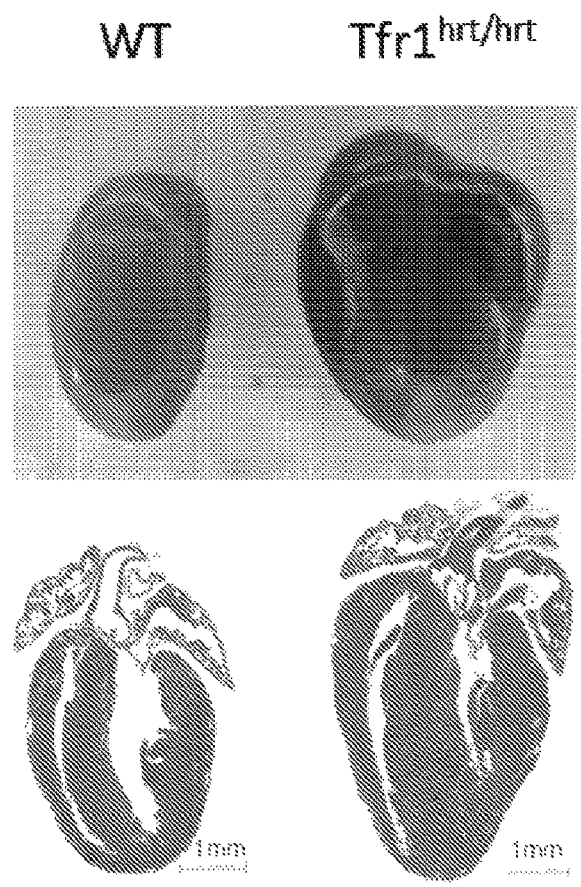
FIG. 12 shows images of heart sections from wild-type (WT) and Tfr1$^{hrt/hrt}$ mice.

Murine Tfr1 was inactivated in cardiomyocytes by expressing a Myh6-Cre transgene to recombine loxP sites flanking Tfrc exons 3 to 6 (FIGS. 8A and 11). It was confirmed that mutant animals (Tfr1$^{hrt/hrt}$) expressed little Tfr1 mRNA in heart (FIG. 8B). Tfr1$^{hrt/hrt}$ mice were born in Mendelian ratios and maintained body weights similar to wild type (WT) littermates (Tfr1$^{fl/fl}$ and Tfr1$^{fl/+}$ mice, FIGS. 1A and 8C), but died after several hours of distress by postnatal day 11 (P11) with cardiac hypertrophy (FIGS. 1B and 12) and elevated heart to body weight ratios (FIG. 1C), which had not been observed at P5 (not shown).

Figure 1D:
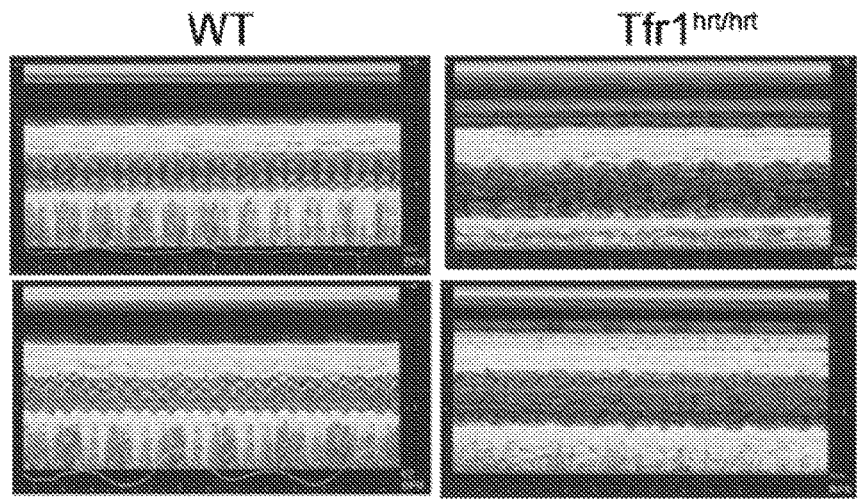
Figure 1E:
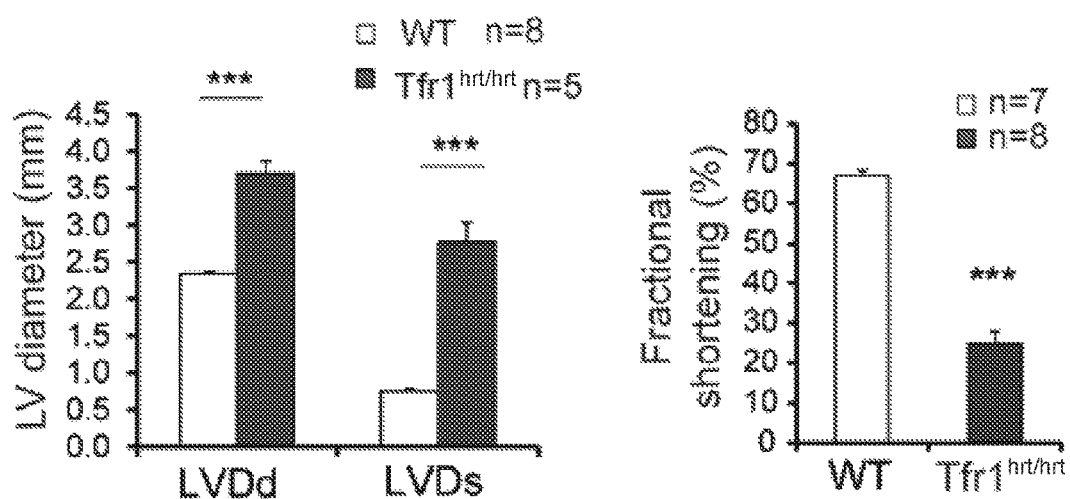
Figure 13:
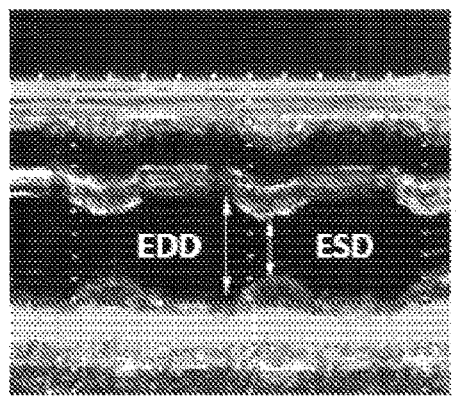
FIG. 13 shows end diastolic diameter (EDD) and end systolic diameter (ESD) from wild-type (WT) mice.

Echocardiography of Tfr1$^{hrt/hrt}$ mice showed left ventricular dilatation in both systole and diastole, and decreased fractional shortening (FIGS. 1D and 1E), indicating compromised performance of the heart as a pump. FIG. 13 shows the end diastolic diameter (EDD) and end systolic diameter (ESD) from wild-type (WT) mice. Wheat germ agglutinin staining showed enlarged Tfr1$^{hrt/hrt}$ cardiomyocytes, consistent with cardiomyocyte hypertrophy (FIG. 1F). There was increased mRNA encoding markers for cardiac hypertrophy Nppa (atrial natriuretic peptide) and Nppb (brain natriuretic peptide), Myh7 (myosin heavy chain B), and Acta1 (FIG. 1G). Thus, deletion of Tfr1 in cardiomyocytes led to dilated cardiomyopathy and early death.

Example 3

Cardiac Iron Deficiency

Figures 2A, 2B, 2C:
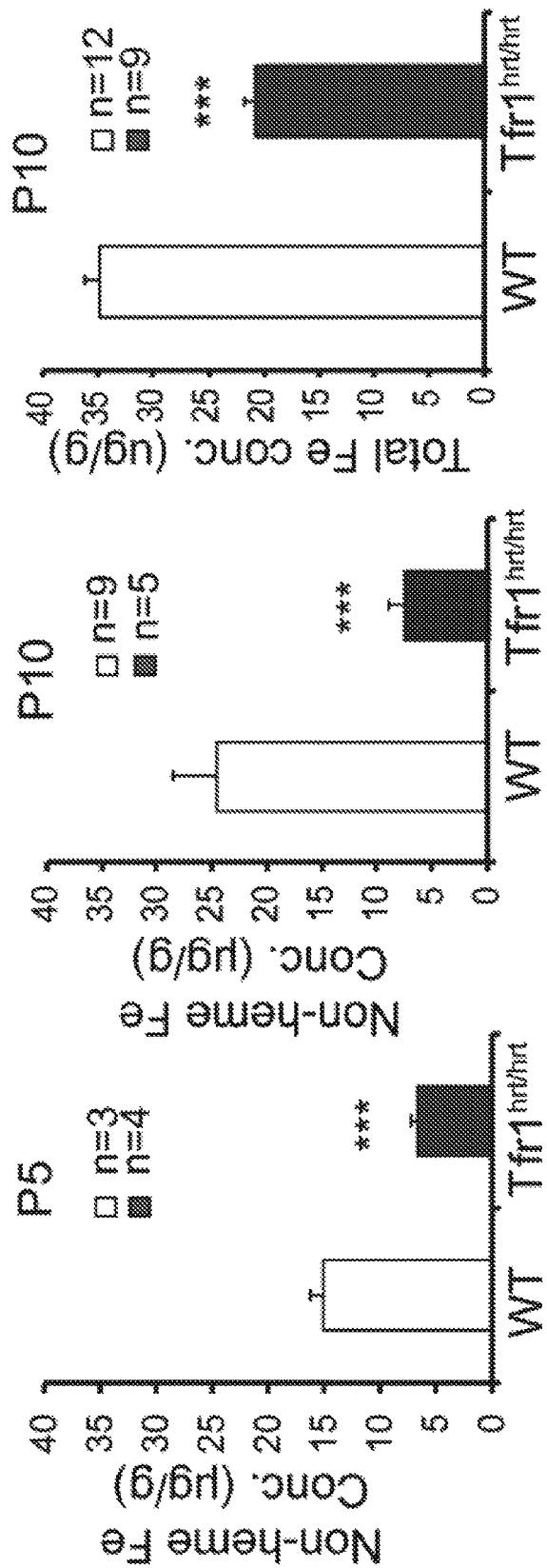
FIG. 2 shows iron deficiency and insufficient Fe—S cluster biogenesis in Tfr1$^{hrt/hrt}$ mice. (A-C) Non-heme iron levels in the heart at P5 (A) and P10 (B); total iron concentration at P10 to P11 (C). (D) Decreased Fe—S cluster proteins Dpyd and Ppat in hearts from Tfr1$^{hrt/hrt}$ mice with Rpl19 control. Age and genotype were shown at the top. Data were presented as means±SEM. Sample size (n) was indicated. ***p<0.001 by one-way ANOVA.
Figure 2D:
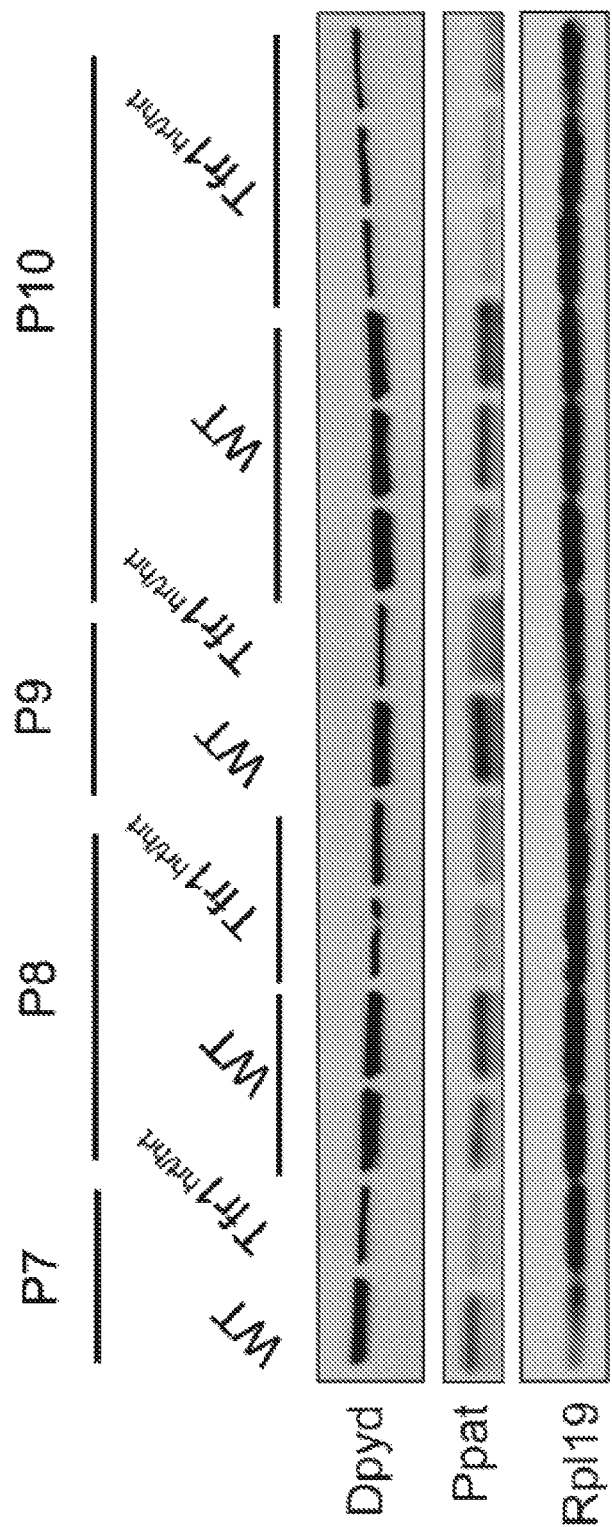

The canonical function of Tfr1 is to supply iron to meet cellular needs. Non-heme cardiac iron was measured to determine whether loss of Tfr1 resulted in iron deficiency. At P5, cardiac iron concentration was decreased in Tfr1$^{hrt/hrt}$ mice. Between P5 and P10, non-heme iron nearly doubled in WT hearts, but increased only slightly in Tfr1$^{hrt/hrt}$ hearts (FIGS. 2A and 2B), indicating that loss of Tfr1 impaired iron uptake. The total iron concentration at P10 showed less deficit in Tfr1$^{hrt/hrt}$ mice (FIG. 2C), indicating that heme iron was relatively spared. Fe—S clusters are synthesized from non-heme iron, and the amounts of enzymes Dpyd and Ppat are decreased when Fe—S clusters were not available. Both proteins were deficient in Tfr1$^{hrt/hrt}$ hearts (FIG. 2D), consistent with compromised Fe—S cluster biogenesis due to iron deficiency or mitochondrial dysfunction. It was concluded that Tfr1 was important for iron uptake by cardiomyocytes.

Example 4

Metabolic Changes Associated with Cardiomyopathy

Figure 3A:
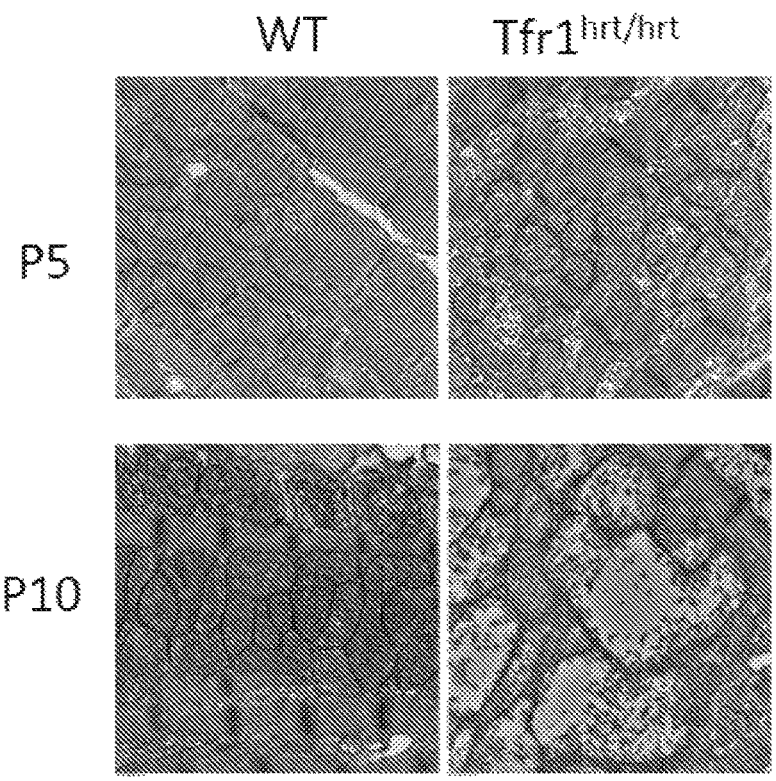
FIG. 3 shows abnormal mitochondrial morphology and function in hearts from Tfr1$^{hrt/hrt}$ mice. (A) Electron micrographs comparing mitochondria in WT and Tfr1$^{hrt/hrt}$ hearts. Tfr1$^{hrt/hrt}$ mitochondria were slightly abnormal at P5, but markedly enlarged and disrupted at P10. Scale bars=500 nm. (B) Representative protein levels for ETC complexes by immunoblot. (C) Enzymatic activity of complexes I to IV of ETC from P10 Tfr1$^{hrt/hrt}$ and WT littermates. (D) Relative mRNA levels of Polrmt and mitochondria-encoded genes.
Figures 14A, 14B, 14C:
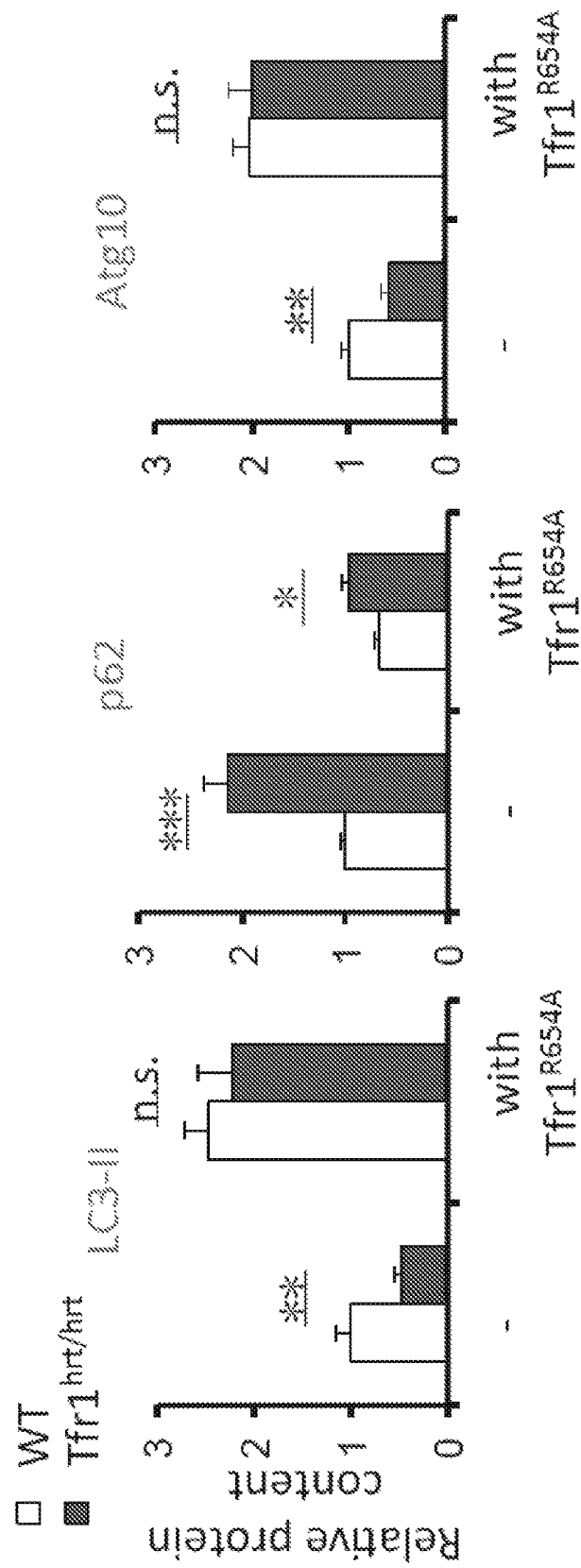
FIG. 14 shows relative protein content for (A) LC3-II, (B) p62, and (C) Atg10 in wild-type (WT; white bars) and Tfr1$^{hrt/hrt}$ (gray bars).
Figure 15:
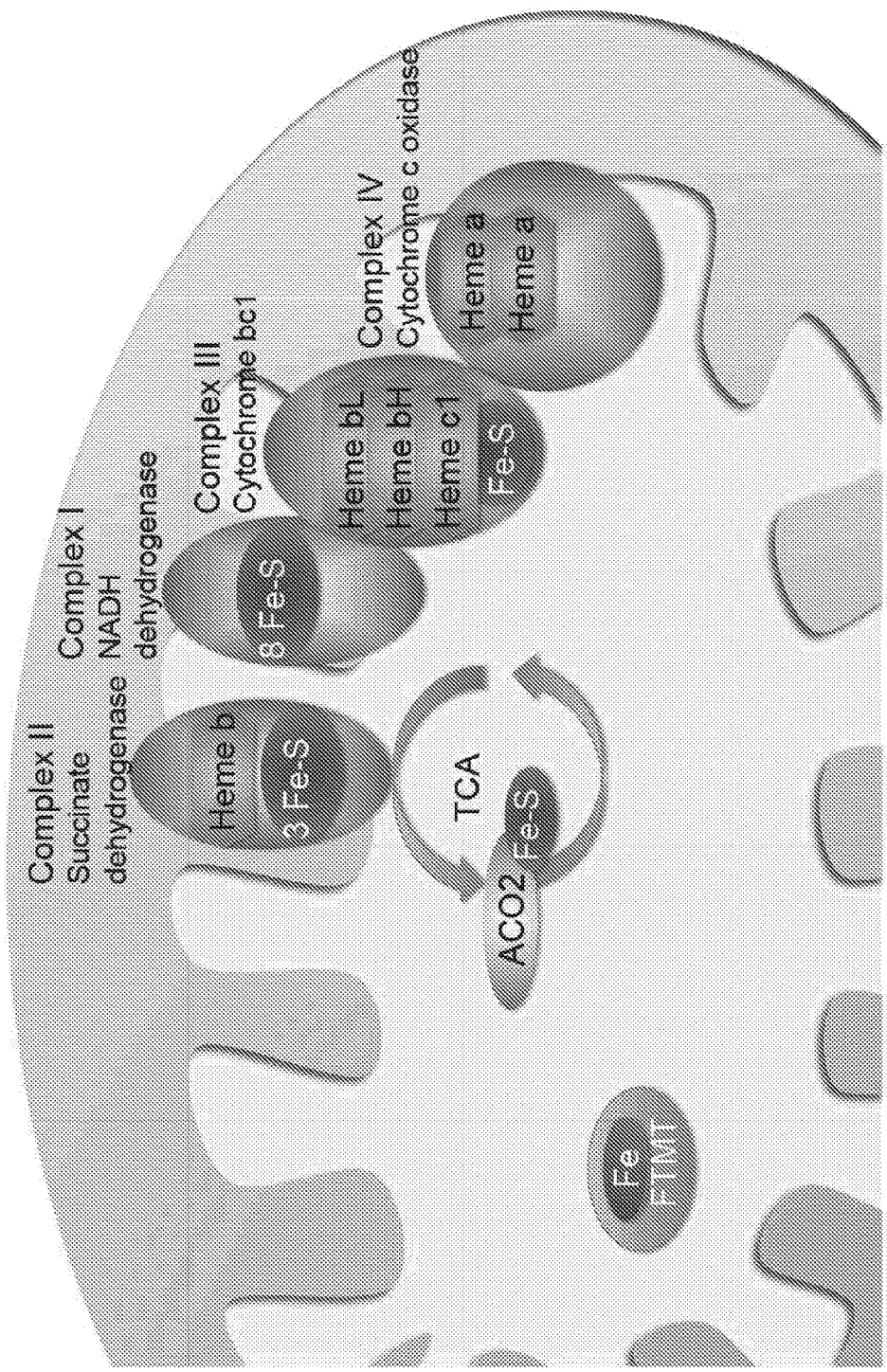
FIG. 15 shows a schematic illustrating complexes I, II, III, and IV of the electron transport chain (ETC).

Mitochondria from Tfr1$^{hrt/hrt}$ hearts were slightly abnormal at P5, and severely disrupted and enlarged at P10 (FIGS. 3A and 14). Fe—S clusters and heme are required by most complexes of the electron transport chain (ETC). FIG. 15 shows a schematic illustrating the requirement of Fe—S clusters and heme by complexes I, II, III, and IV of the ETC. As such, ETC complexes were examined by immunoblotting for proteins that are labile when the complexes are not assembled properly.

Figure 3B:
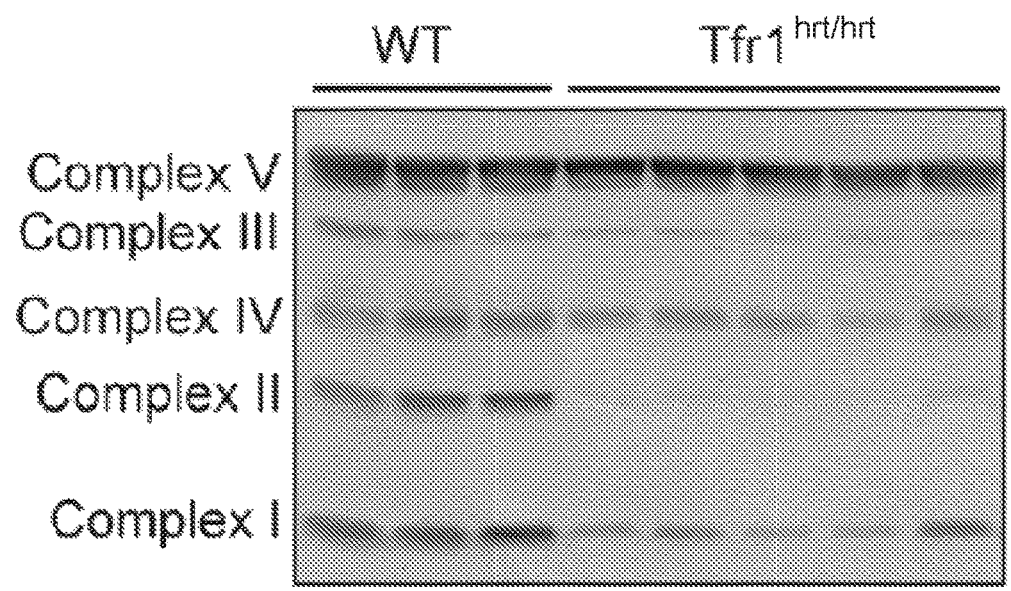

At P5, complex II was decreased in Tfr1$^{hrt/hrt}$ hearts and complex IV was increased, but the other ETC complexes did not differ from controls (FIG. 3B).

Figure 3C:
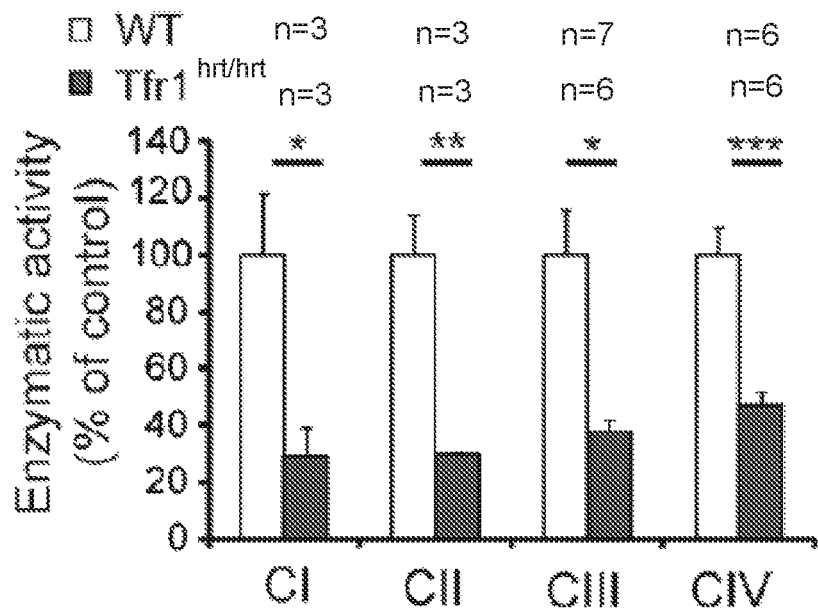
Figure 18:
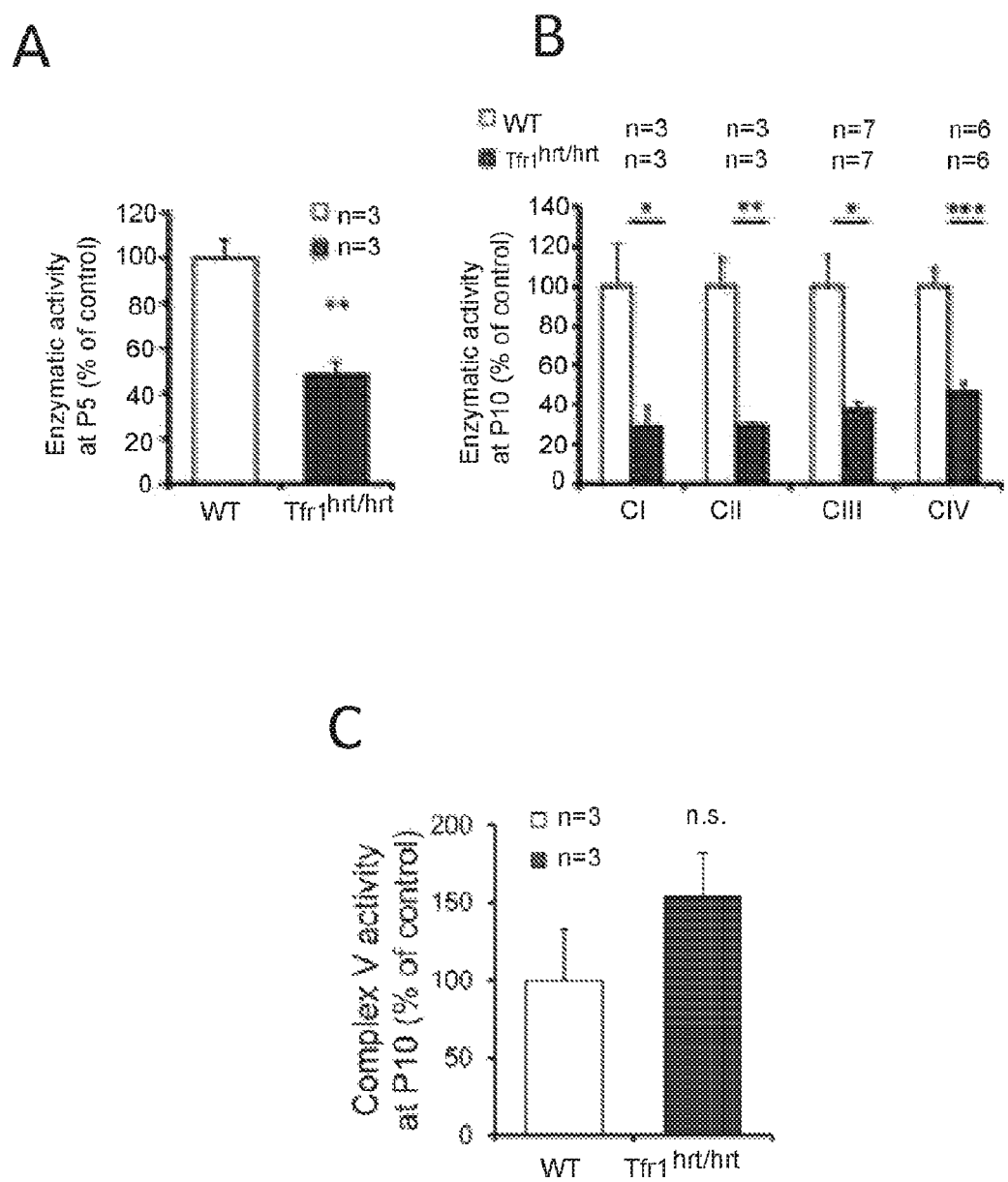
FIG. 18 shows abnormal mitochondrial morphology and function in hearts from Tfr1$^{hrt/hrt}$ mice. (A) Enzymatic activity of complex II of ETC from P5 Tfr1$^{hrt/hrt}$ and WT littermates. (B) Enzymatic activity of complexes I to IV of ETC from P10 Tfr1$^{hrt/hrt}$ and WT littermates. (C) Enzymatic activity of complex V of ETC from P10 Tfr1$^{hrt/hrt}$ and WT littermates.

Iron-containing complexes I through IV were diminished in hearts from Tfr1$^{hrt/hrt}$ mice at P10, but complex V, which does not contain iron, was unchanged (FIG. 3C). Accordingly, activities of complexes I to IV were markedly decreased in Tfr1$^{hrt/hrt}$ hearts (FIG. 3C). Activity of complex II was decreased at P5 (FIG. 18A), and activities of complexes I to IV were all markedly decreased at P10 in Tfr1$^{hrt/hrt}$ hearts (FIG. 18B) at P10. However, complex V, which does not contain iron, appeared unchanged at both ages, and its activity was not decreased in Tfr1hrt/hrt hearts at P10 (FIG. 18C).

Figure 3D:
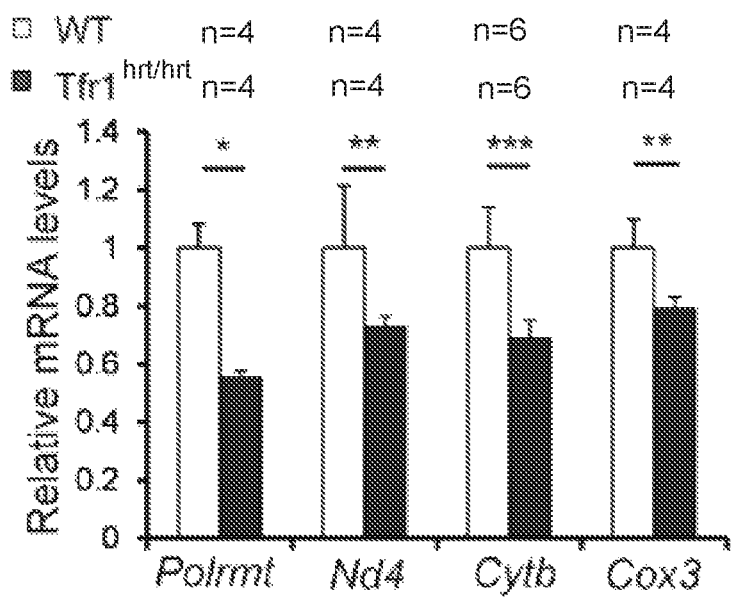

Expression of mitochondrial RNA polymerase (Polrmt) and mitochondria-encoded mRNA for Nd4, Cytb and Cox3 was similar to WT at P5 (not shown), but by P10 all were decreased in Tfr1$^{hrt/hrt}$ hearts (FIG. 3D), indicating fewer mitochondria or mitochondria incapable of normal gene expression.

mRNA profiling was used to examine gene expression changes in Tfr1$^{hrt/hrt}$ hearts and patterns were looked for using Gene Set Enrichment Analysis. Genes downregulated in the mutants were significantly associated with PPAR (particularly PPARa) and PGC1-a signaling, myogenesis, insulin signaling and cardiomyopathy. Upregulated genes were significant for hypoxia-inducible targets, Myc targets and glycolytic enzymes.

Figure 3E:
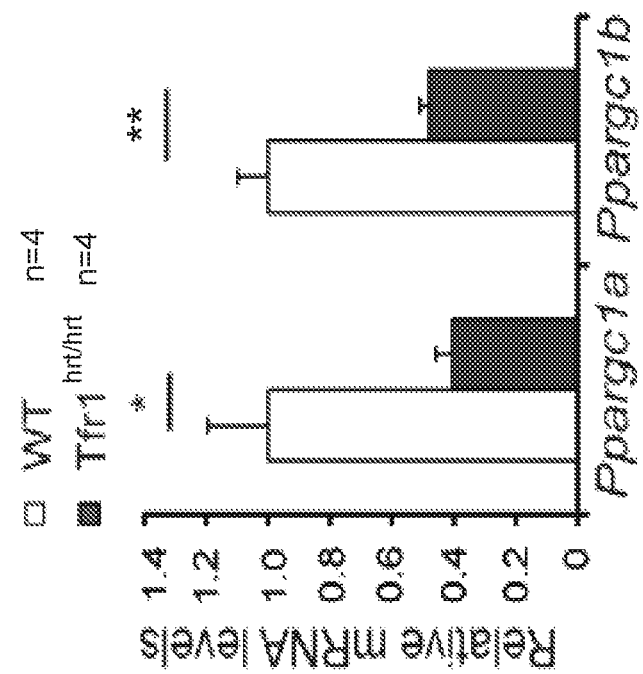

Decreased expression of mRNA encoding both PGC1-a (Ppargc1a) and PGC1-B (Ppargc1b) in Tfr1$^{hrt/hrt}$ hearts (FIG. 3E) was confirmed. PGC1-a controls transcription of a suite of nuclear genes to induce mitochondrial biogenesis. Mice deficient in PGC1-a in the heart developed cardiomyopathy, similar to the mutant mice Tfr1$^{hrt/hrt}$. These results indicated an impaired ability to induce mitochondrial biosynthesis in Tfr1$^{hrt/hrt}$ mice.

Figure 3F:
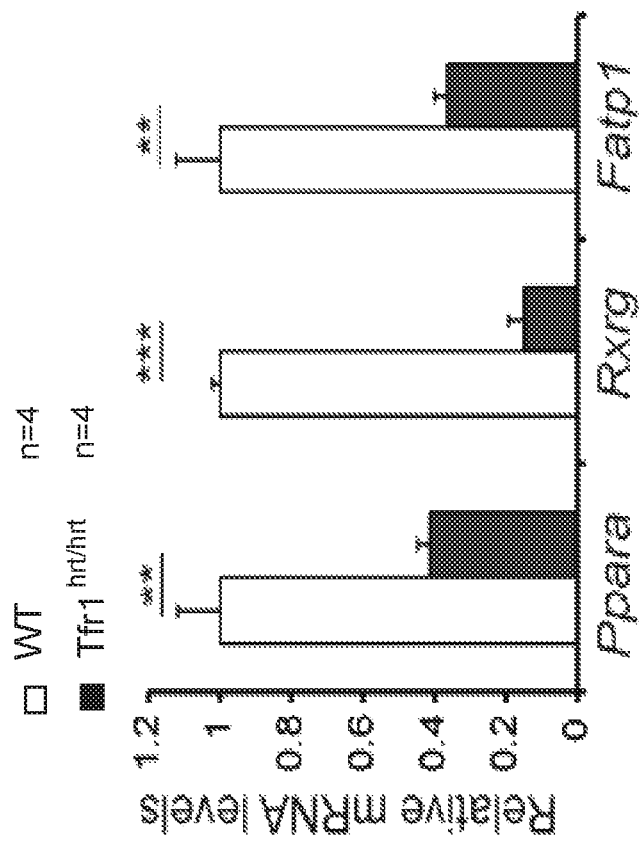

Cardiomyopathy is associated with a switch to fetal-like metabolism, with glucose, rather than fatty acids, as the preferred energy source. The switch has been attributed to decreased activity of PPARa (Ppara), which forms a heterodimer with Rxr. Expression of Ppara and Rxrg was decreased in Tfr1-null hearts, as was fatty acid transport protein (Fatp1/Slc27a1, FIG. 3F). Ppara expression is induced by the histone demethylase Kdm3a, which requires iron. Ppara and other genes induced by Kdm3a, Ucp2, and Acadm, had decreased mRNA levels (not shown) in Tfr1$^{hrt/hrt}$ mice. These results indicated that that iron deficiency caused decreased Ppara expression, contributing to the metabolic switch in Tfr1$^{hrt/hrt}$ mice.

Increased mRNA expression of hypoxia-inducible genes (FIG. 4A) and glycolytic enzymes (FIG. 4B) was observed at P10. Of the glycolytic enzymes, only PfkI was slightly increased at P5. Iron is a cofactor for hydroxylases that cause HIFa transcriptional regulators to be degraded and inactivated, indicating that iron deficiency may be explained by these results. In addition, Myc, which also induces expression of glycolytic enzymes, was upregulated (FIG. 4C). However, glycolysis was unlikely to meet energy needs of cardiomyocytes, which depend on mitochondrial respiration. Apoptosis was increased in Tfr1$^{hrt/hrt}$ hearts (FIG. 4D), consistent with severe mitochondrial dysfunction. Together, the results indicated that iron deficiency led to mitochondrial insufficiency, metabolic changes and increased apoptosis, contributing to cardiomyocyte hypertrophy and cardiac dysfunction in Tfr1$^{hrt/hrt}$ mice.

Example 5

Interruption of Mitophagy

Accumulation of damaged mitochondria should activate mitophagy to clear dysfunctional organelles and recover iron for re-use. Glycolytic enzyme Hk2 promotes autophagy during energy deprivation and was upregulated in Tfr1$^{hrt/hrt}$ hearts (FIG. 4B). Both isoforms of Rcan1, which also induces mitophagy and protects against apoptosis due to hypoxia, were upregulated in Tfr1$^{hrt/hrt}$ hearts (FIGS. 5A and 9A).

Figure 5C:
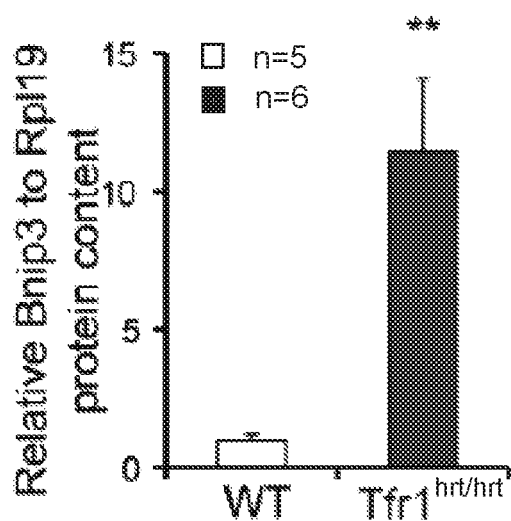
FIG. 5 shows altered expression of molecules involved in autophagy and mitophagy in hearts from Tfr1$^{hrt/hrt}$ mice. (A-G) Multiple autophagy- and mitophagy-related genes were examined in 10-day old heart samples for mRNA levels or, where feasible, for protein levels, as indicated in each panel. Differences indicated early induction of autophagy, but a failure to complete autophagy in hearts from Tfr1$^{hrt/hrt}$ mice. Samples sizes for WT and Tfr1$^{hrt/hrt}$: (E) 14 and 6 mice for LC3-II and Gabarap-II, respectively; and (G) 5-6 mice except for Atg4B (11 mice) and Atg3 (16 mice). (H) Lysosomal cathepsin D (Ctsd) and its cleaved intermediate were elevated in hearts from Tfrt1$^{hrt/hrt}$ mice, indicating normal lysosomal function. (I) Lpin1 mRNA was decreased in hearts from Tfr1$^{hrt/hrt}$ mice. (J) Optineurin (Optn) mRNA was increased in hearts from Tfr1$^{hrt/hrt}$ mice. Data were presented as means±SEM. Sample size (n) was indicated. *p<0.05, p<0.01, and *p<0.001 by one-way ANOVA; n.s. was not significant. See also FIG. 9.

Cardiomyocytes from young mice cannot be cultured, requiring mitophagy to be characterized using tissue samples. Expression of putative mitophagy receptors, Nix (Bnip31) and Fundc1, was decreased, rather than increased, in Tfr$^{hrt/hrt}$ hearts. Ulk1, a kinase that phosphorylates Fundc1 for clearance of damaged mitochondria, was also decreased (FIGS. 5B, 9B, and 9C). Bnip3, a homolog of Nix that can trigger opening of mitochondrial permeability transition pore and loss of mitochondrial membrane potential, was markedly increased in mutant hearts (FIGS. 5C and 9D). Bnip3 transcription is induced by hypoxia-inducible factors, and thus, its increase was consistent with the upregulation of other hypoxia-inducible genes as described above.

Figure 5D:
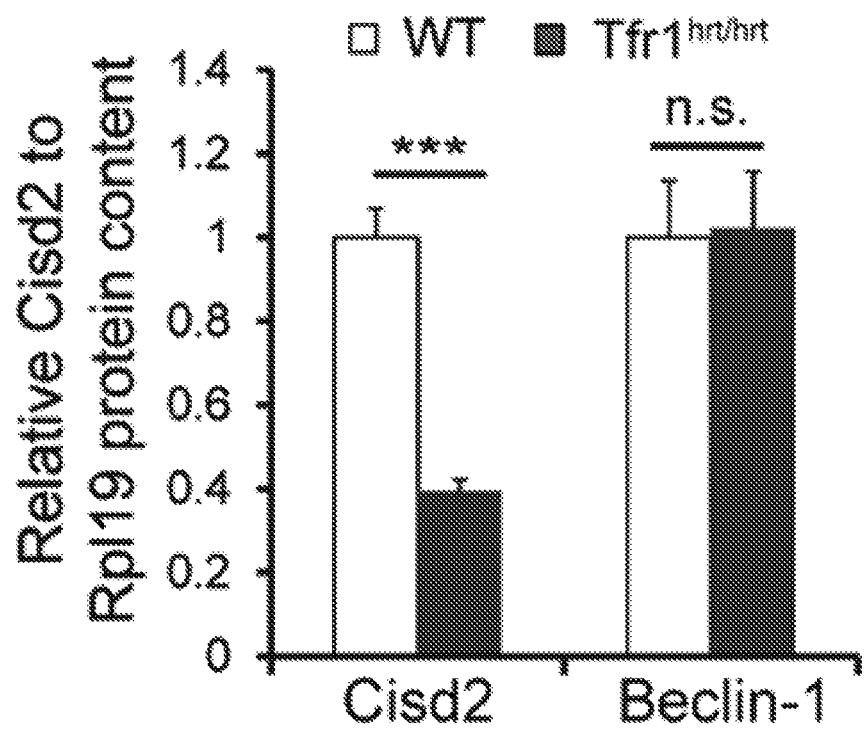
Figure 5E:
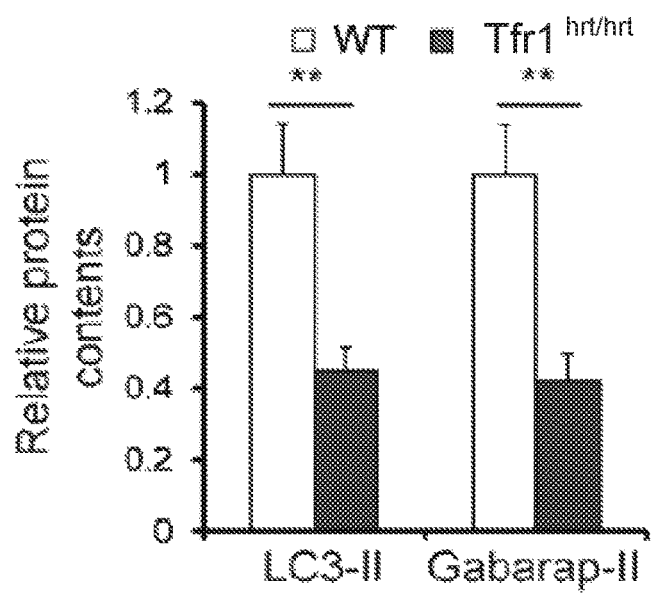
Figure 5F:
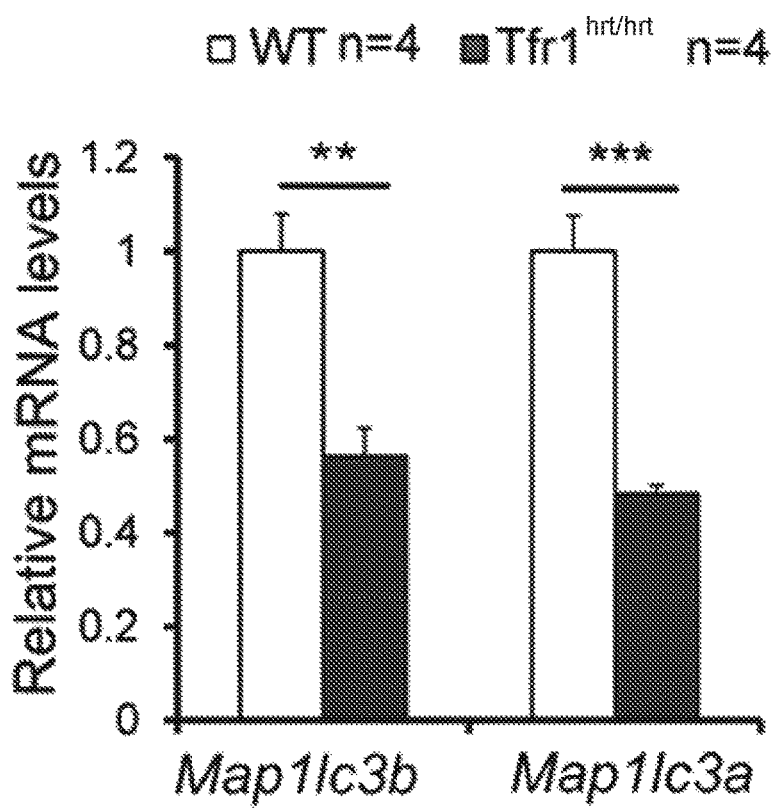
Figure 9:
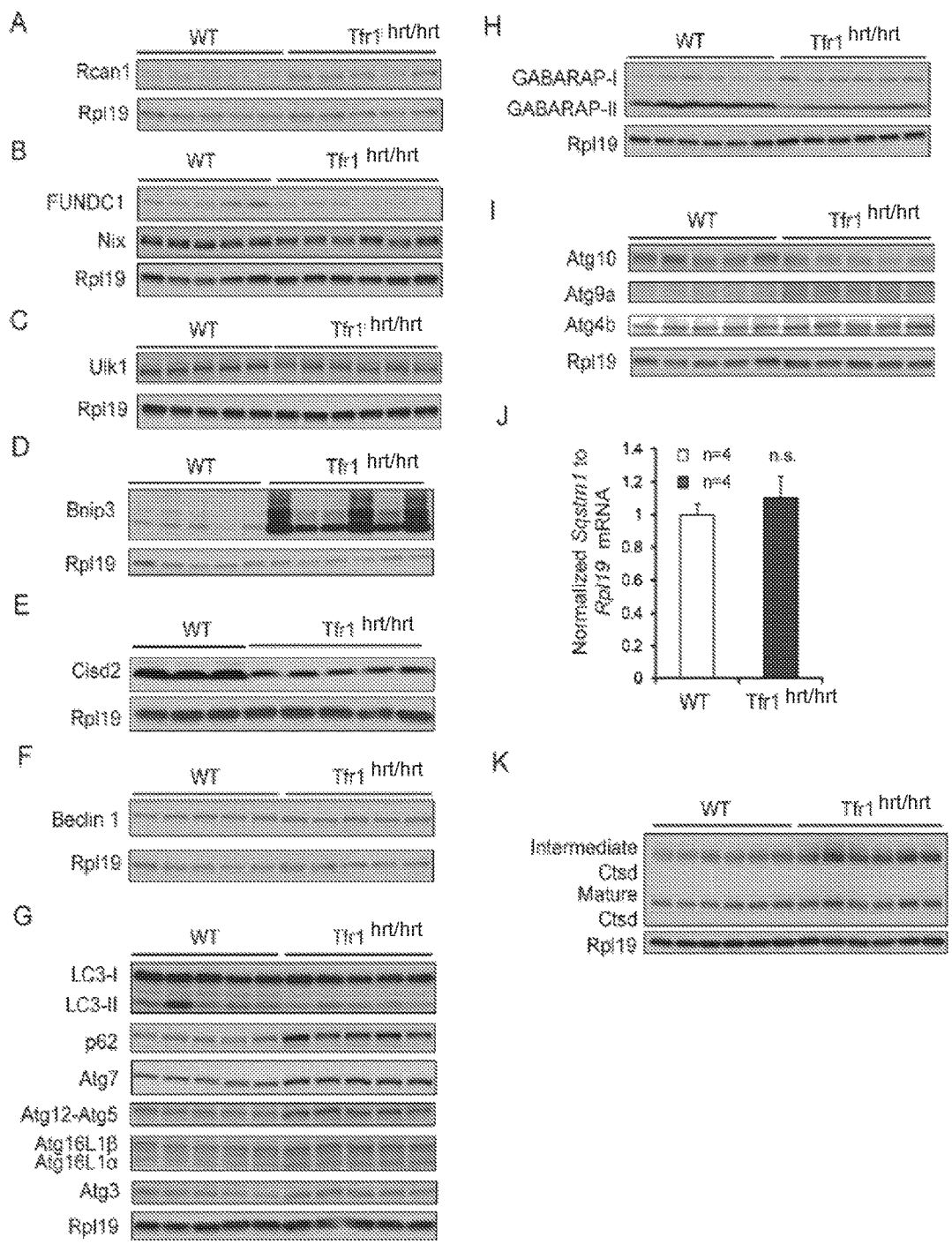
FIG. 9 shows immunoblot detection of proteins involved in autophagy and mitophagy in hearts from WT and Tfr1$^{hrt/hrt}$ mice (related to FIG. 5). (A-I) Multiple autophagy- and mitophagy-related proteins were examined by immunoblotting 10-day old littermate heart samples as indicated in each panel. (J) Normalized levels of p62 (Sqstm1) mRNA were similar in hearts from WT and Tfr1$^{hrt/hrt}$ littermates at 10 days of age. (K) Immunoblot showing increased Ctsd in hearts from Tfr1$^{hrt/hrt}$ mice. Data were presented as means±SEM. P-values were determined by one-way ANOVA. The sample size (n) was indicated: n.s., not significant.

Cisd2 (Naf-1), an Fe—S cluster protein associated with the mitochondrial membrane, was depleted in Tfr1$^{hrt/hrt}$ mice (FIGS. 5D and 9E). Cisd2 is important for mitochondrial maintenance and oxidative phosphorylation and control of autophagy. Deficiency of Cisd2 should promote autophagy by liberating Beclin-1 from Bcl2. Beclin-1 levels were similar in mutant and WT hearts (FIGS. 5D and 9F), but its activity could not be assessed.

Map1lc3 (LC3) and Gabarap are also involved in the cargo recognition step of autophagy (FIGS. 5E, 5F, 9G, and 9H). LC3-II, a phosphatidylethanolamine (PE)-conjugated form of LC3, increases during active autophagy, but was decreased in heart samples from Tfr1$^{hrt/hrt}$ mice. Gabarap-II was also decreased.

Other proteins involved in early steps of autophagy were evaluated to explore why mitophagy was ineffective (FIGS.

5G, 9G, and 9I). Atg16L, which was increased in Tfr1$^{hrt/hrt}$ mice, is involved early in the formation of the phagophore, forming a complex with Atg12 and Atg5. Atg10, which was decreased in mutant hearts, is an E2-like enzyme involved in Atg12-Atg5 conjugation and LC3 conjugation to PE. Atg12-Atg5 was increased in mutant hearts, though LC3-II was decreased. The Atg12-Atg5 complex forms before conjugation of LC3. Knockdown of LC3 or Gabarap leads to maintenance of the Atg12-Atg5 complex, which was consistent with observations described herein. Atg4b cleaves the carboxyl termini of pro-forms of LC3 and Gabarap to expose their lipidation sites, but it also de-lipidates both proteins. Overexpression of Atg4b thus inhibits membrane localization and PE conjugation of LC3. Atg4b was increased in Tfr1$^{hrt/hrt}$ hearts, contributing to decreased levels of LC3-II and Gabarap-II. Atg7, an E1-like enzyme for ubiquitin-like conjugation systems involved in the development of autophagosomes, and Atg3, an E2-like enzyme for the LC3/Gabarap conjugation system, were both increased in Tfr1$^{hrt/hrt}$ mice. Overall, these results indicated that the mutant heart cells were attempting to initiate mitophagy appropriately, but key proteins involved in cargo recognition appeared to be deficient.

Sqstm1 (p62) is a molecule that links the phagophore to cargo. During normal autophagic flux, p62 is degraded by lysosomal enzymes. However, it was increased in Tfr1$^{hrt/hrt}$ hearts (FIGS. 5G and 9G), even though p62 mRNA was not increased (FIG. 9J), indicating that p62 accumulated because it was not degraded. Cathepsin D (Ctsd), an indicator for lysosomal function, was also examined. Both intermediate and mature forms of Ctsd were increased in hearts from Tfr1$^{hrt/hrt}$ mice (FIGS. 5H and 9K), showing that lysosomes were functioning. These results indicated that a mitophagy step prior to lysosomal fusion was impaired.

Lipin1 (Lpin1) enhances transcription regulated by Ppar-a and PGC-1a and controls autophagic clearance in skeletal muscle. Lipin1 deficiency in skeletal muscle leads to accumulation of p62, similar to what was observed and described above. Lpin1 mRNA was decreased in hearts from Tfr1$^{hrt/hrt}$ mice (FIG. 5I), contributing both to the metabolic switch and to the interruption of mitophagy.

Figure 4A:
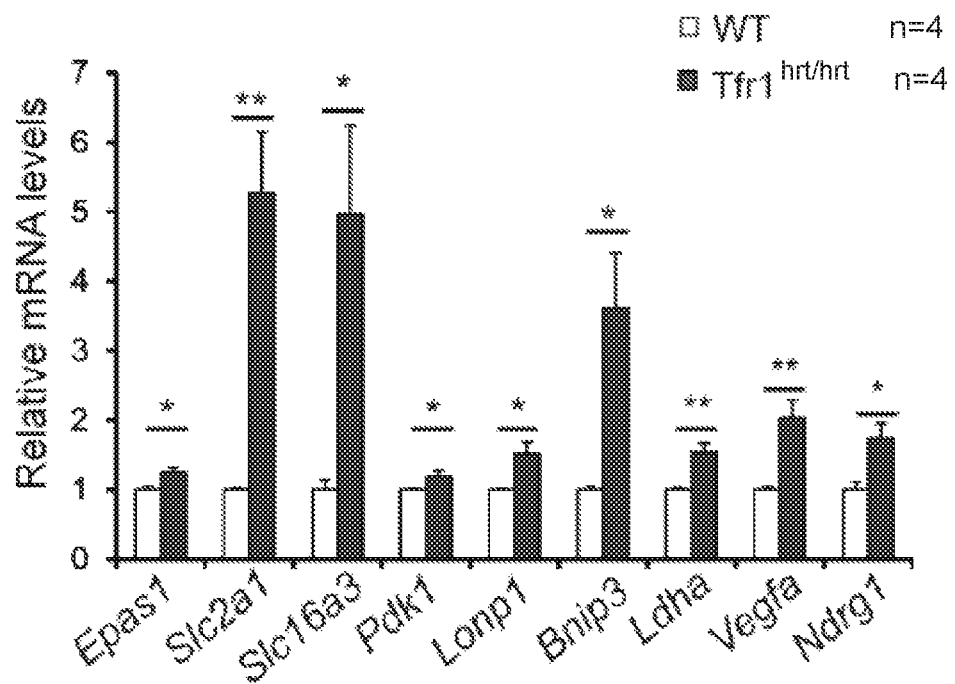
FIG. 4 shows metabolic changes and increased apoptosis in hearts from Tfr1$^{hrt/hrt}$ mice at P10. (A) Relative mRNA levels of transcripts induced by hypoxia. (B) Relative mRNA levels of transcripts encoding enzymes of glycolysis. (C) Relative level of Myc mRNA. (D) TUNEL staining for apoptosis. Top row without DAPI staining of nuclei; bottom row with DAPI staining. Vertical pairs of panels from left to right: negative control, positive control, WT, and Tfr1$^{hrt/hrt}$. Bright green fluorescent nuclei represented apoptotic cells; scale bars=100 µm. Results were quantified on the right; data were presented as means±SEM. Sample size (n) was indicated. *p<0.05; p<0.01; and *p<0.001 by one-way ANOVA.
Figure 4B:
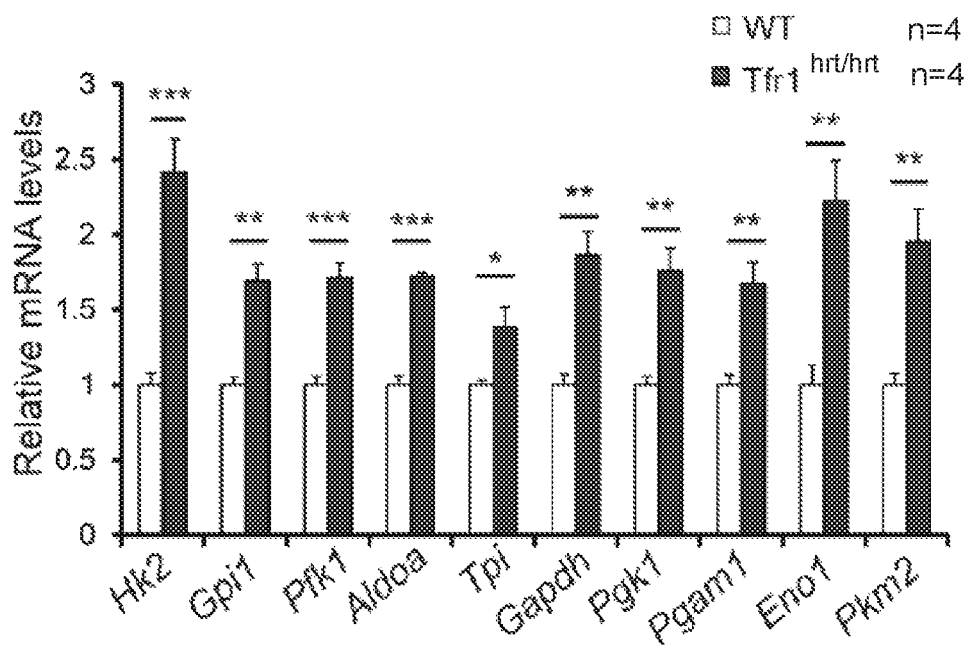
Figure 4C:
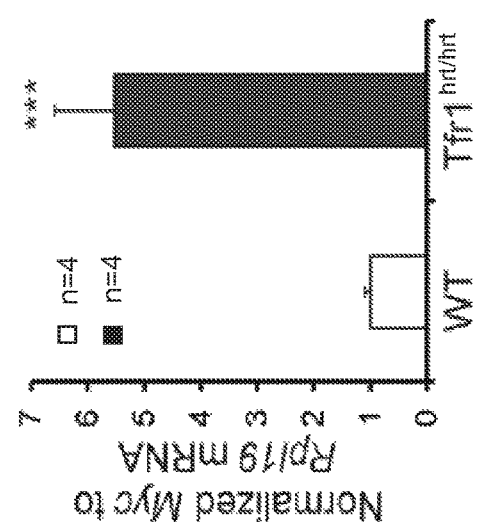
Figure 4D:
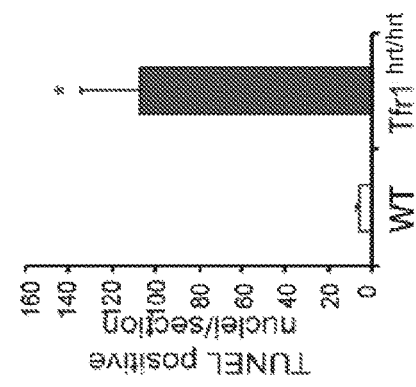
Figure 4D:
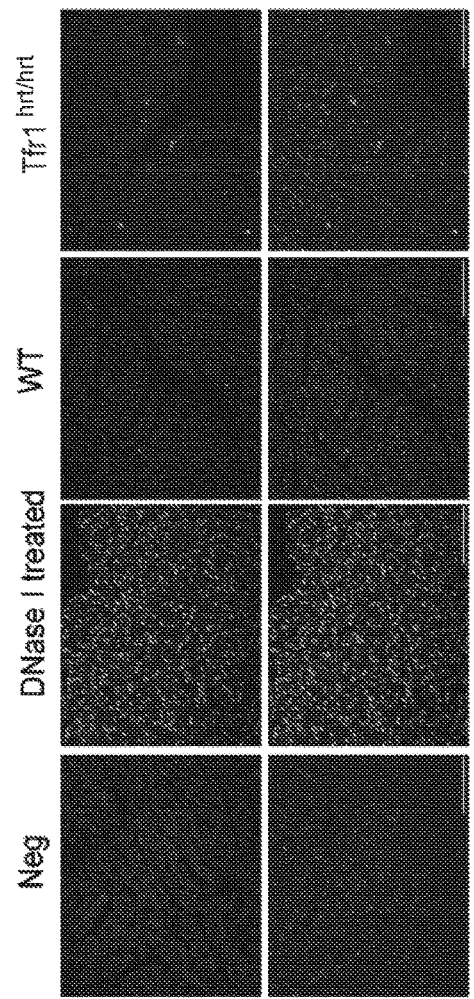

Ndrg1 is induced by iron depletion and was upregulated in Tfr1$^{hrt/hrt}$ hearts (FIG. 4A). It co-localizes with Tfr1 in late and recycling endosomes. Overexpression of Ndrg1 accelerates Tfr1 recycling and suppresses LC3-II accumulation and autophagosome formation. Although it cannot affect Tfr1 in the Tfr$^{hrt/hrt}$ mutants, it may contribute to the block in mitophagy.

Figure 5G:
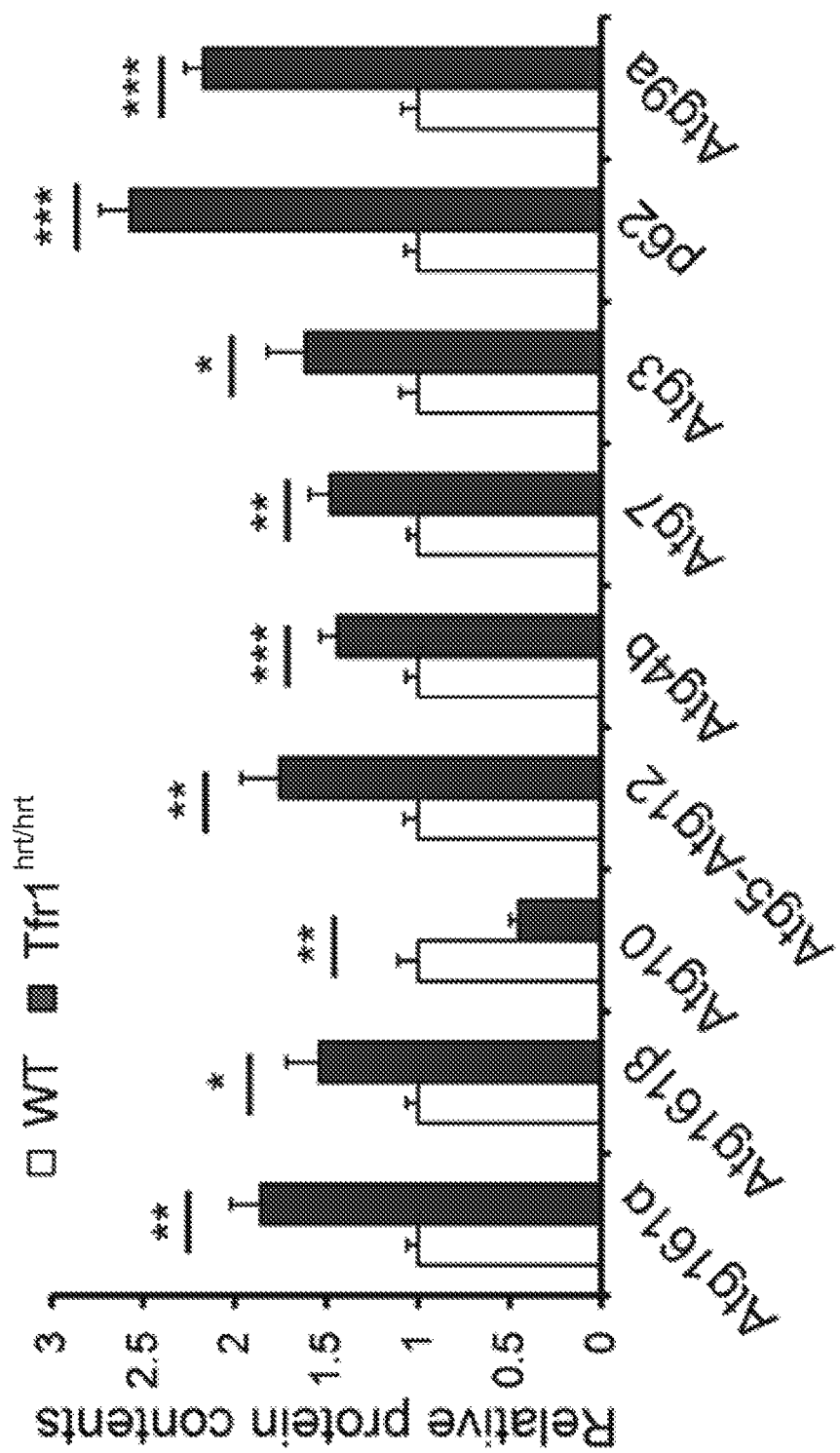
Figure 5H:
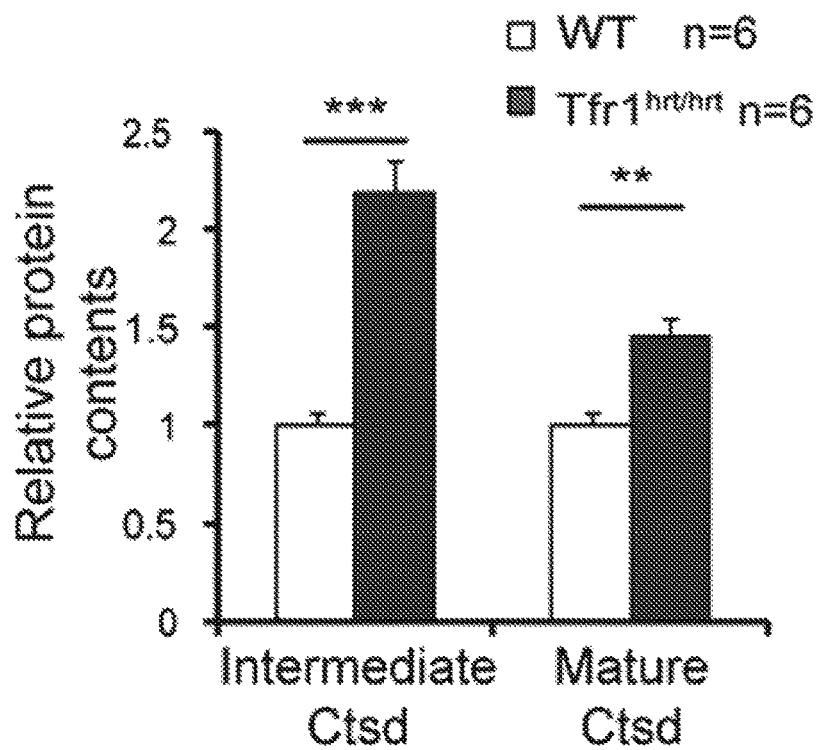
Figure 5I:
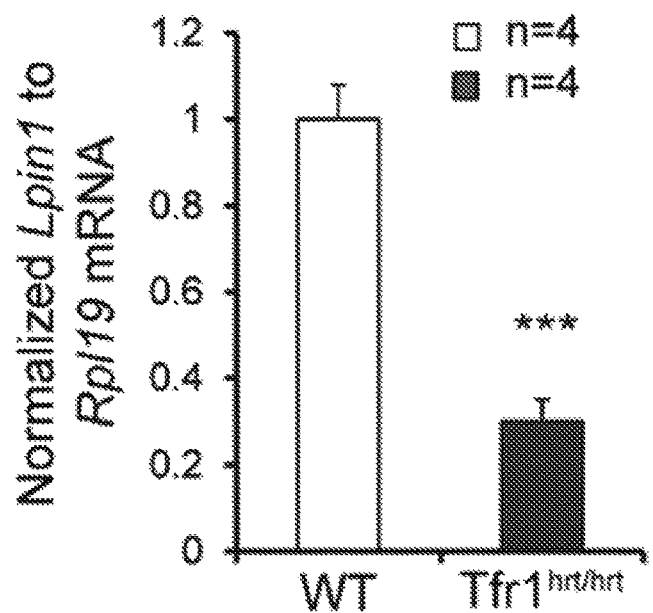
Figure 5J:
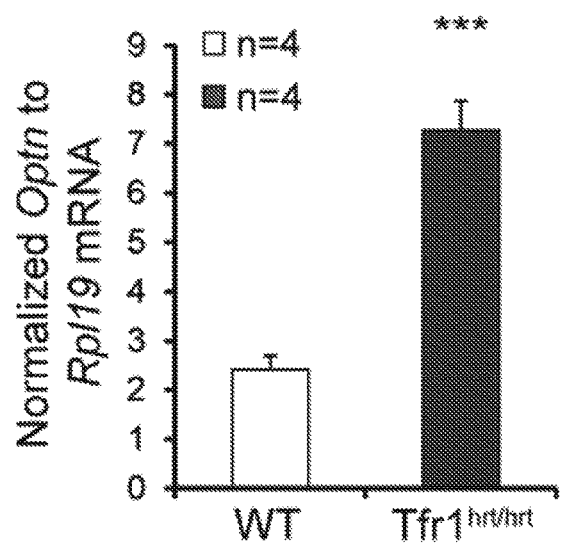

Atg9 traffics with Tfr1 and may deliver membrane components to developing autophagosomes. Atg9 was increased in Tfr1$^{hrt/hrt}$ hearts (FIGS. 5G and 9I). Optn, also important in autophagosome maturation, was markedly induced in Tfr$^{hrt/hrt}$ hearts (FIG. 5J). Optineurin interacts with Tfr1 to modulate subcellular localization and Tf uptake. Accordingly, both Atg9 and Optn may have roles in the Tf cycle, and lack of Tfr1 resulted in compensatory upregulation, perturbing normal mitophagy.

Example 6

Rescue of Tfr1$^{hrt/hrt}$ Mice

While it was observed that Tfr1 deletion resulted in cardiac iron deficiency and mitochondrial dysfunction, it was also possible that the mutant phenotype resulted from abrogation of an alternative role of Tfr1, or from both loss of such a role and iron deficiency. As such, two approaches were used to address this question—it was attempted to rescue the Tfr1$^{hrt/hrt}$ phenotype by co-expressing a Tfr1 mutant protein that cannot bind Tf and, in parallel, by inducing iron overload in Tfr1$^{hrt/hrt}$ mice.

Mice expressing a mutant Tfr1$^{R654A}$ protein from the ubiquitously transcribed Rosa26 locus was developed and it was shown that Tfr1$^{R654A}$ was unable to bind Tf for iron uptake. Breeding was used to obtain Tfr1$^{hrt/hrt}$; Tfr1$^{R61A}$ mice, which had cardiomyocytes lacking WT Tfr1 but expressing mutant Tfr1$^{R654A}$, and compared them to Tfr1$^{fl/fl(+)}$; Tfr1$^{R654A}$ control mice. Because R654A Tfr1 cannot assimilate Tf-bound iron, hearts from Tfr1$^{hrt/hrt}$; Tfr1$^{654A}$ mice should be iron deficient, but should express an otherwise intact form of Tfr1 that differed from WT Tfr1 by only one amino acid in the extracellular domain. If the phenotype of Tfr1$^{hrt/hrt}$ mice was due wholly or in part to loss of a function of Tfr1 unrelated to iron uptake, expression of Tfr1$^{R654A}$ might fully or partially rescue the mutant phenotype.

Figure 6A:
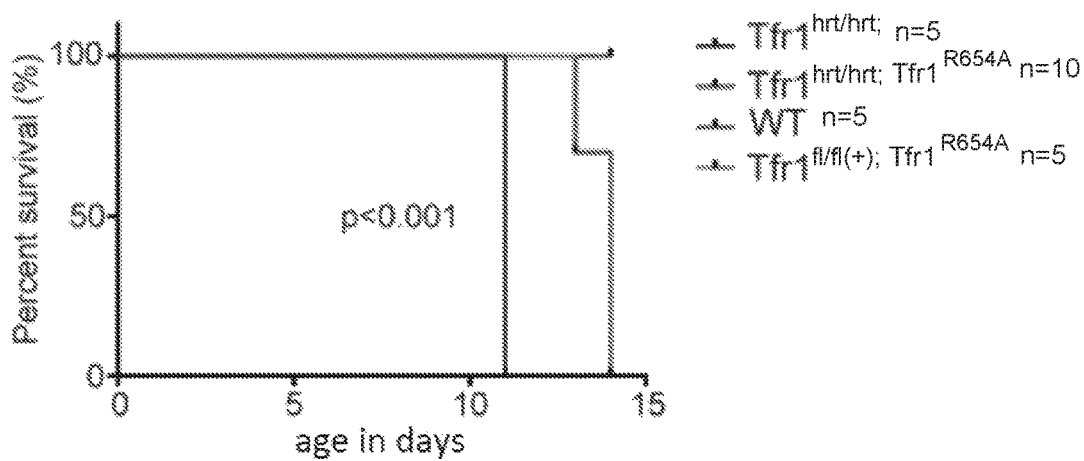
FIG. 6 shows attempts to rescue Tfr1$^{hrt/hrt}$ mice. (A) R654A Tfr1 prolonged lifespan of Tfr1$^{hrt/hrt}$ mice by several days. P-value was determined by the LogRank test. Sample size (n) was indicated. (B,C) Similar to Tfr1$^{hrt/hrt}$ mice, Tfr1$^{hrt/hrt}$ mice constitutively expressing R654A Tfr1 were iron deficient and accumulated p62 in the heart, but appeared to have normal levels of LC3-II and Atg10. (D,E) Iron overload achieved by Fe dextran administration at P3 and an Hjv−/− hemochromatosis background provided sufficient iron to fully rescue Tfr1$^{hrt/hrt}$ mice, restoring Fe—S proteins Dpyd and Ppat as well as the iron storage protein H-ferritin and ETC complexes at 10 weeks of age. (F) There was no difference in markers of autophagy between iron-loaded Tfr1$^{hrt/hrt}$ mice and their similarly iron-loaded littermate controls at 10 weeks of age. See also FIG. 10.
Figure 6B:
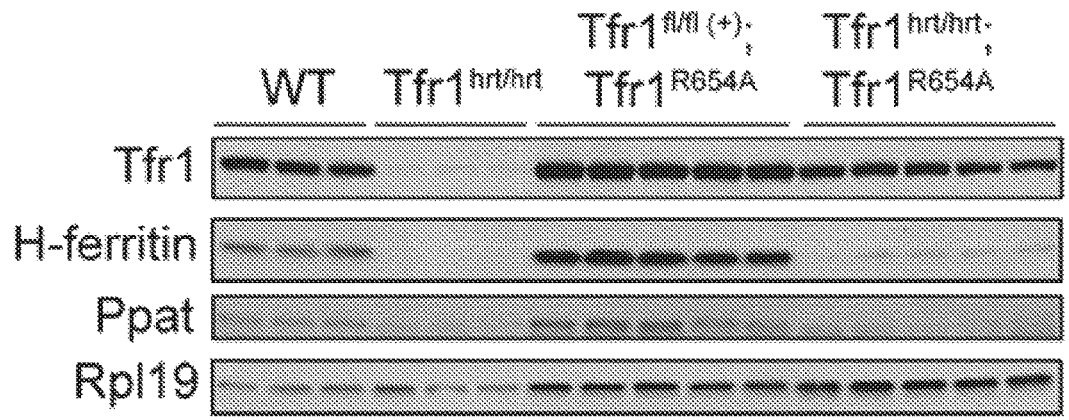
Figure 6C:
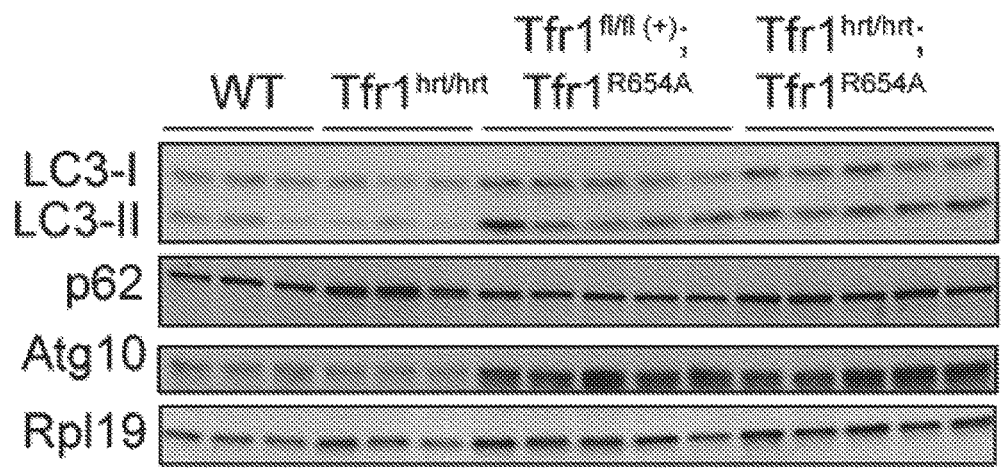

Tfr1$^{hrt/hrt}$; Tfr1$^{R64A}$ mice died at P13 to P14, later than Tf1$^{hrt/hrt}$ mice (FIG. 6A). Immunoblots confirmed expression of mutant Tfr1 (FIG. 6B). H-ferritin and Ppat were similarly decreased in Tfr1$^{hrt/hrt}$ mice at P10 and Tfr1$^{hrt/hrt}$; Tfr1$^{R654A}$ mice at P12, indicating that Tfr1$^{hrt/hrt}$; Tfr1$^{R64A}$ mice were iron deficient as expected (FIG. 6B). However, amounts of LC3-II and Atg10 in hearts from Tfr1$^{hrt/hrt}$; Tfr1$^{R654A}$ mice were similar to Tfr1$^{fl/fl(+)}$; Tfr1$^{R654A}$ hearts, indicating that some aspects of mitophagy were ameliorated (FIGS. 6C, 14A, and 14C). Nonetheless, p62 still accumulated, indicating a persistent defect in mitophagy (FIGS. 6C and 14B). These results indicated that iron deficiency was the major cause of the Tfr1$^{hrt/hrt}$ phenotype. However, a contribution of Tfr1, independent of Tf binding, may explain why death of Tfr1$^{hrt/hrt}$; Tfr1$^{R654A}$ mice occurred later than Tfr1$^{hrt/hrt}$ mice.

Figure 10:
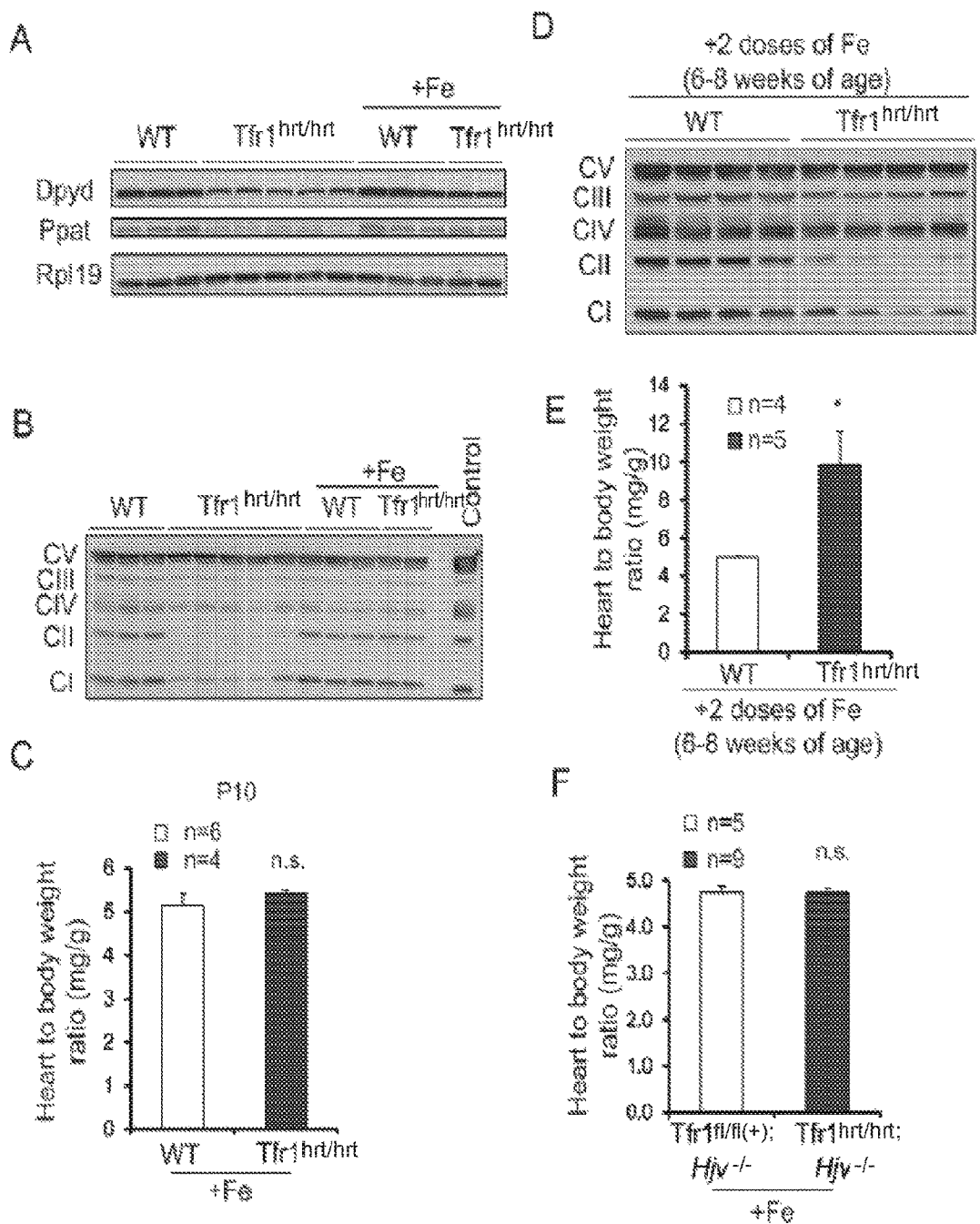
FIG. 10 shows ongoing iron loading was necessary to rescue Tfr1$^{hrt/hrt}$ (related to FIG. 6). (A) Amounts of Fe—S cluster proteins Dpyd and Ppat in hearts from 10-day old WT and Tfr1$^{hrt/hrt}$ mice untreated or treated with iron dextran. (B) Representative ETC complex proteins in hearts from 10-day old WT and Tfr1$^{hrt/hrt}$ mice untreated or treated with iron dextran. (C) Heart weight to body weight ratios at P10 for WT and Tfr1$^{hrt/hrt}$ littermates treated with 1 dose of iron dextran treated on P3. (D) Representative ETC complex proteins in hearts from 6-8 week old WT and Tfr1$^{hrt/hrt}$ mice treated with 2 doses of iron dextran (at P3 and P7). (E) Heart weight to body weight ratios at 6-8 weeks from WT and Tfr1$^{hrt/hrt}$ mice treated with 2 doses of iron dextran (at P3 and P7). (F) Heart to body weight ratios at 10-11 weeks from Tfr1$^{fl/fl(+)}$; Hjv−/− and Tfr1$^{hrt/hrt}$; Hjv−/− mice treated with iron dextran only at P3. Data were presented as means±SEM. P-values were determined by one-way ANOVA. The sample size (n) was indicated. *p<0.05; n.s., not significant.

To test whether cardiac iron repletion could rescue Tfr1$^{hrt/hrt}$ mice, a large dose of iron dextran was administered at P3, to supersaturate circulating Tf and induce non-Tf-bound iron uptake. This prolonged survival, but Tfr1$^{hrt/hrt}$ mice still died at 4 to 5 weeks with severe cardiomegaly. It was confirmed that the hearts had assimilated iron by immunoblotting for Fe—S cluster proteins. In contrast to untreated Tfr1$^{hrt/hrt}$ mice, Dpyd and Ppat levels were similar at P10 in Tfr1$^{hrt/hrt}$ and WT mice treated with iron dextran (FIG. 10A). Proteins representing ETC complexes were also similar at P10 (FIG. 10B). At that time, Tfr1$^{hrt/hrt}$ mice and WT littermates had similar heart to body weight ratios (FIG. 10C). A second dose of iron dextran was next administered at P7. The onset of the cardiomyopathy phenotype was further delayed and Tfr1$^{hrt/hrt}$ mice survived up to 13 weeks. However, ETC complexes were already decreased in hearts from Tfr1$^{hrt/hrt}$ mice at 6-8 weeks of age (FIG. 10D) and the hearts were already enlarged (FIG. 10E). Together, these results indicated that iron-treated Tfr1$^{hrt/hrt}$ mice assimilated and used the supplemental iron to survive beyond their usual lifespan. However, they eventually showed abnormalities in mitochondrial ETC complexes and autophagy-related proteins similar to, but more pronounced than, untreated Tfr1$^{hrt/hrt}$ mice at P10 (not shown).

It was hypothesized that the heart might require continuous iron uptake, and that iron administered early might no longer be available. To sustain elevated plasma iron concentrations, the hemojuvelin knockout (Hjv$^{-/-}$) mice were used, which persistently have increased non-Tf-bound iron. Tfr1$^{hrt/hrt}$; Hjv$^{-/-}$ mice were generated, in which Tfr1 was deleted in the heart and Hjv was deleted globally. These mice also died at P11, similar to Tfr1$^{hrt/hrt}$ mice. However, the Hjv$^{-/-}$ background did not allow for substantial iron accumulation during the neonatal period. Therefore, Tfr1$^{hrt/hrt}$ and control mice were treated with iron dextran at P3 to support the animals until the Hjv mutation caused elevated iron levels. With this strategy, the Tfr1$^{hrt/hrt}$; Hjv$^{-/-}$ mice had lifespans (not shown) and heart to body weight ratios (FIG. 10F) similar to Tfr1$^{fl/fl\ (+)}$; Hjv$^{-/-}$ controls.

Figure 6D:
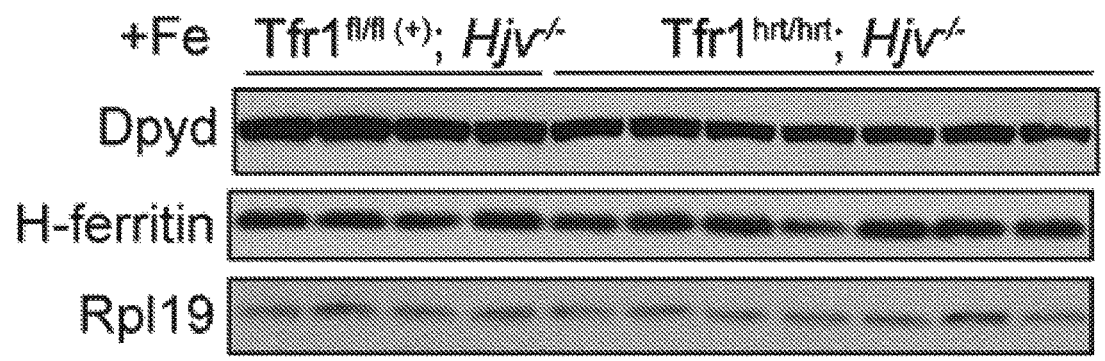
Figure 6E:
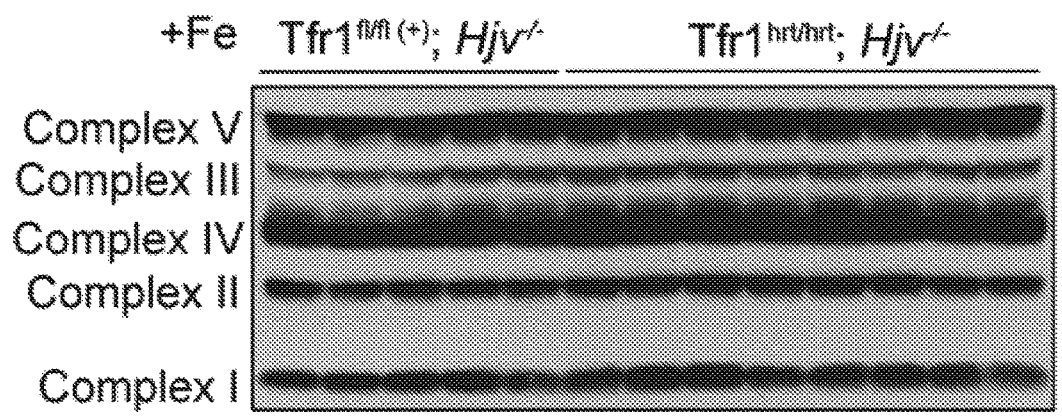
Figure 6F:
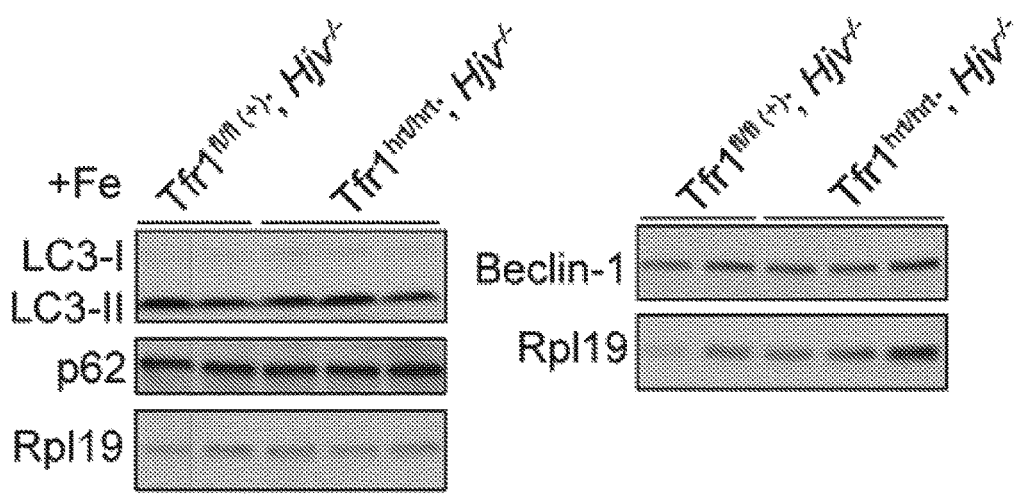

It was confirmed that this experimental protocol had restored cardiomyocyte iron by immunoblotting for Dypd and ferritin at 10-11 weeks of age (FIG. 6D). Amounts of markers for ETC complexes I to IV were also indistinguishable between Tfr1$^{hrt/hrt}$; Hjv$^{-/-}$ mice and controls (FIG. 6E). Autophagy-related proteins LC3-II, p62, and Beclin-1 showed no significant differences (FIG. 6F). Collectively, these results indicated that the Tfr1$^{hrt/hrt}$ mutant phenotype was primarily attributable to a defect in iron assimilation, and iron deficiency played a critical role in development of cardiac hypertrophy, mitochondrial dysfunction and interruption of mitophagy. Importantly, it appeared that the heart was highly sensitive to iron deprivation due to inactivation of Tfr1.

Example 7

Treatment with Nicotinamide Riboside (NR)

Mitochondrial dysfunction can cause a decreased NAD/NADH ratio and inactivation of sirtuin deacetylases. A decreased NAD/NADH ratio may block signals for mitochondrial biogenesis while also causing defective mitophagy. Deacetylase activity is important for deacetylation of autophagy-related proteins; in the absence of Sirt1, LC3-II is decreased and p62 accumulates. This was similar to what was observed in Tfr1$^{hrt/hrt}$ mice as described above. It was hypothesized that augmentation of NAD levels might modify the mutant phenotype.

Figure 7A:
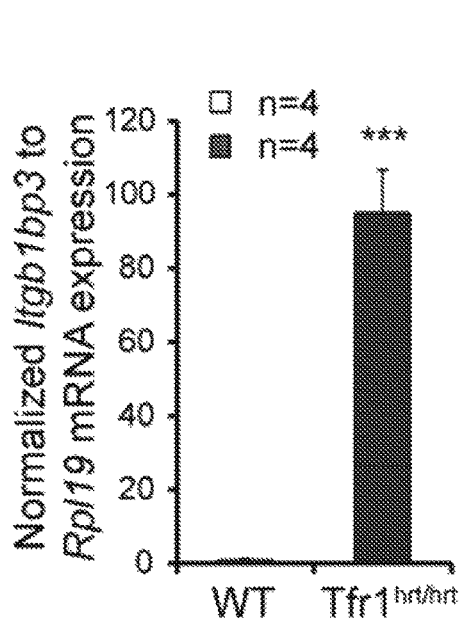
FIG. 7 shows Tfr1$^{hrt/hrt}$ mice were transiently rescued by treatment with nicotinamide riboside (NR). (A) mRNA encoding Nmrk2/ltgb 1bp3 was massively increased in Tfr1$^{hrt/hrt}$ mice. (B) mRNAs encoding Slc3a2 and Slc7a5, components of the uptake system for tryptophan, an NAD precursor, were increased in Tfr1$^{hrt/hrt}$ mice. (C) mRNAs encoding ADP-ribosyltransferases Art1, Art4, and Art5 were decreased in Tfr1$^{hrt/hrt}$ mice. (D) Mitochondrial proteins from hearts of Tfr1$^{hrt/hrt}$ mice showed increased lysine acetylation. (E) Administration of the NAD precursor and Nmrk2 substrate NR extended the lifespan of Tfr1$^{hrt/hrt}$ mice for up to 5 days. Data were presented as means±SEM. P-values for (A) to (C) were determined by one-way ANOVA. Sample size (n) was indicated; *p<0.05 and ***p<0.001. P-vale for (E) was determined by LogRank test.
Figure 7B:
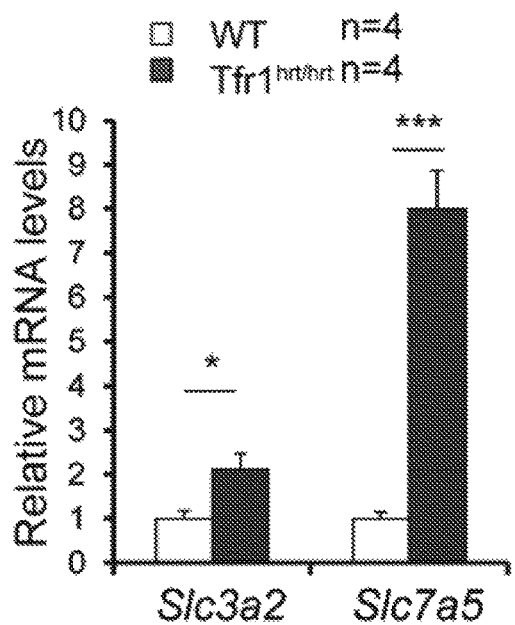
Figure 7C:
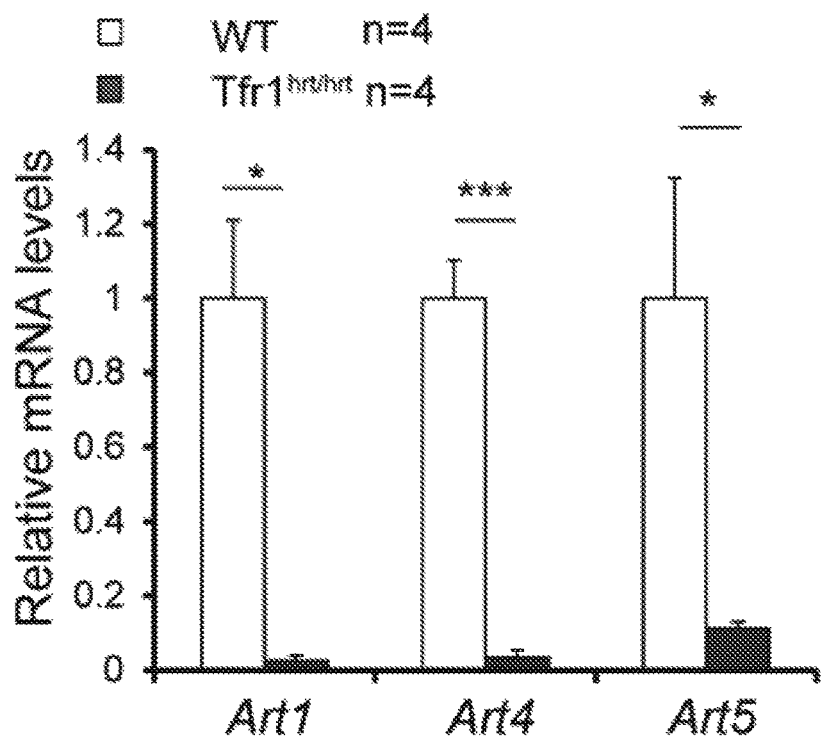
Figure 7D:
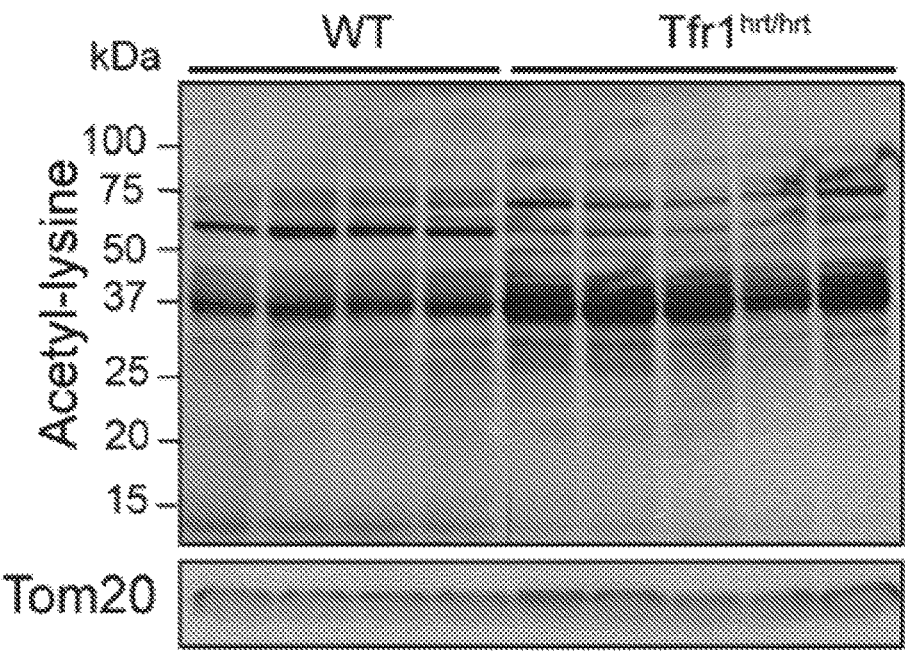

Induction of mRNA encoding nicotinamide riboside kinase 2 (Nmrk2/Itgb1bp3, FIG. 7A) and the transport system for the NAD precursor tryptophan, Slc3a2/Slc7a5 (FIG. 7B), along with decreased expression of ADP-ribosyltransferases (FIG. 7C) was observed, indicating that mutant cardiomyocytes used multiple approaches to try to increase cellular NAD levels. Mitochondria from Tfr1$^{hrt/hrt}$ hearts showed increased lysine acetylation (FIG. 7D), consistent with decreased mitochondrial sirtuin deacetylase activity due to decreased mitochondrial NAD.

Figure 7E:
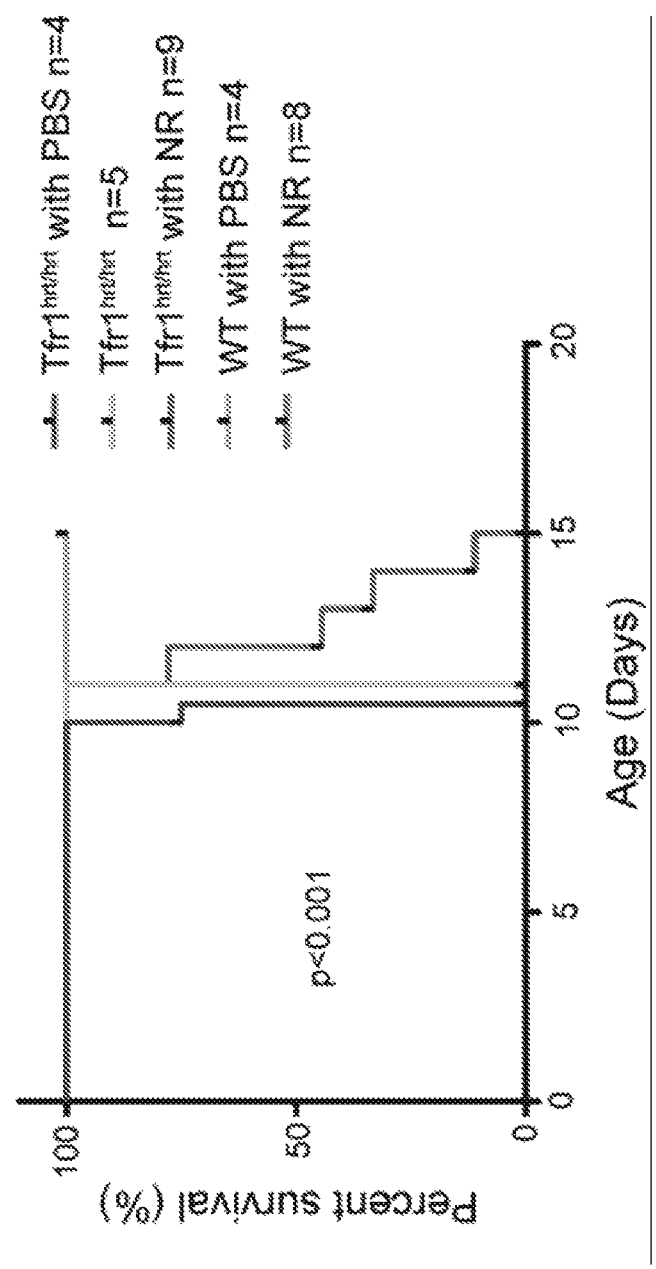
Figure 16:
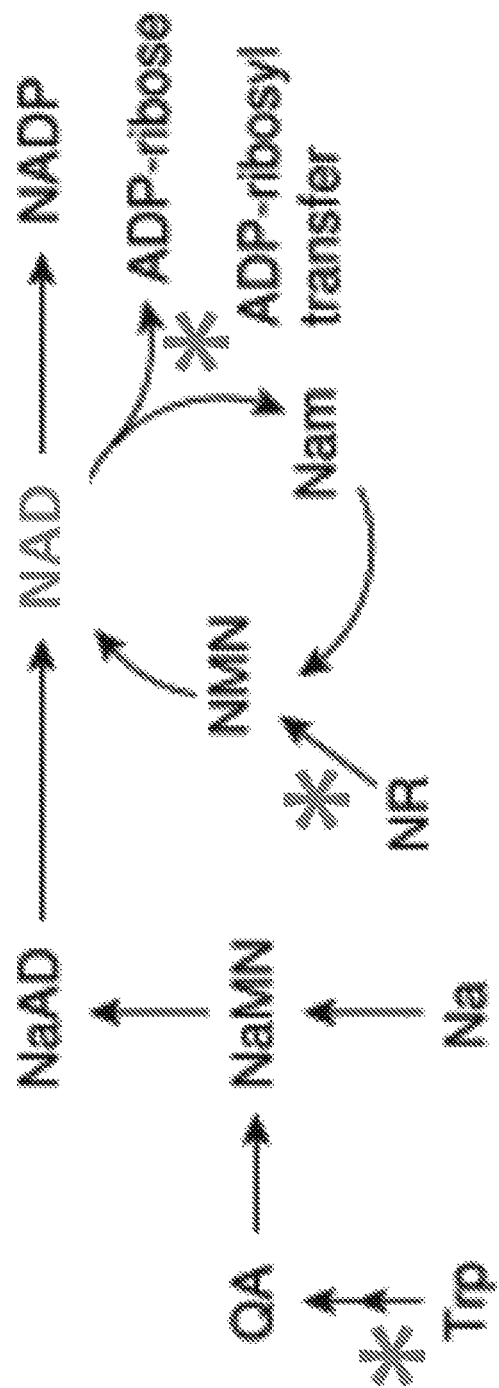
FIG. 16 shows a schematic of nicotinamide riboside (NR) feeding into the pathway for synthesizing NAD.

NR can be phosphorylated by Nmrk proteins to induce NAD production, activating sirtuins and mitochondrial biogenesis. How NR feeds into the synthetic pathway for NAD production is shown in FIG. 16. Noting that Nmrk2 (Itgb1bp3) was markedly upregulated in Tfr1$^{hrt/hrt}$ mice (FIG. 7A), it was hypothesized that this form of vitamin B3 may benefit the mutant animals, even though it should not impact iron deficiency. NR or vehicle was administered to young animals and up to 50% prolongation of lifespans of Tfr1$^{hrt/hrt}$ mice was observed (FIG. 7E), indicating that NR contributed to NAD production and ameliorated the phenotype.

Figure 19:
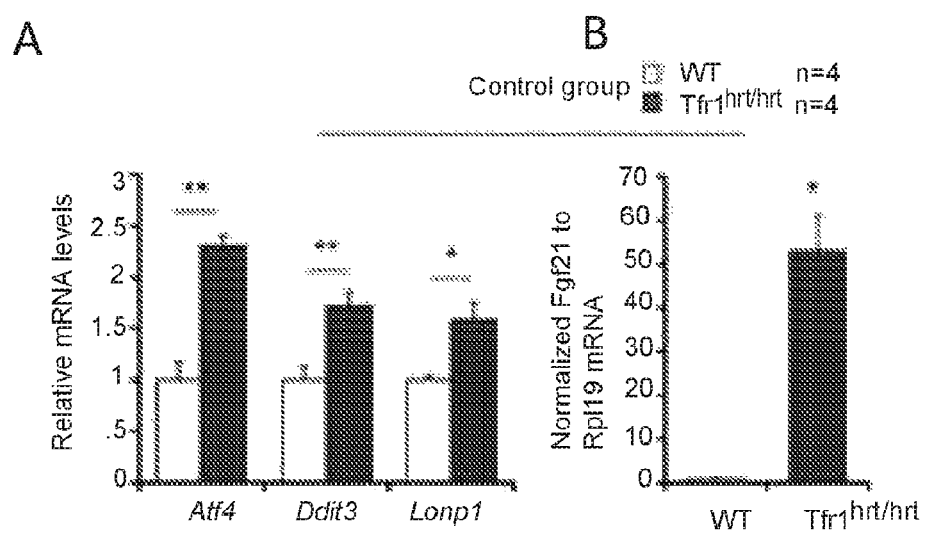
FIG. 19 shows the levels of $UPR^{MT}$ mRNAs in hearts from WT and $Tfr1^{hrt/hrt}$ mice untreated (A) or treated with NR (B). NR treatment appears to have blunted the UPRMT response.
Figure 20:
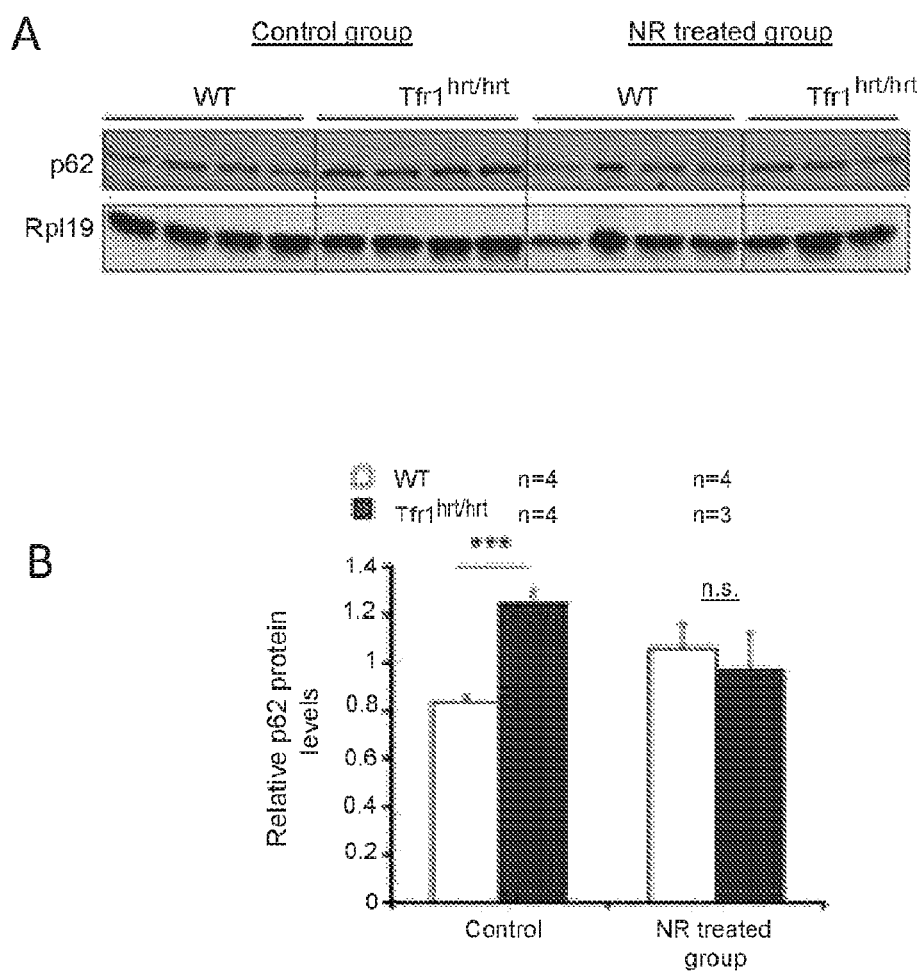
FIG. 20 shows p62 protein levels in hearts from WT and $Tfr1^{hrt/hrt}$ mice that were untreated (A) or treated with NR (B).

It was hypothesized that NR might improve the NAD/NADH ratio by increasing NAD. NAD/NADH ratios were measured with and without NR treatment but measurements from tissue were inconclusive. Alternatively, it was hypothesized that NR may enhance the mitochondrial unfolded protein response (UPR$^{MT}$). Although not apparent at P5 (not shown), increased mRNA for multiple genes associated with the UPR$^{MT}$ in P10 hearts was observed, including Atf4, Lonp1, Ddit3 and Fgf21 (FIGS. 19A and 19B). NR treatment was associated with decreased expression of UPRMT mRNAs (FIGS. 19A and 19B). Furthermore, NR alleviated the accumulation of p62 in the Tfr1$^{hrt/hrt}$ hearts (FIGS. 20A and 20B).

Figure 17:
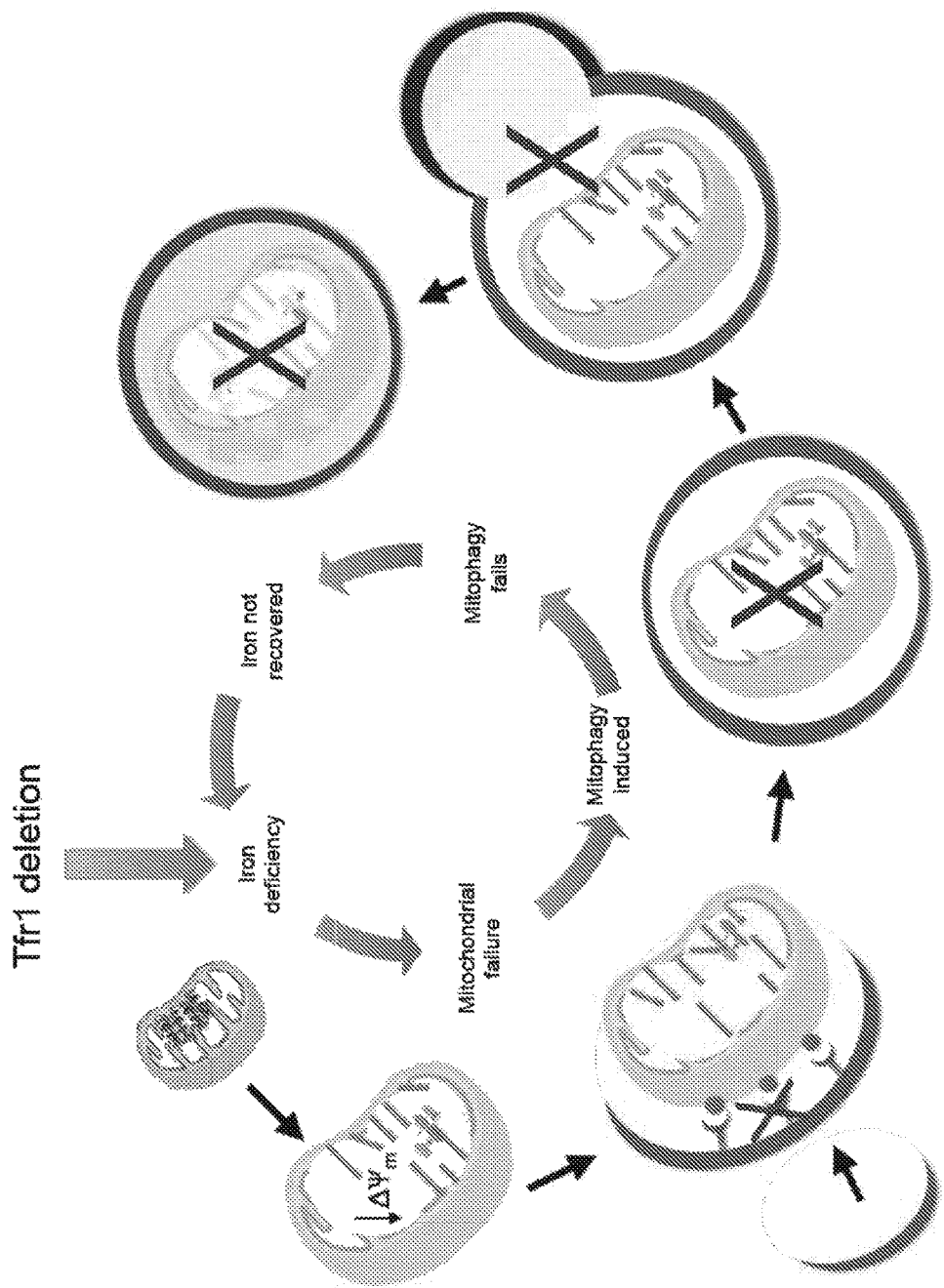
FIG. 17 shows a schematic of how deletion of Tfr1 in the heart leads to iron deficiency, which in turn, leads to mitochondrial dysfunction and defective mitophagy. Defective mitophagy did not allow for the recovery of iron from dysfunctional mitochondria.

In summary, Examples 1-7 demonstrated that mice lacking Tfr1 in the heart died in the second week of life, with cardiomegaly, poor cardiac function, failure of mitochondrial respiration, and interrupted mitophagy. In this interrupted mitophagy, mitophagy was induced, but failed due to a block at the cargo recognition step. This failure of mitophagy led to iron not being recovered from dysfunctional mitochondria for re-use by cardiomyocytes. Accordingly, the interrupted mitophagy was caused by iron deficiency, but also contributed to ongoing iron deficiency (FIG. 17).

The phenotype of the mice lacking Tfr1 in the heart was only rescued by aggressive iron therapy, which overwhelmed the capacity of serum Tf to bind iron. The phenotype was ameliorated by expression of an iron uptake-incompetent Tfr1 (i.e., Tfr1$^{R564A}$) or administration of nicotinamide riboside, an NAD precursor. Nicotinamide riboside increased the lifespan of treated mice in the absence of iron therapy, and thus, may be a therapeutic approach for patients with heart failure complicated by iron deficiency.

6. Clauses

Clause 1. A method for treating heart failure in a subject in need thereof, the method comprising administering a therapeutically effective amount of nicotinamide riboside to the subject.

Clause 2. The method of clause 1, wherein the subject has iron deficiency.

Clause 3. The method of clause 1, wherein the subject has iron deficiency in the heart.

Clause 4. The method of clause 1, wherein the subject has iron deficiency with anemia.

Clause 5. The method of clause 1, wherein the subject has a decreased NAD/NADH ratio as compared to a NAD/NADH ratio of a subject not suffering from heart failure.

Clause 6. The method of clause 1, wherein the subject has mitochondrial dysfunction.

Clause 7. The method of clause 1, wherein the subject has reduced or dysfunctional mitophagy.

Clause 8. The method of clause 1, further comprising administering iron to the subject.

Clause 9. The method of clause 1, wherein a lifespan of the subject is extended as compared to a lifespan of a subject suffering from heart failure and not administered nicotinamide riboside.

Clause 10. A method for treating heart failure in a subject in need thereof, the method comprising administering a therapeutically effective amount of nicotinamide riboside and a therapeutically effective amount of iron to the subject.

Clause 11. The method of clause 10, wherein the heart failure is associated with iron deficiency.

Clause 12. A method for treating heart failure associated with iron deficiency in a subject in need thereof, the method comprising administering a therapeutically effective amount of nicotinamide riboside to the subject.

Clause 13. The method of clause 12, wherein the iron deficiency is in the heart of the subject.

Clause 14. The method of clause 12, wherein anemia is present with the iron deficiency.

Clause 15. The method of clause 12, wherein the subject has a decreased NAD/NADH ratio as compared to a NAD/

NADH ratio of a subject not suffering from heart failure associated with iron deficiency.

Clause 16. The method of clause 12, wherein the subject has mitochondrial dysfunction.

Clause 17. The method of clause 12, wherein the subject has reduced or dysfunctional mitophagy.

Clause 18. The method of clause 12, further comprising administering iron to the subject.

Clause 19. The method of clause 12, wherein a lifespan of the subject is extended as compared to a lifespan of a subject suffering from heart failure associated with iron deficiency and not administered nicotinamide riboside.

Clause 20. A method for treating heart failure associated with iron deficiency in a subject in need thereof, the method comprising administering a therapeutically effective amount of nicotinamide riboside and a therapeutically effective amount of iron to the subject.

Clause 21. A method of identifying a subject suffering from heart failure as a candidate for treatment with nicotinamide riboside, the method comprising: (a) measuring in a sample obtained from the subject a level selected from the group consisting of: (i) a level of a ratio of NAD/NADH; (ii) a level of iron; (iii) a level of FGF21 protein; (iv) a level of Angiopoietin-like 4 (AngPtL4) protein; and (v) any combination thereof; (b) comparing the measured level to a control level; and (c) identifying the subject as a candidate for treatment with nicotinamide riboside if (i) the measured level of the ratio of NAD/NADH is lower than the control level of the ratio of NAD/NADH; (ii) the measured level of iron is lower than the control level of iron; (iii) the measured level of FGF21 protein is higher than the control level of FGF21 protein; (iv) the measured level of AngPtL4 protein is higher than the control level of AngPtL4 protein; or (v) any combination thereof.

Clause 22. The method of clause 21, wherein the heart failure is associated with iron deficiency.

Clause 23. The method of clause 22, wherein the iron deficiency is in the heart of the subject.

Clause 24. The method of clause 22, wherein anemia is present with the iron deficiency.

Clause 25. The method of clause 21, wherein the subject has mitochondrial dysfunction.

Clause 26. The method of clause 21, wherein the subject has reduced or dysfunctional mitophagy.

Clause 27. The method of clause 21, further comprising administering a therapeutically effective amount of nicotinamide riboside to the subject identified as a candidate for treatment with nicotinamide riboside.

Clause 28. The method of clause 27, wherein administration of nicotinamide riboside includes administration of iron to the subject identified as a candidate for treatment with nicotinamide riboside.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for treating heart failure in a subject in need thereof, the method comprising administering a therapeutically effective amount of nicotinamide riboside to the subject, wherein the subject has mitochondrial dysfunction, and wherein nicotinamide riboside is administered to the subject in an amount of from about 500 mg/day to about 2000 mg/day.

2. The method of claim 1, wherein the subject has iron deficiency.

3. The method of claim 1, wherein the subject has a decreased NAD/NADH ratio as compared to a NAD/NADH ratio of a subject not suffering from heart failure.

4. The method of claim 1, further comprising administering iron to the subject.

5. The method of claim 1, wherein a lifespan of the subject is extended as compared to a lifespan of a subject suffering from heart failure and not administered nicotinamide riboside.

6. A method for treating heart failure in a subject in need thereof, the method comprising administering a therapeutically effective amount of nicotinamide riboside and a therapeutically effective amount of iron to the subject, wherein the subject has mitochondrial dysfunction, and wherein nicotinamide riboside is administered to the subject in an amount of from about 500 mg/day to about 2000 mg/day.

7. The method of claim 6, wherein the heart failure is associated with iron deficiency.

8. A method for treating heart failure associated with iron deficiency in a subject in need thereof, the method comprising administering a therapeutically effective amount of nicotinamide riboside to the subject, wherein the subject has mitochondrial dysfunction, and wherein nicotinamide riboside is administered to the subject in an amount of from about 500 mg/day to about 2000 mg/day.

9. The method of claim 8, wherein the iron deficiency is in the heart of the subject.

10. The method of claim 8, wherein the subject has a decreased NAD/NADH ratio as compared to a NAD/NADH ratio of a subject not suffering from heart failure associated with iron deficiency.

11. The method of claim 8, further comprising administering iron to the subject.

12. The method of claim 8, wherein a lifespan of the subject is extended as compared to a lifespan of a subject suffering from heart failure associated with iron deficiency and not administered nicotinamide riboside.

13. A method for treating heart failure associated with iron deficiency in a subject in need thereof, the method comprising administering a therapeutically effective amount of nicotinamide riboside and a therapeutically effective amount of iron to the subject, wherein the subject has mitochondrial dysfunction, and wherein nicotinamide riboside is administered to the subject in an amount of from about 500 mg/day to about 2000 mg/day.

* * * * *